US010393890B2

(12) United States Patent
Tanabe et al.

(10) Patent No.: US 10,393,890 B2
(45) Date of Patent: Aug. 27, 2019

(54) X-RAY IMAGING DEVICE

(71) Applicant: SHIMADZU CORPORATION, Kyoto (JP)

(72) Inventors: Koichi Tanabe, Kyoto (JP); Shingo Furui, Kyoto (JP); Toshinori Yoshimuta, Kyoto (JP); Kenji Kimura, Kyoto (JP); Akihiro Nishimura, Kyoto (JP); Taro Shirai, Kyoto (JP); Takahiro Doki, Kyoto (JP); Satoshi Sano, Kyoto (JP); Akira Horiba, Kyoto (JP); Toshiyuki Sato, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 203 days.

(21) Appl. No.: 15/562,777

(22) PCT Filed: Mar. 1, 2016

(86) PCT No.: PCT/JP2016/056298
§ 371 (c)(1),
(2) Date: Sep. 28, 2017

(87) PCT Pub. No.: WO2016/163177
PCT Pub. Date: Oct. 13, 2016

(65) Prior Publication Data
US 2018/0279972 A1 Oct. 4, 2018

(30) Foreign Application Priority Data
Apr. 9, 2015 (JP) ................................. 2015-080168

(51) Int. Cl.
*G01T 1/20* (2006.01)
*A61B 6/00* (2006.01)

(52) U.S. Cl.
CPC .......... *G01T 1/2018* (2013.01); *A61B 6/4208* (2013.01); *A61B 6/4233* (2013.01); *A61B 6/484* (2013.01)

(58) Field of Classification Search
CPC .............................. G01T 1/2018; A61B 6/484
See application file for complete search history.

(56) References Cited

U.S. PATENT DOCUMENTS

2012/0294421 A1* 11/2012 Mukaide ................ G01N 23/04
378/62
2013/0292574 A1* 11/2013 Levene ................ G01T 1/2018
250/362

FOREIGN PATENT DOCUMENTS

JP 2011-45655 A 3/2011
WO 2013/014083 A1 1/2013

OTHER PUBLICATIONS

Written Opinion dated May 31, 2016 of corresponding International application No. PCT/JP2016/056298; 3 pgs.

(Continued)

*Primary Examiner* — Yara B Green
(74) *Attorney, Agent, or Firm* — Maier & Maier, PLLC

(57) ABSTRACT

In an X-ray imaging device according to a first embodiment, an X-ray detector has a configuration in which scintillator elements are defined by light-shielding walls in a lattice shape. Among X-rays incident on the X-ray detector, X-rays incident on the light-shielding walls are not converted into scintillator light and are transmitted by the X-ray detector. Accordingly, by causing X-rays to be incident on the X-ray detector in which the scintillator elements are defined by the light-shielding walls in a lattice shape, an area in which X-rays 3a transmitted by a subject M are incident on the X-ray detector can be limited to an arbitrary range. Accordingly, since a detection mask can be omitted in the X-ray (Continued)

imaging device which is used for EI-XPCi, it is possible to reduce a manufacturing cost of the X-ray imaging device.

13 Claims, 24 Drawing Sheets

(56) References Cited

OTHER PUBLICATIONS

International Search Report dated May 31, 2016 of corresponding International application No. PCT/JP2016/056298; 3 pgs.
C. K. Hagen et al., "Low-dose phase contrast tomography with conventional x-ray sources", Medical Physics, vol. 41, No. 7, Jul. 2014; 6 pgs.

* cited by examiner

[FIG. 1]
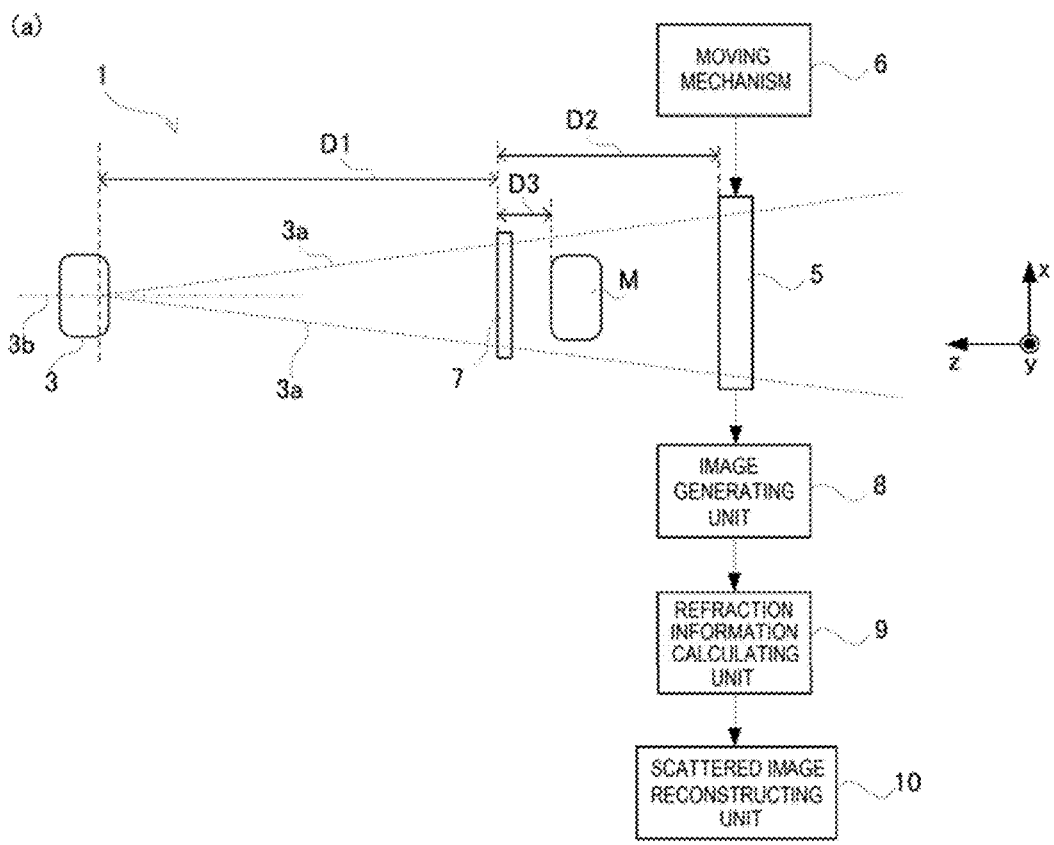
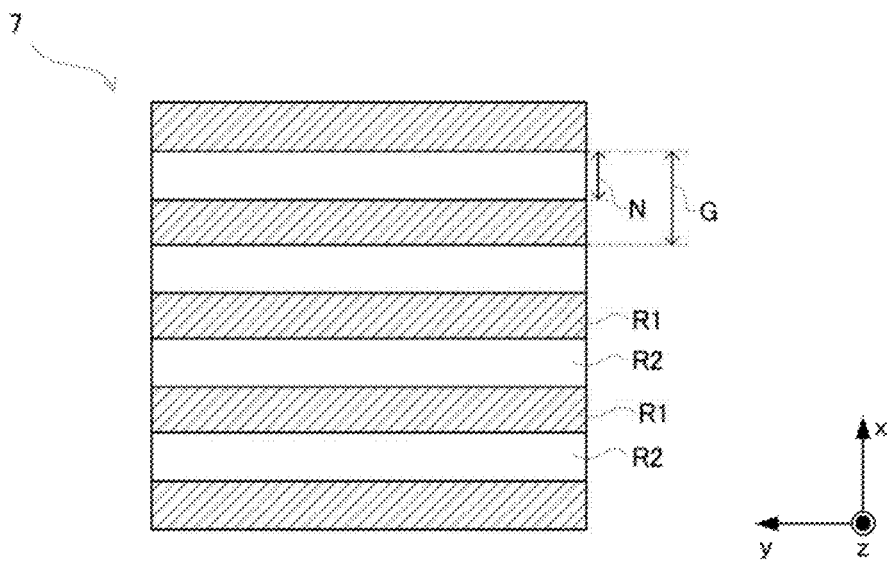

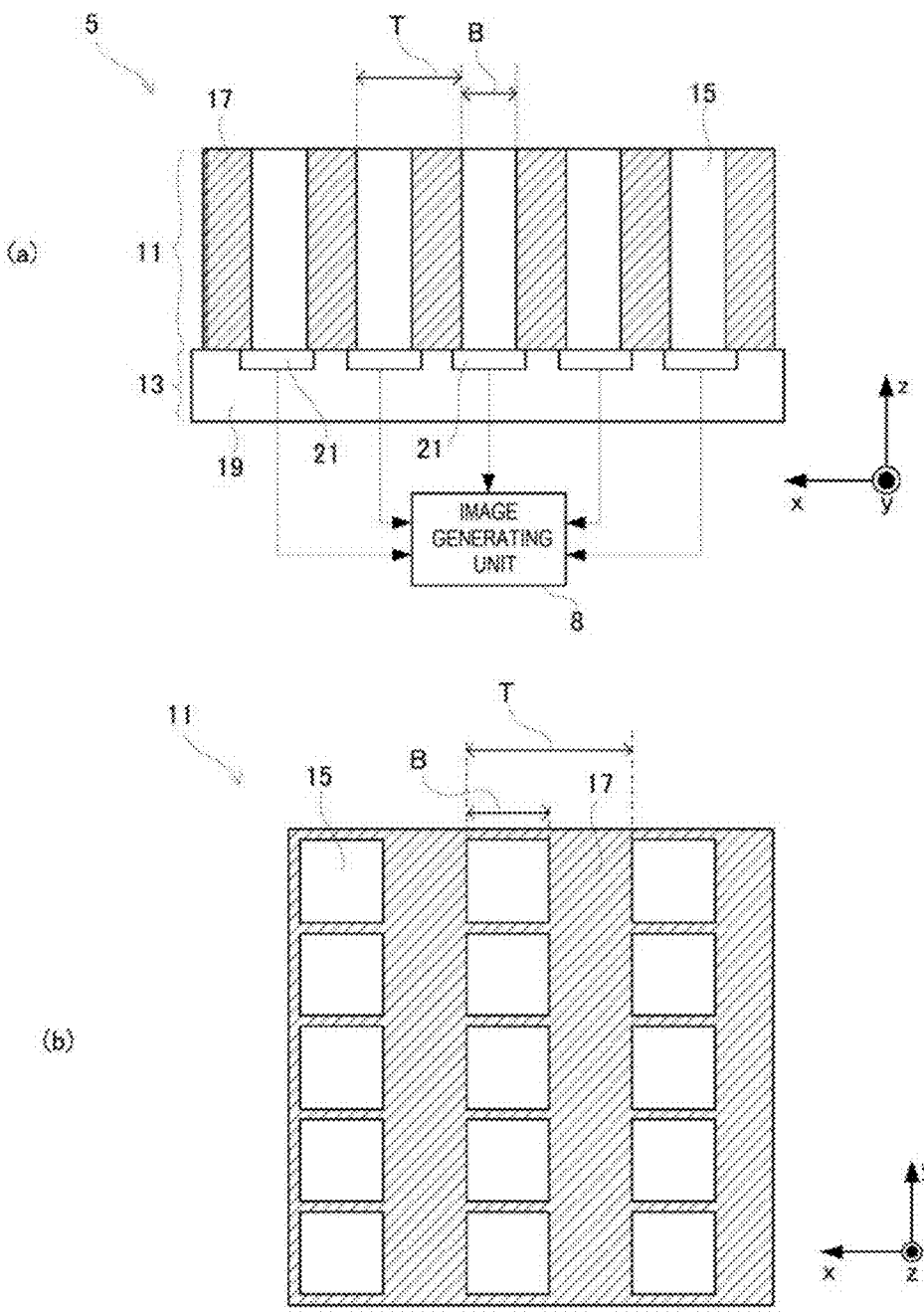

[FIG. 3]
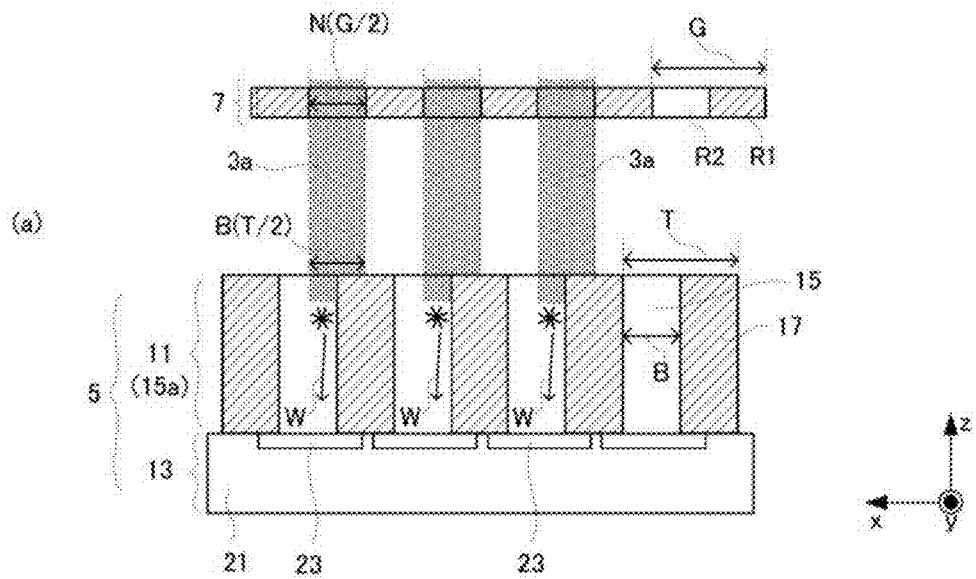
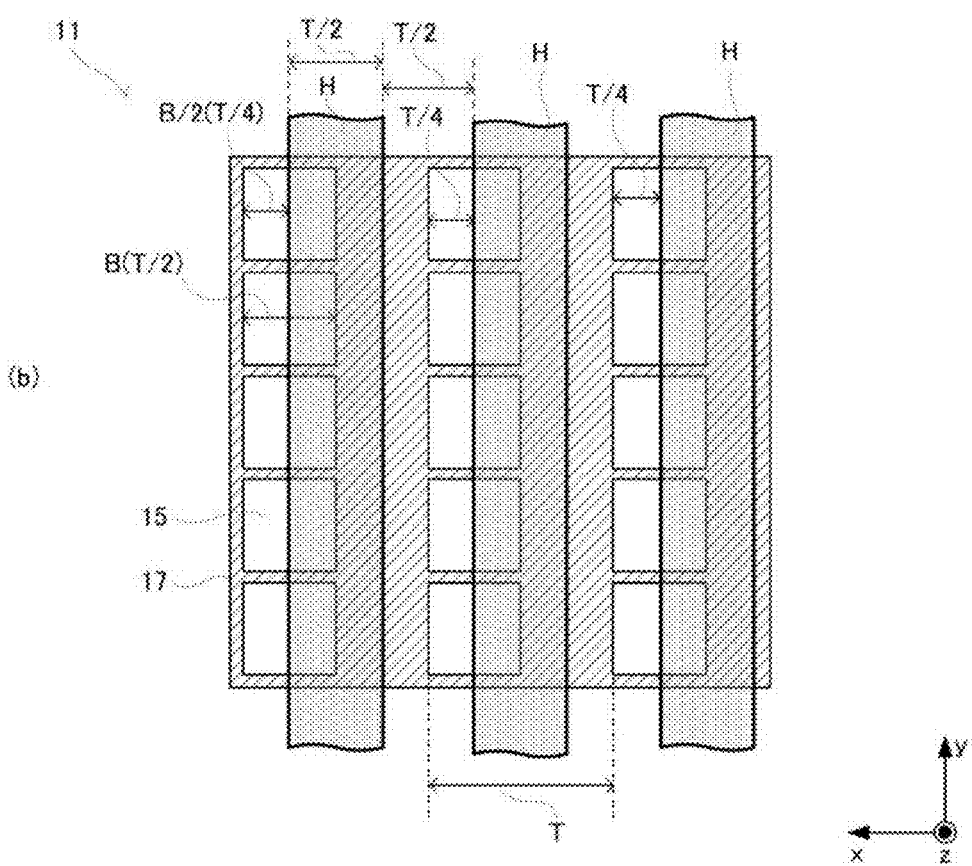

[FIG. 4]
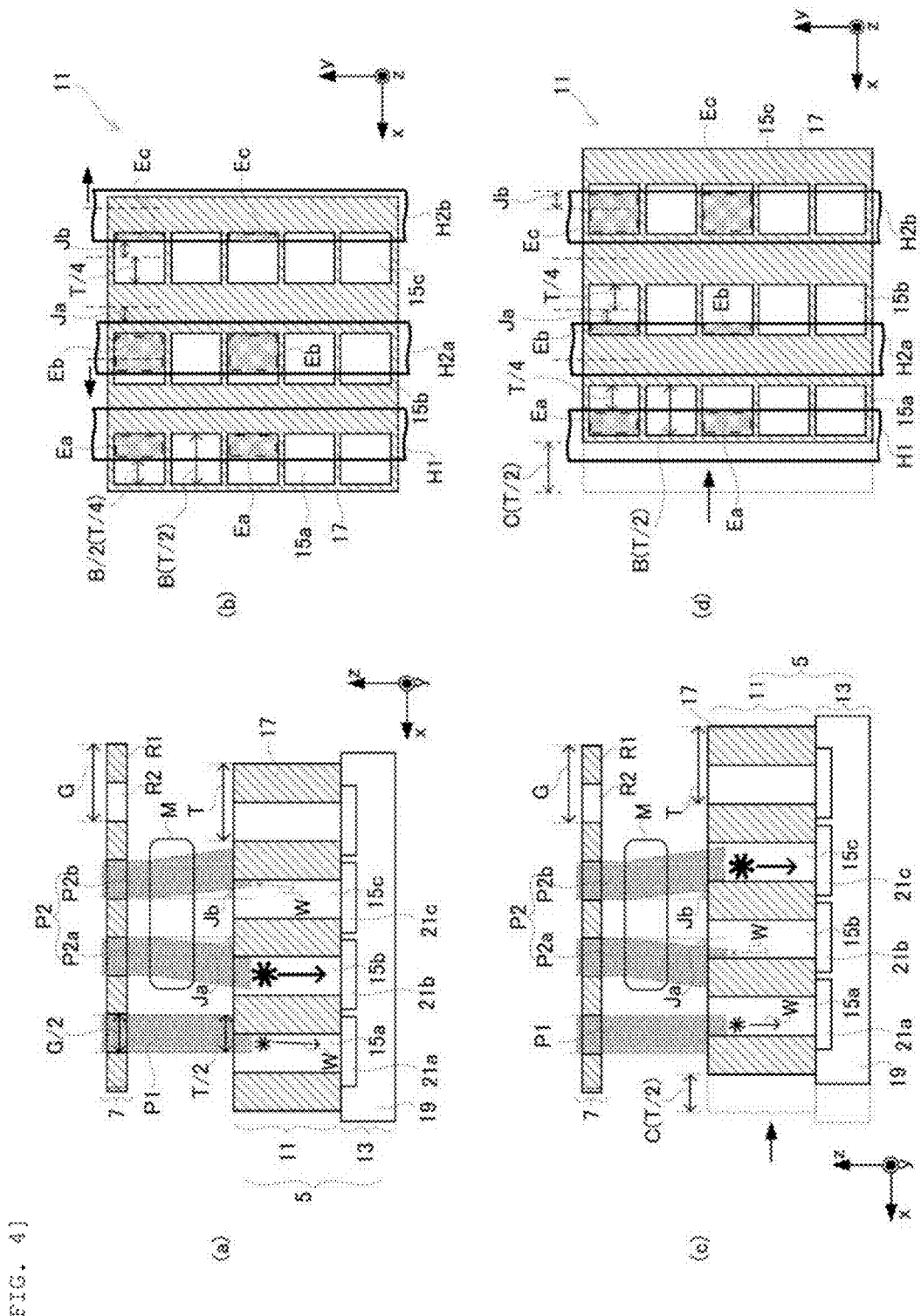

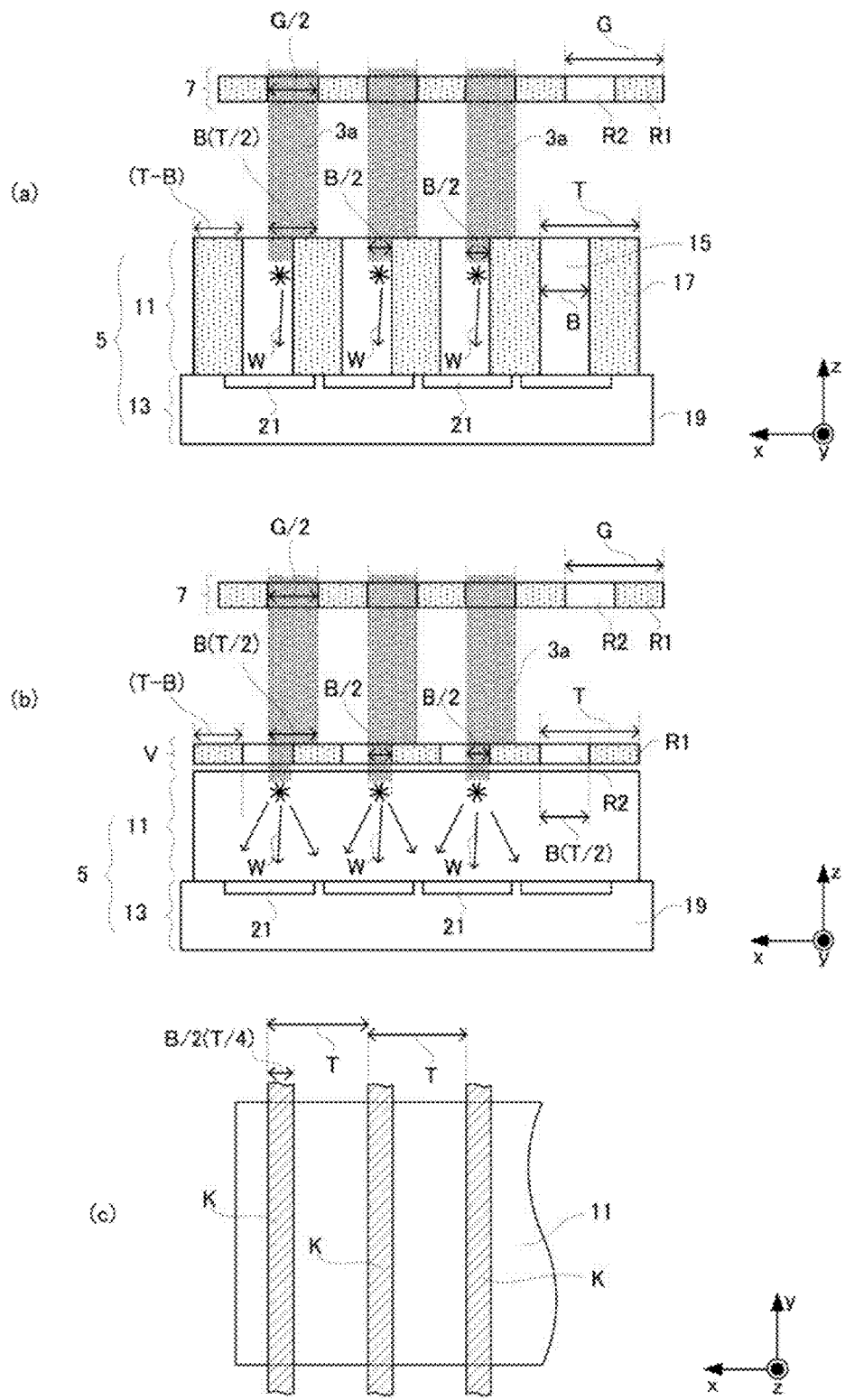
[FIG. 5]

[FIG. 6]
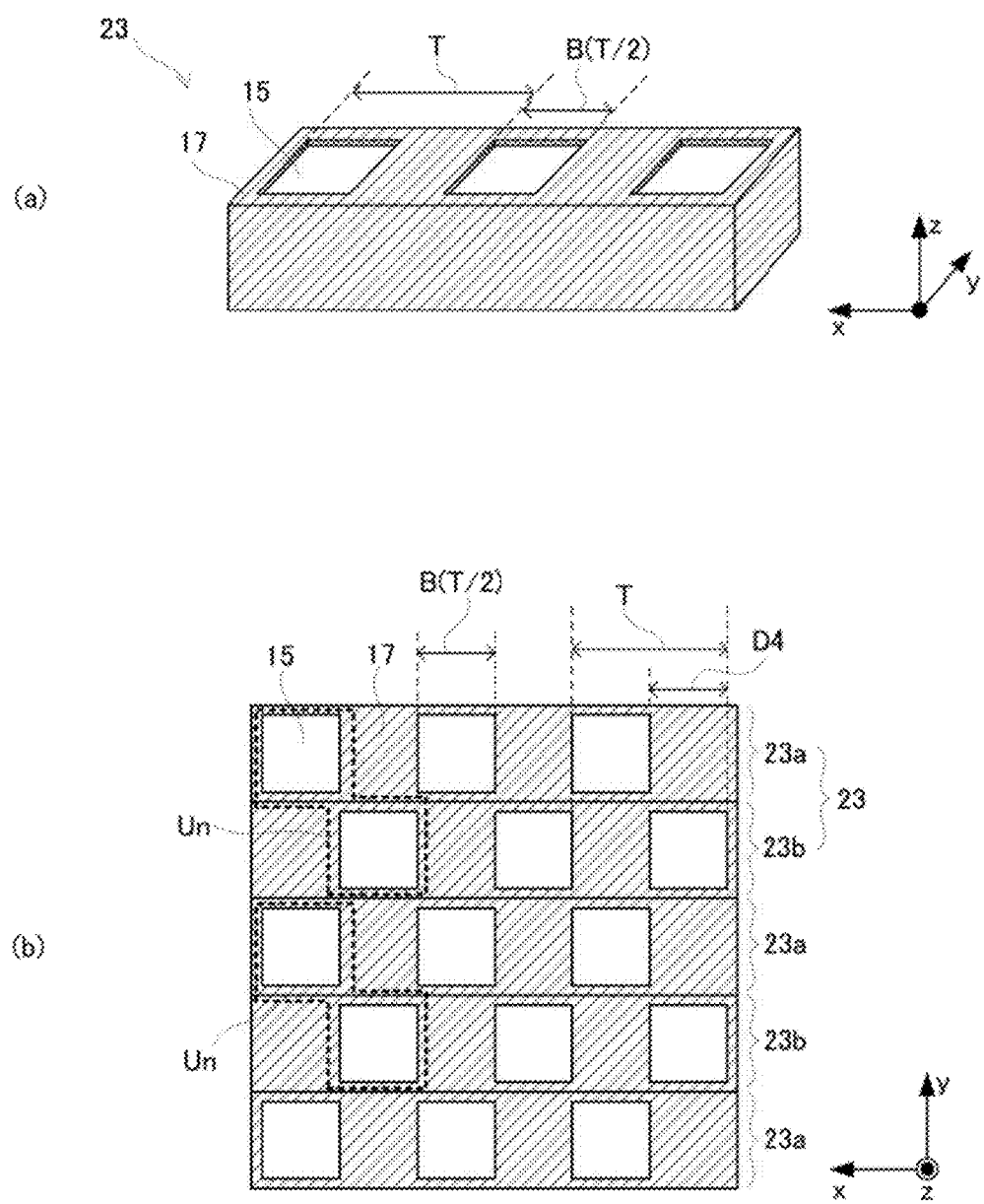

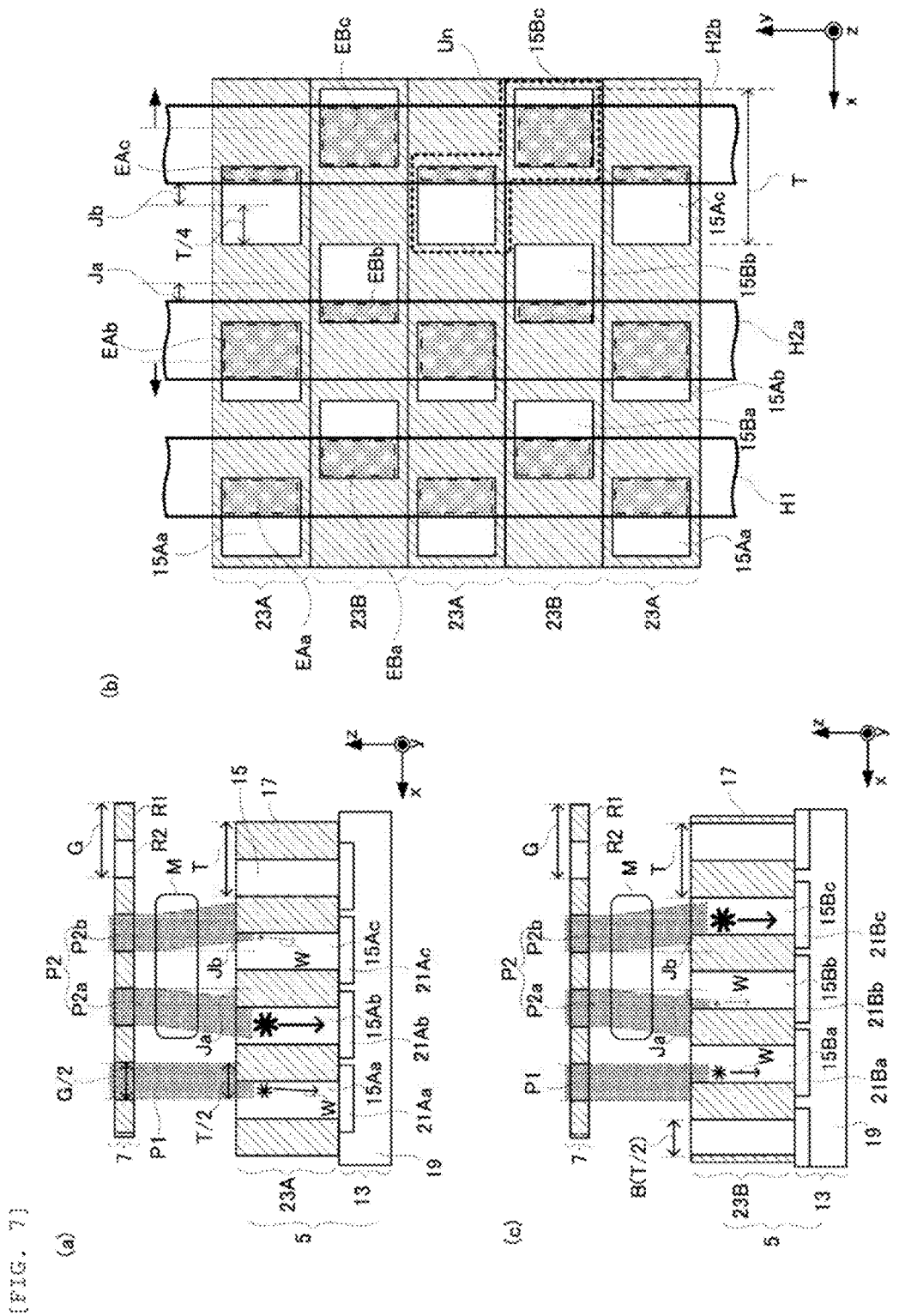

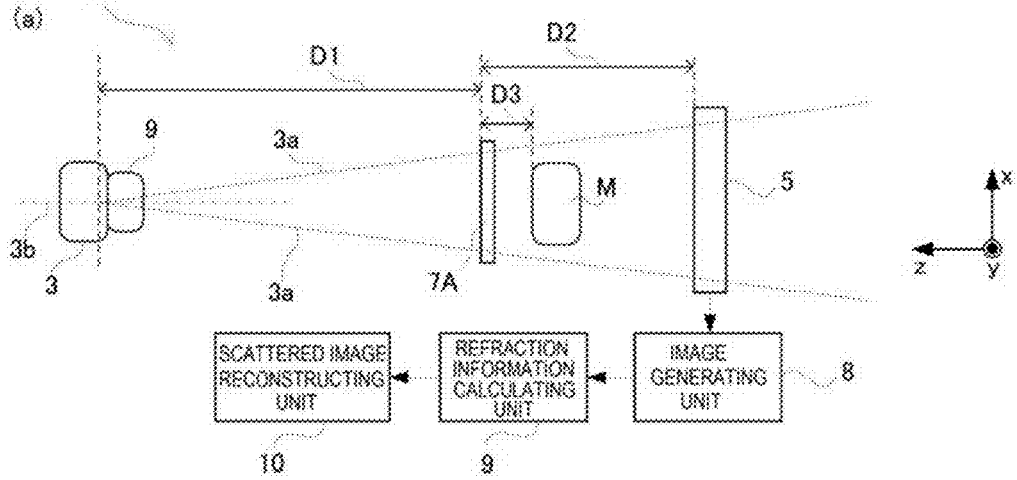
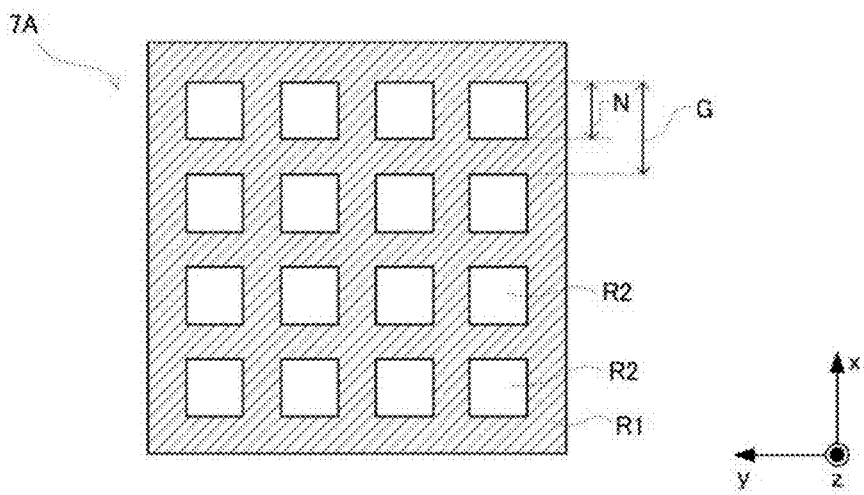
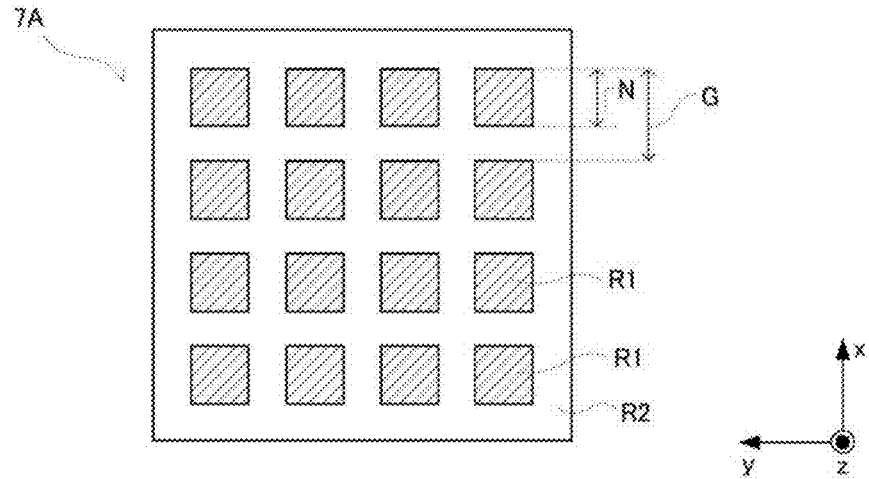

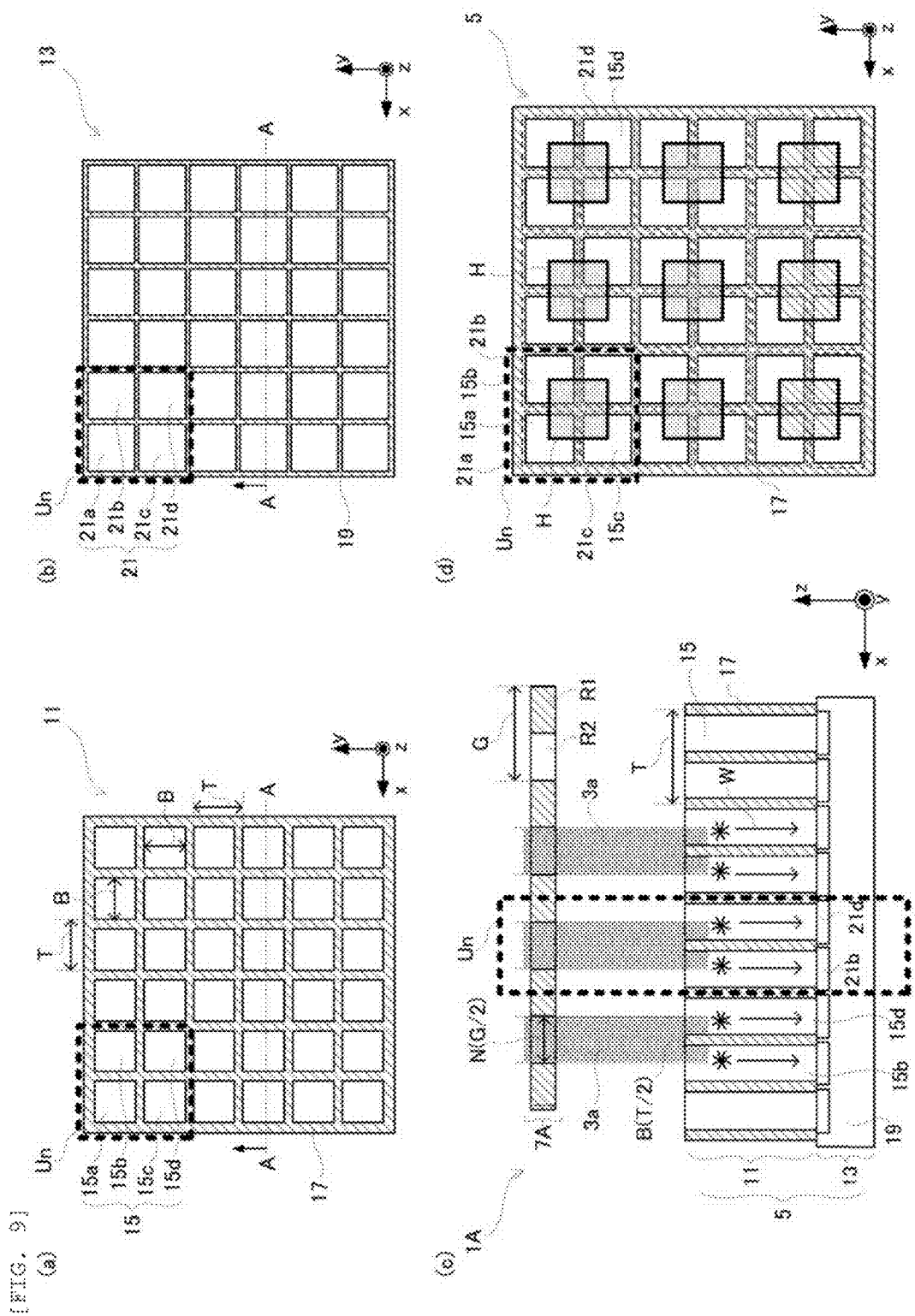
[FIG. 9]

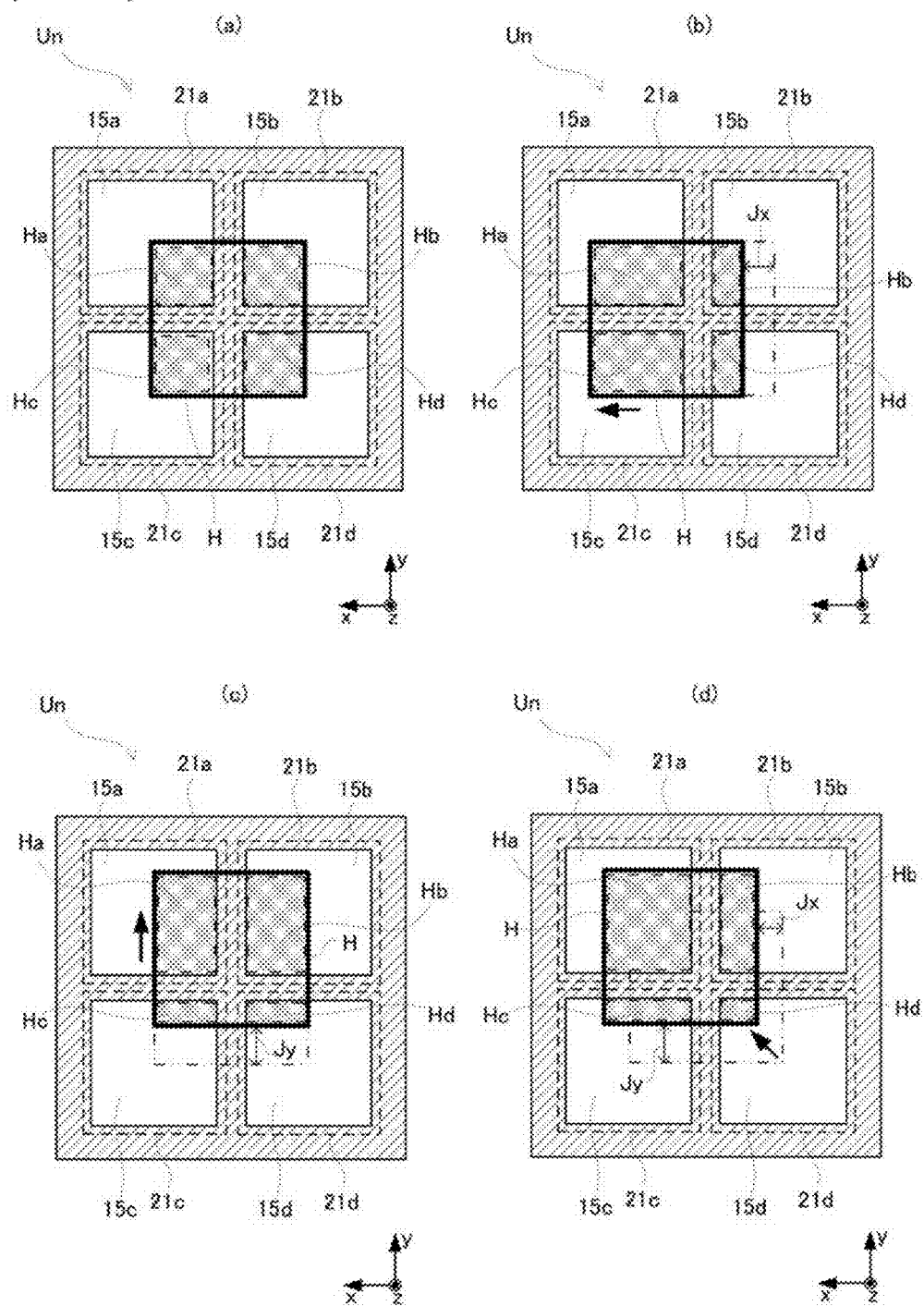
[FIG. 10]

[FIG. 11]
(a)
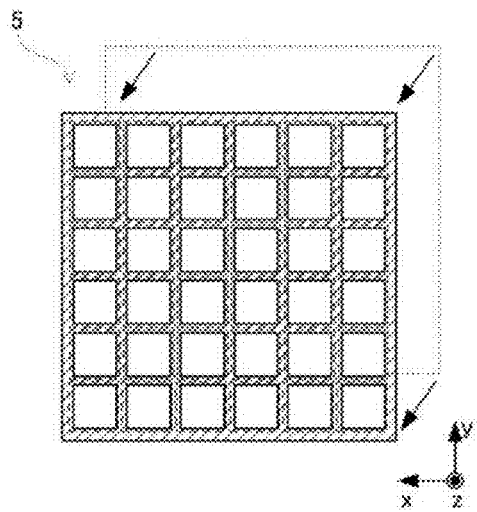
(b)
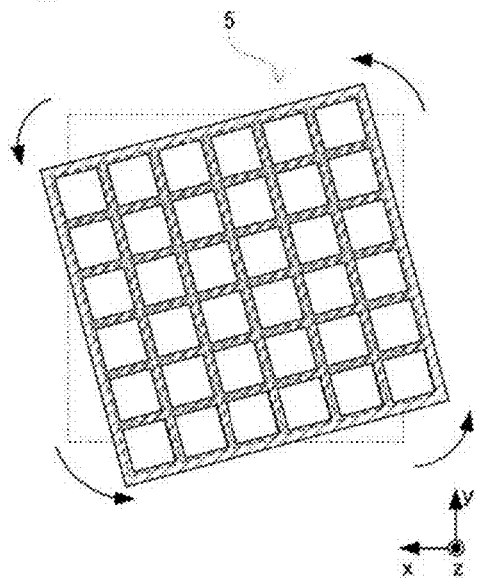
[FIG. 12]
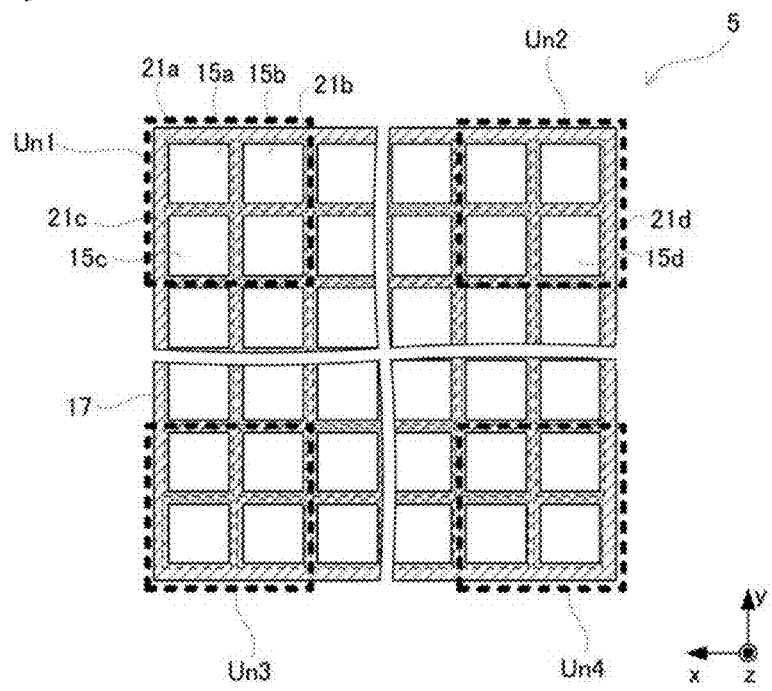

[FIG. 13]
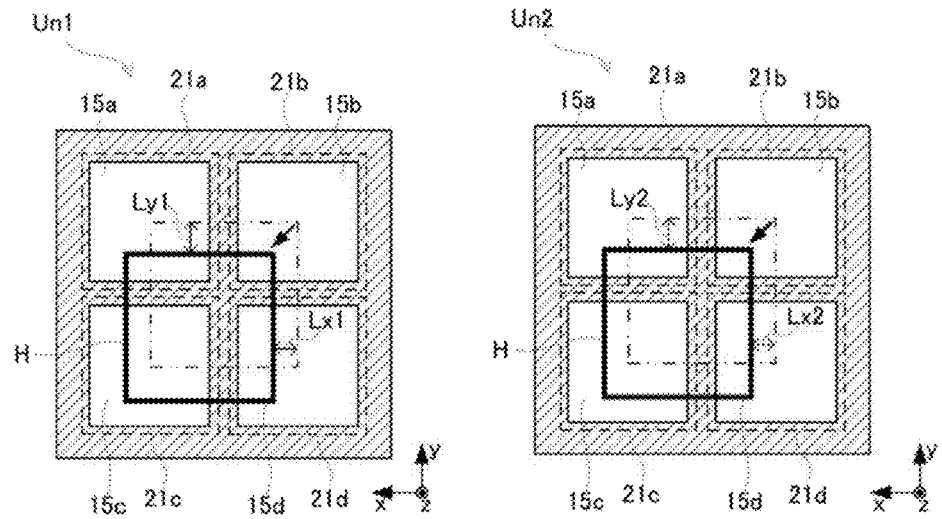
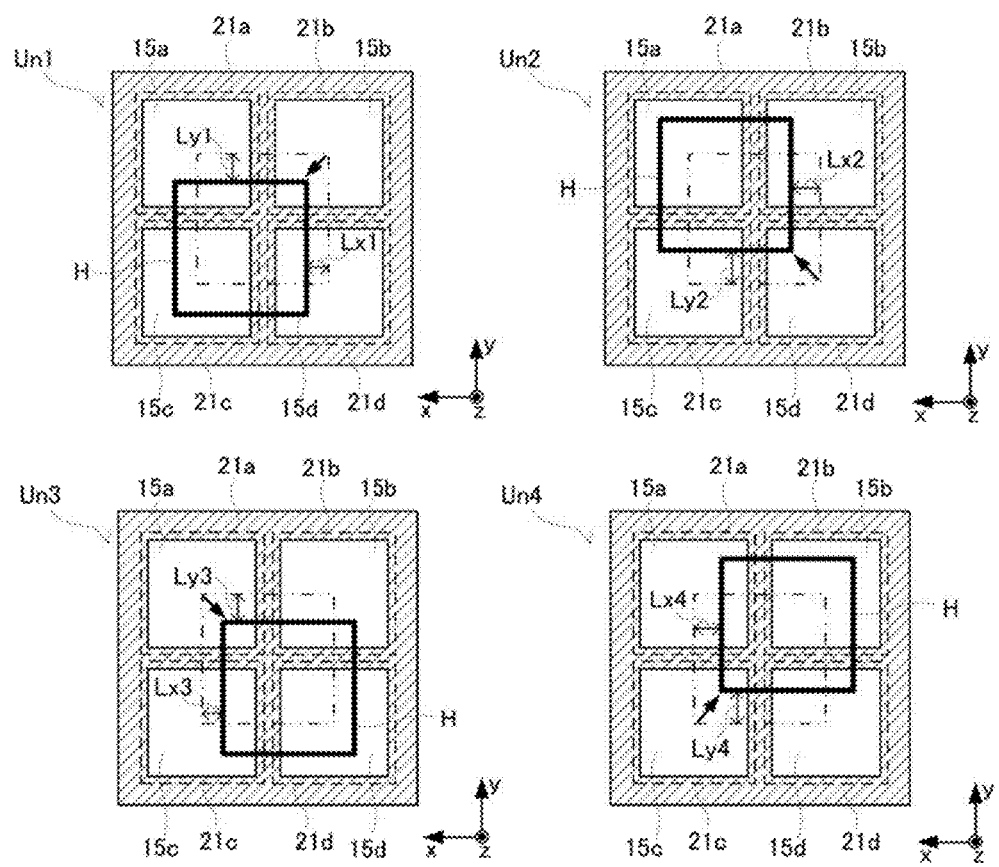

[FIG. 14]
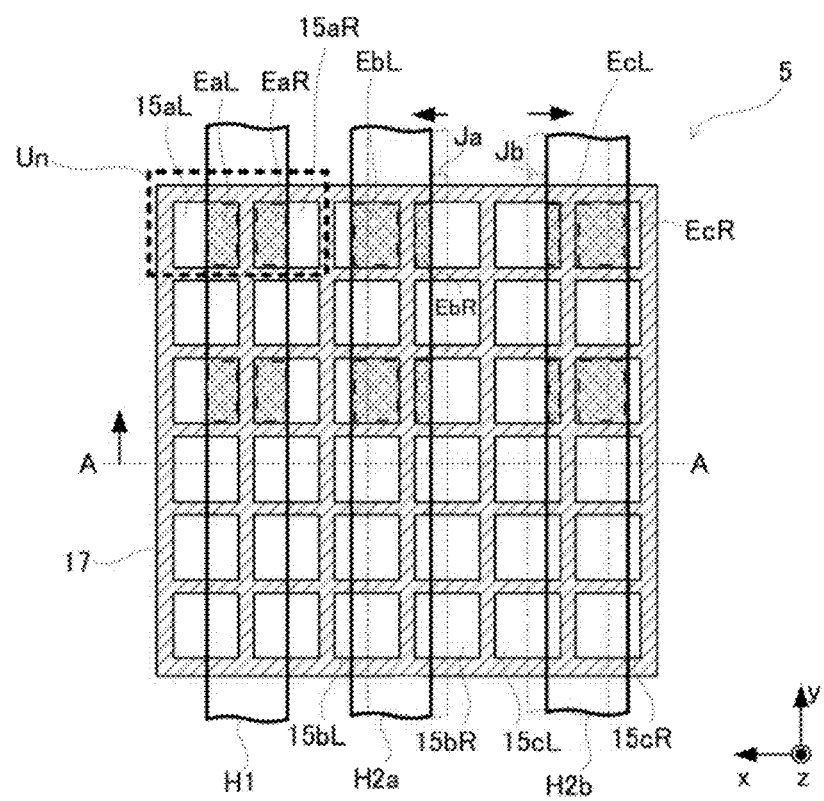
(a)
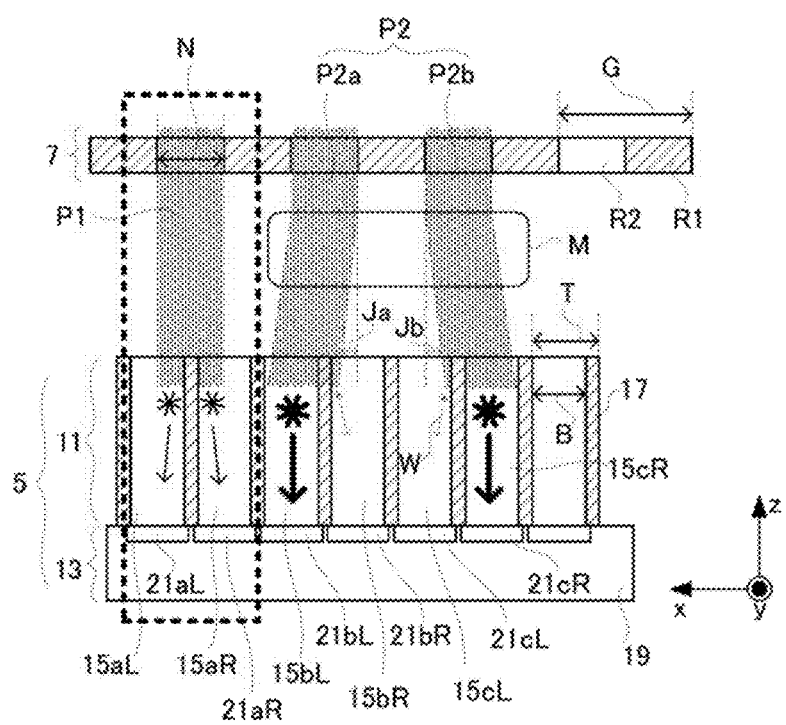
(b)

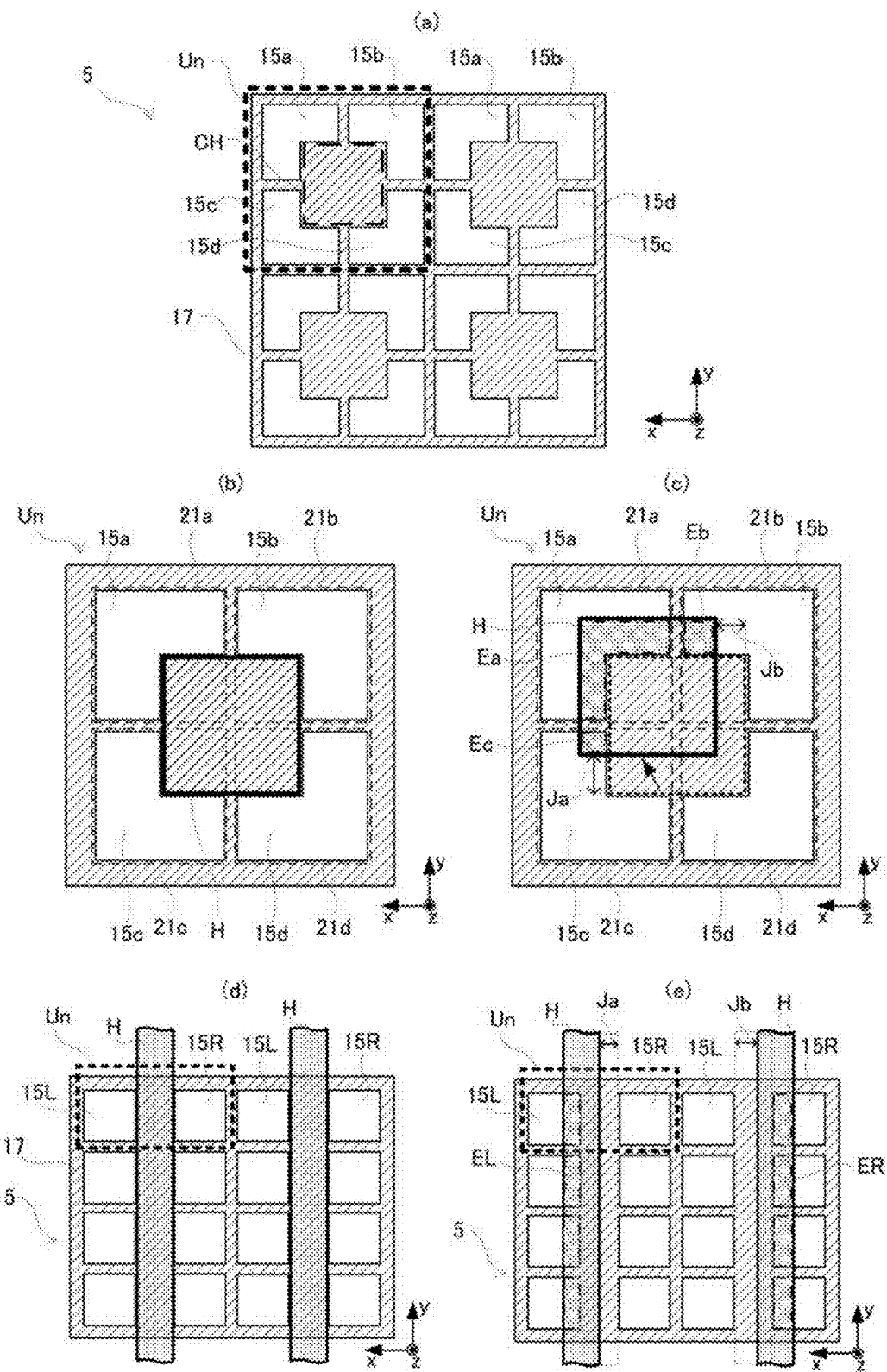
[FIG. 15]

[FIG. 16]
(a)
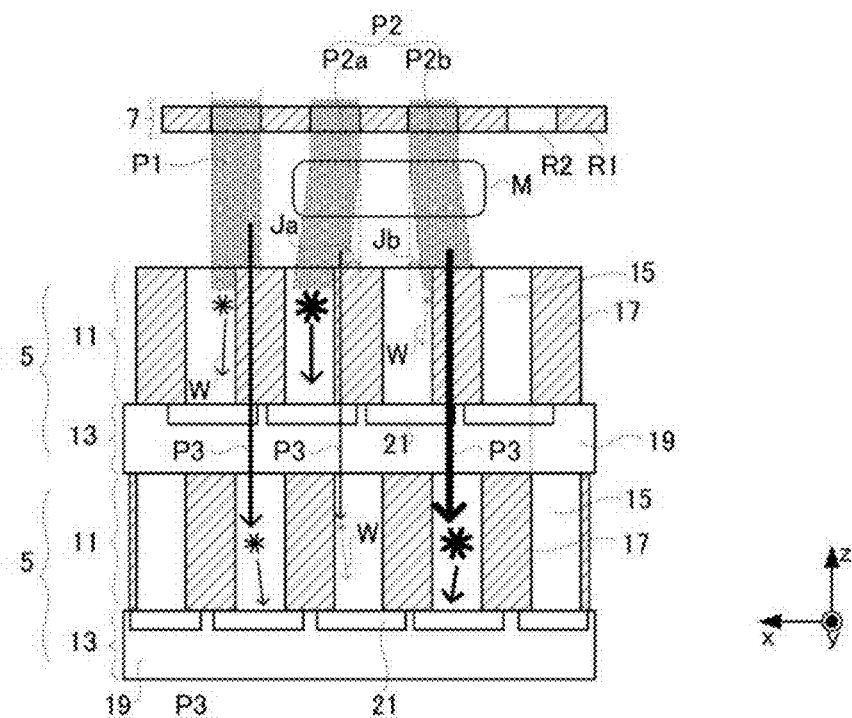
(b)
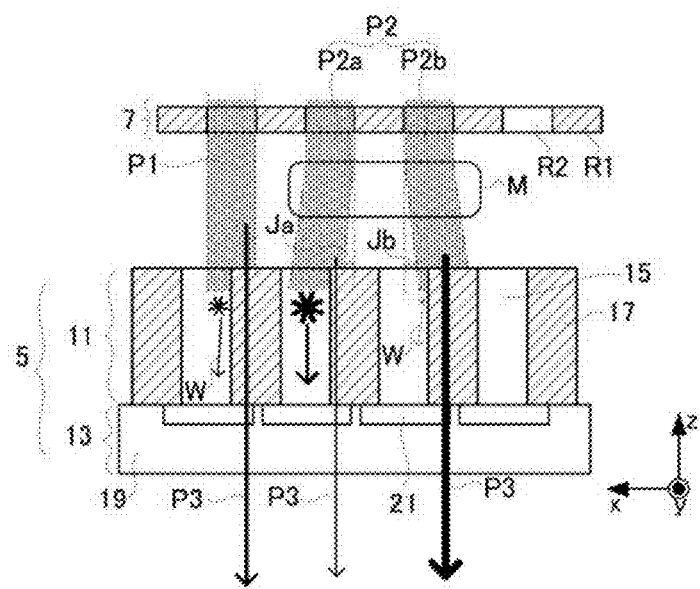

[FIG. 17]
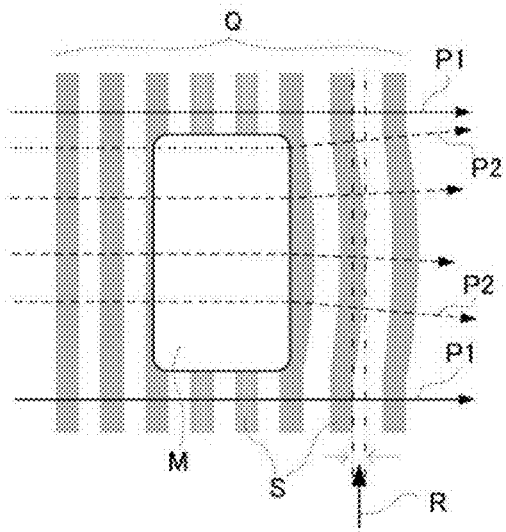
[FIG. 18]
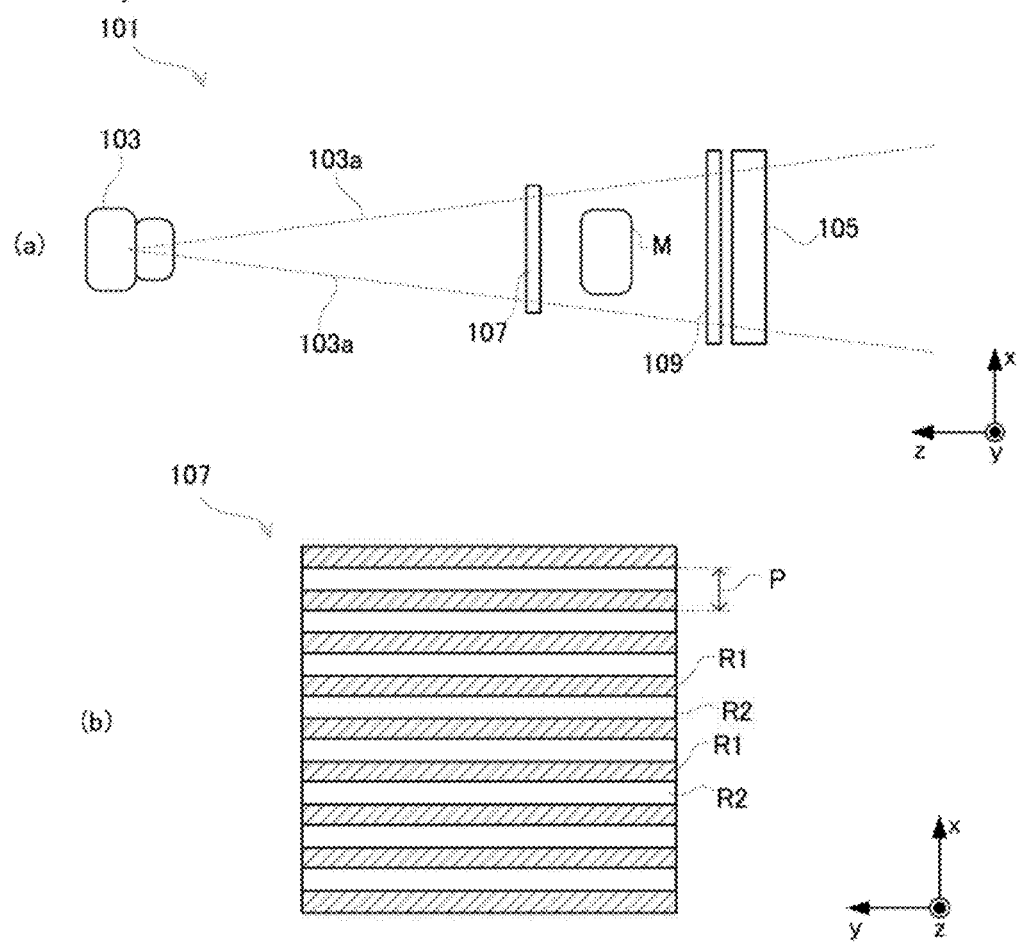

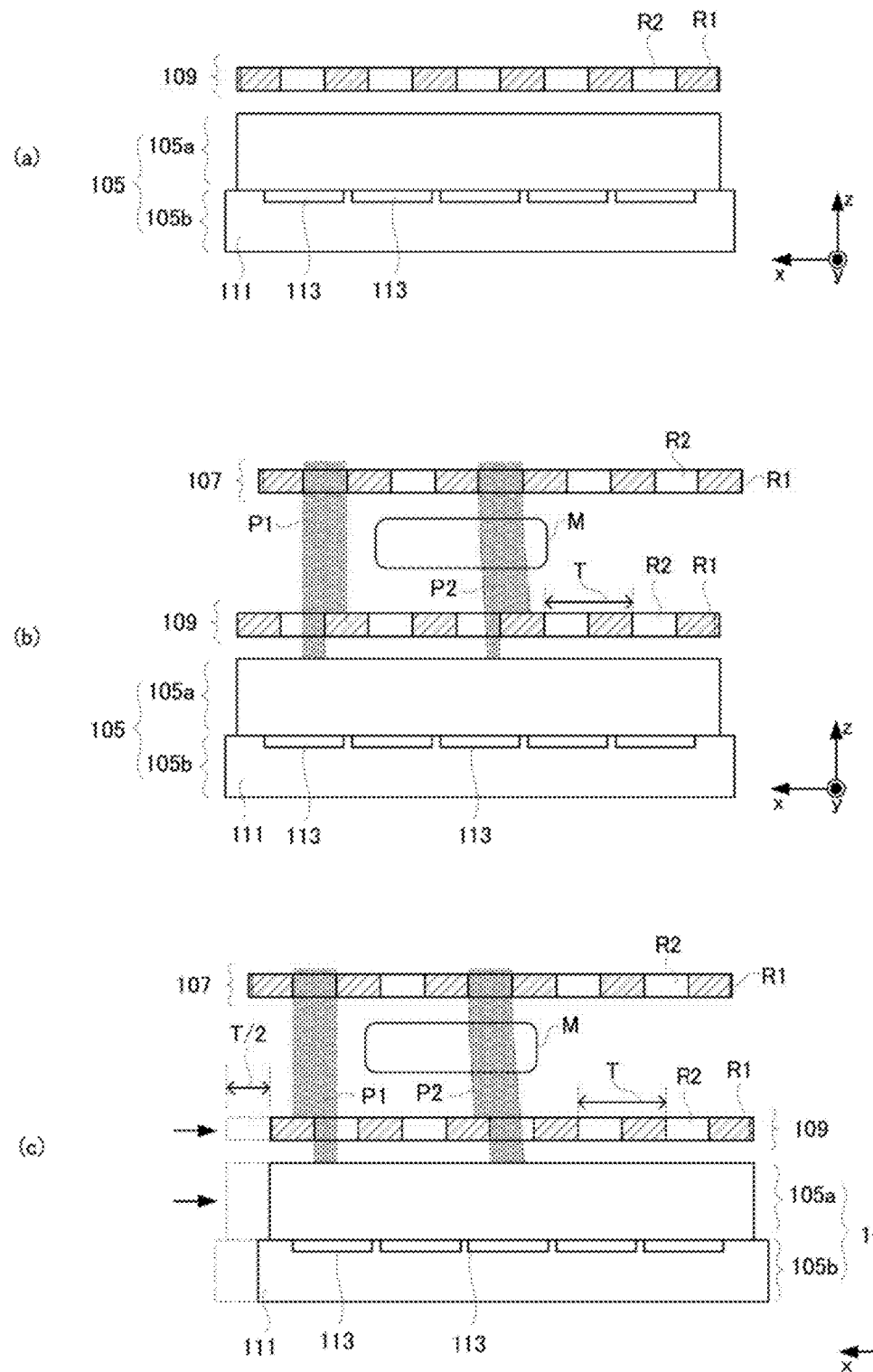

[FIG. 20]
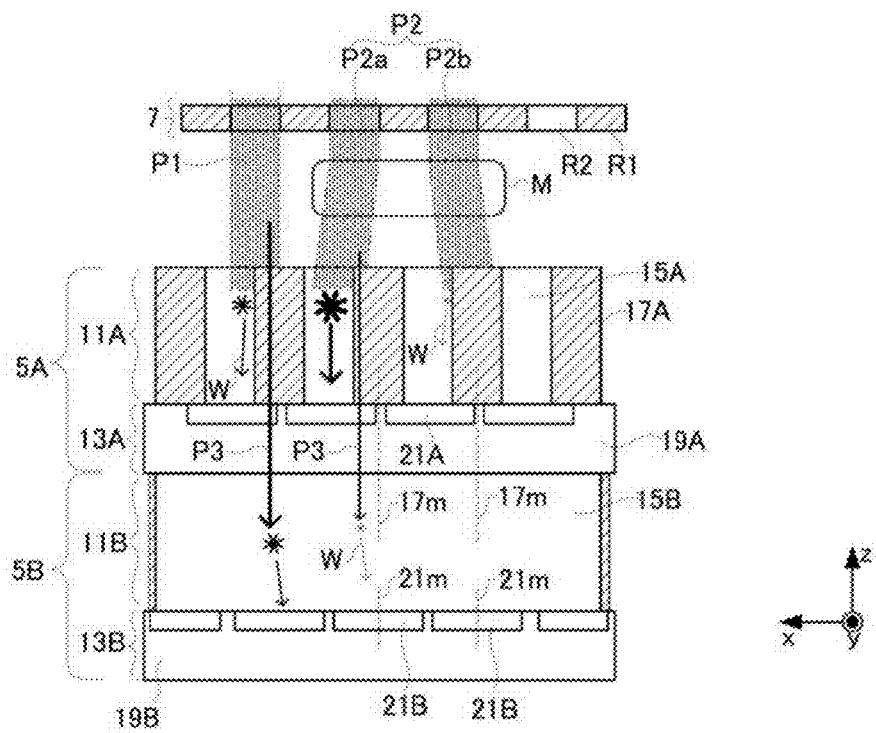
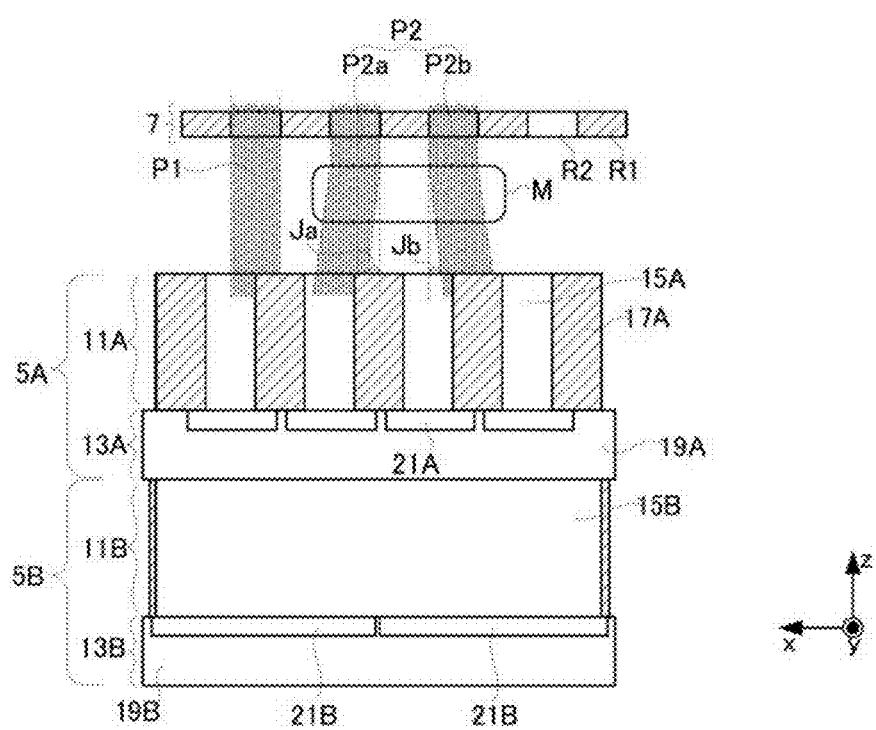

[FIG. 21]
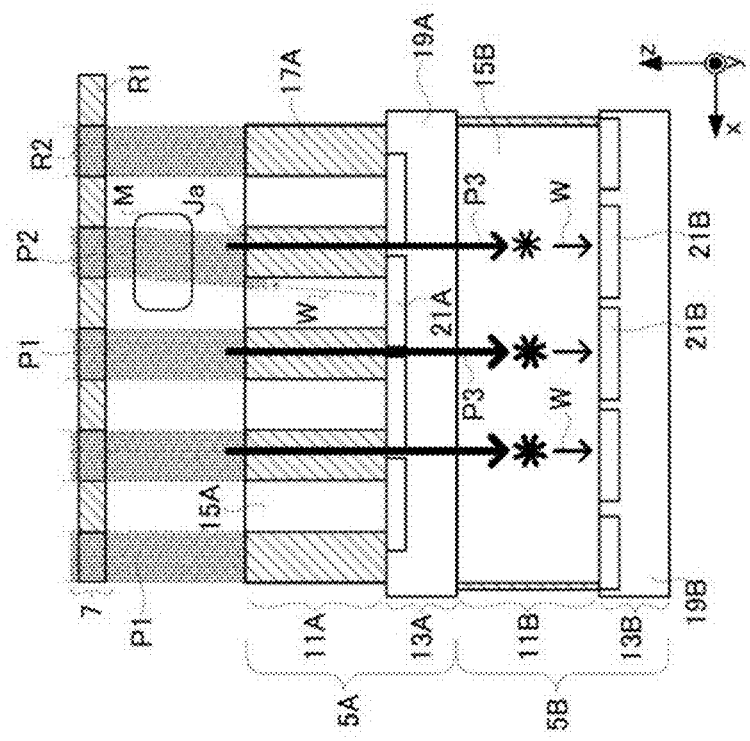
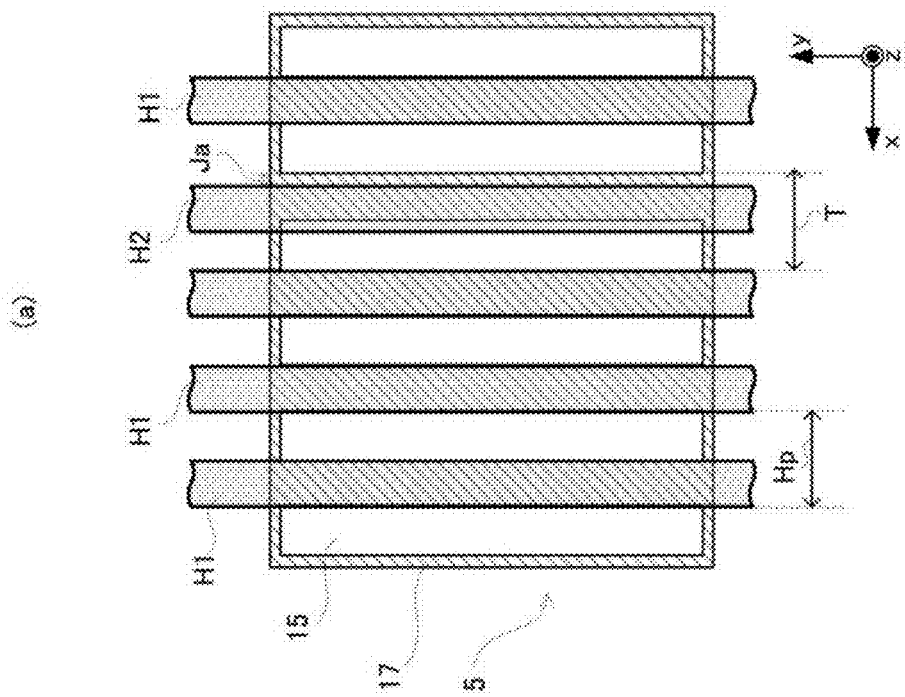

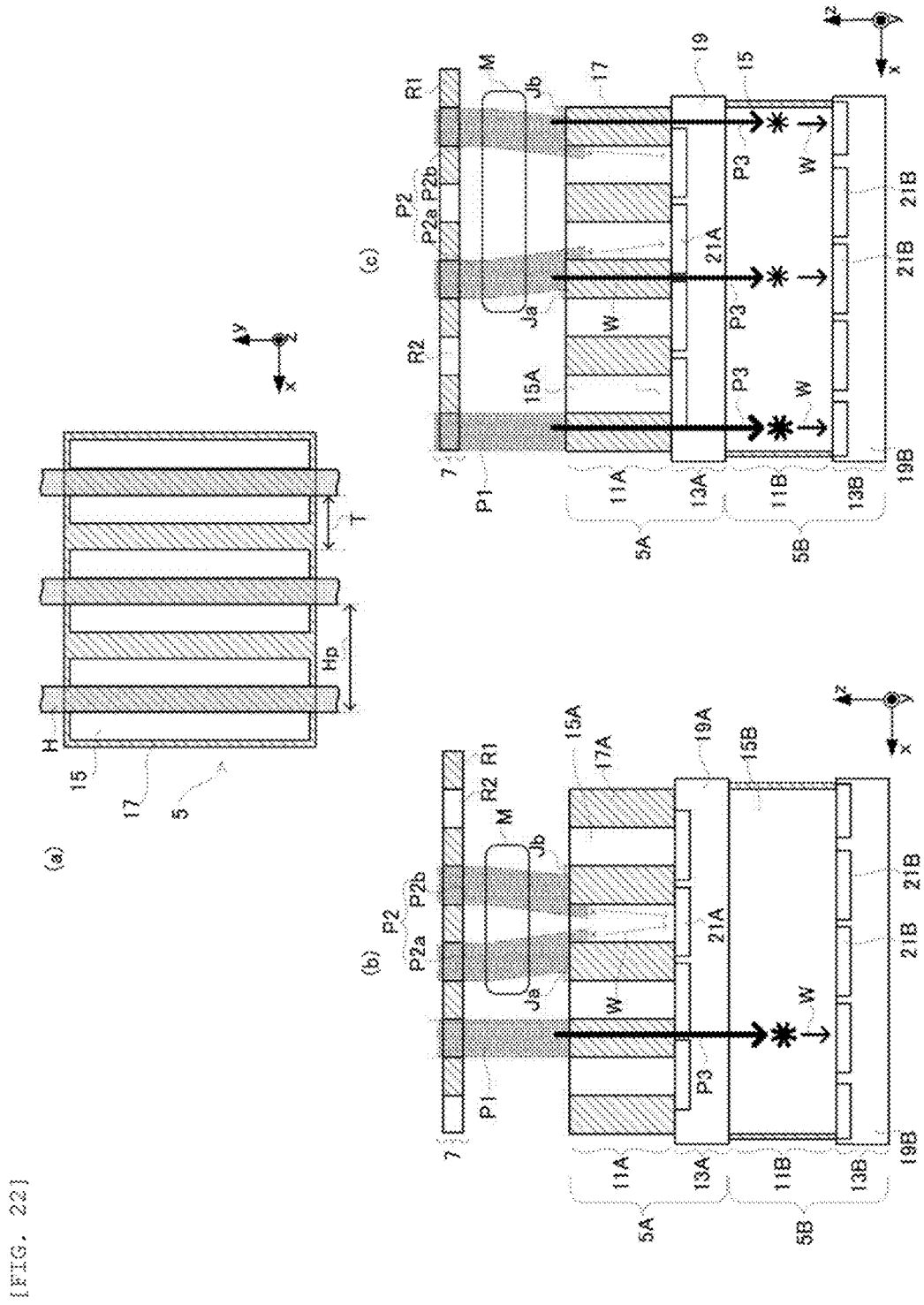
[FIG. 22]

[FIG. 23]
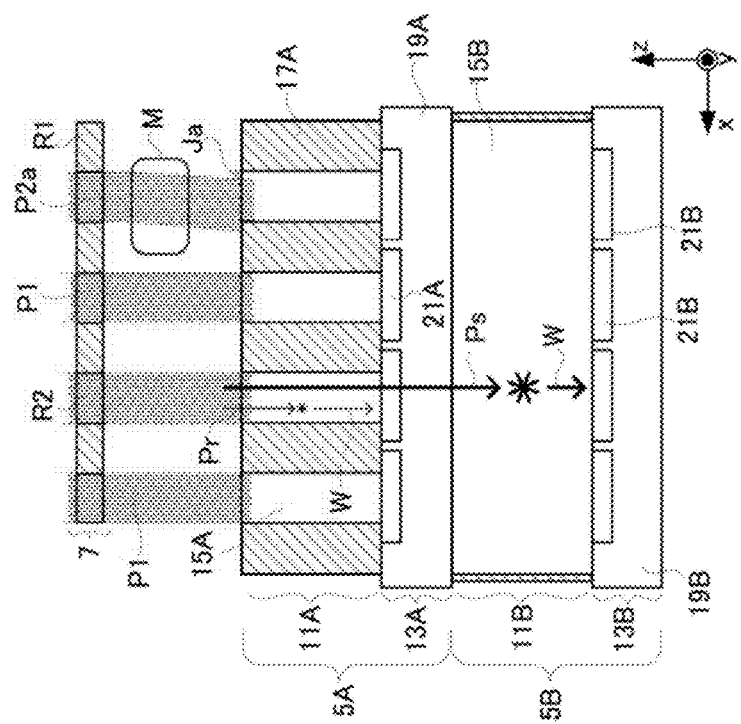
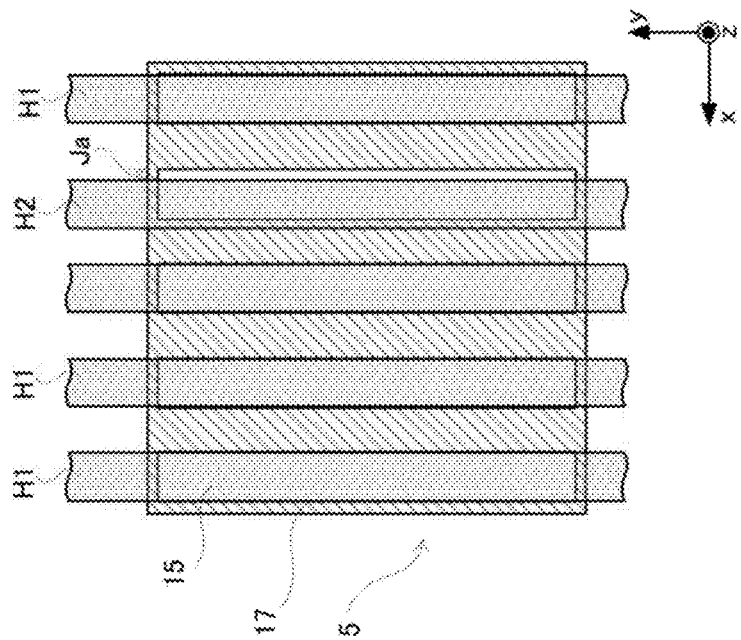

[FIG. 24]
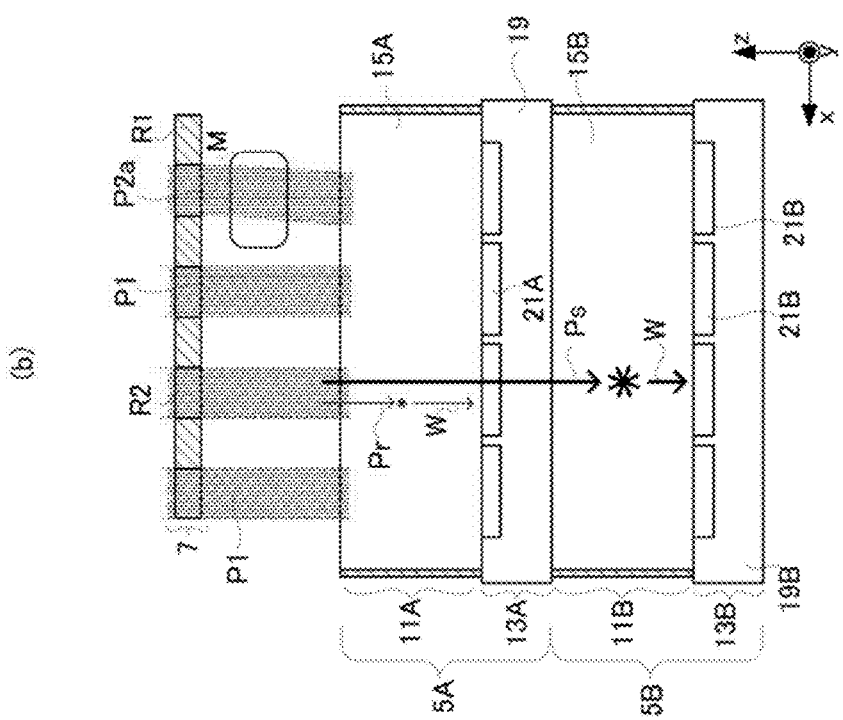
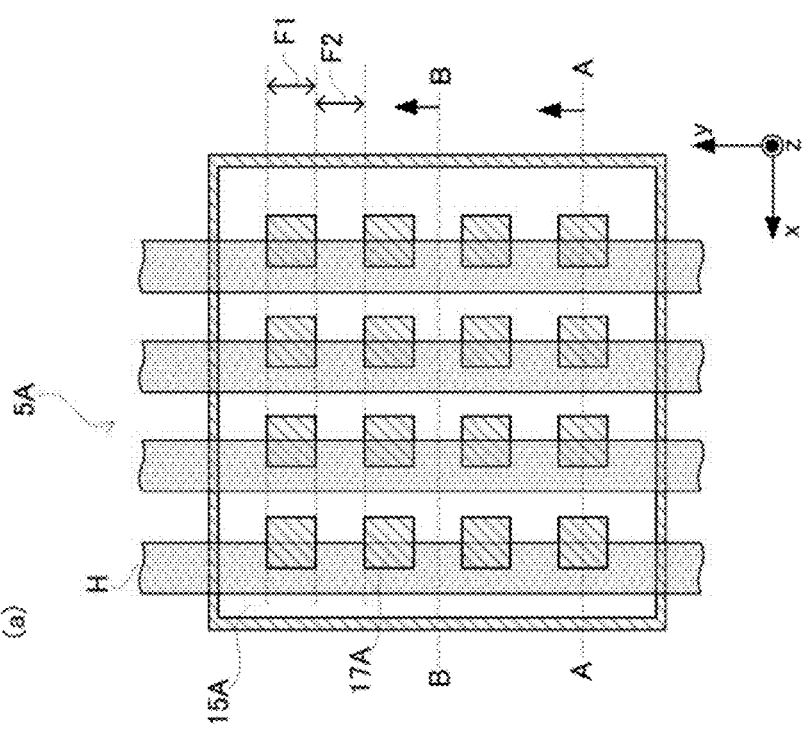

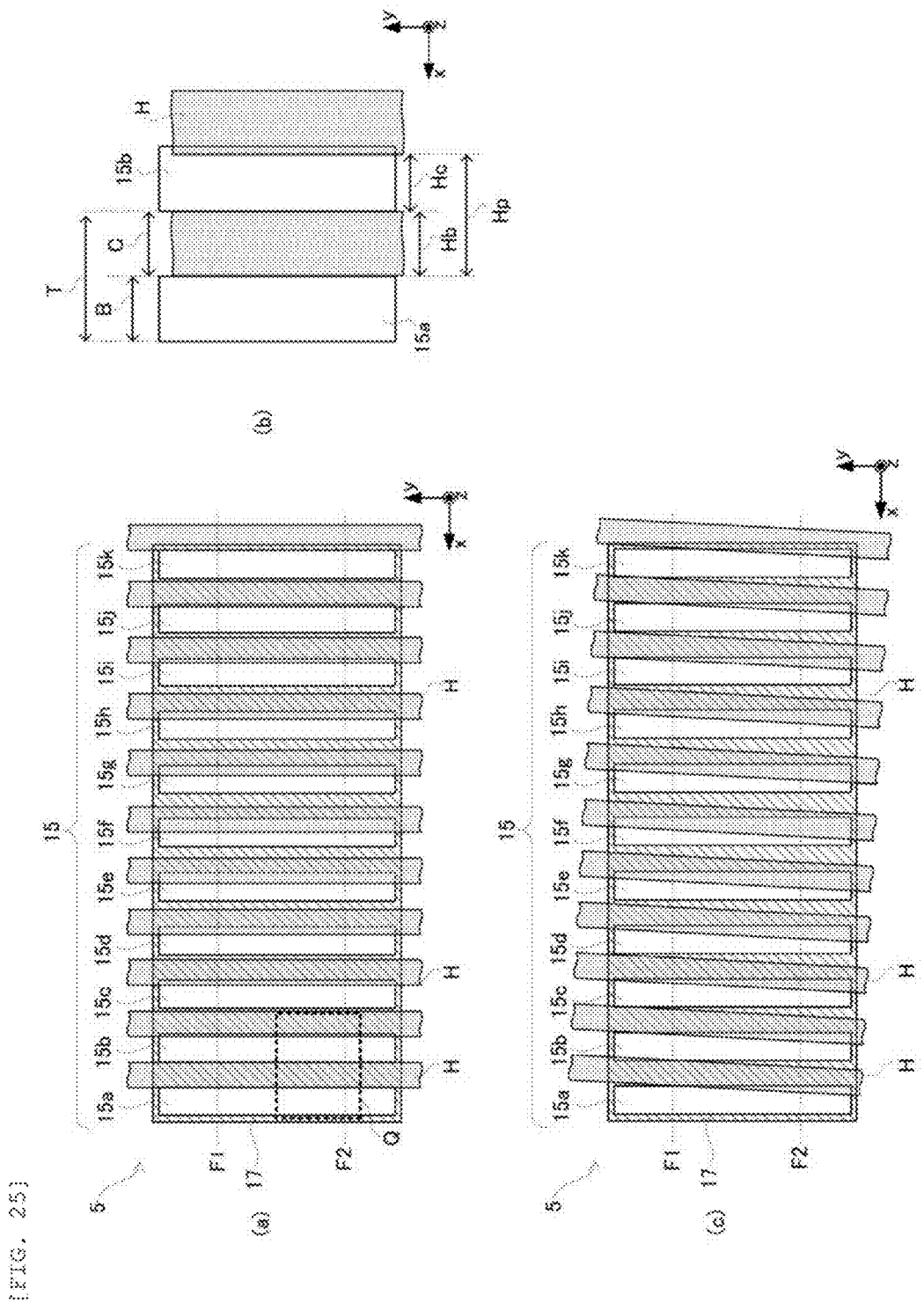
[FIG. 25]

[FIG. 26]
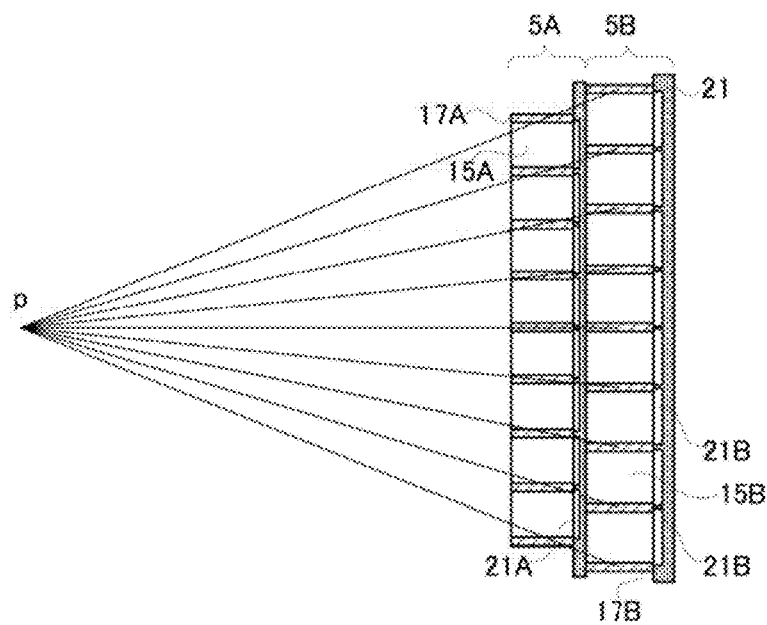
[FIG. 27]
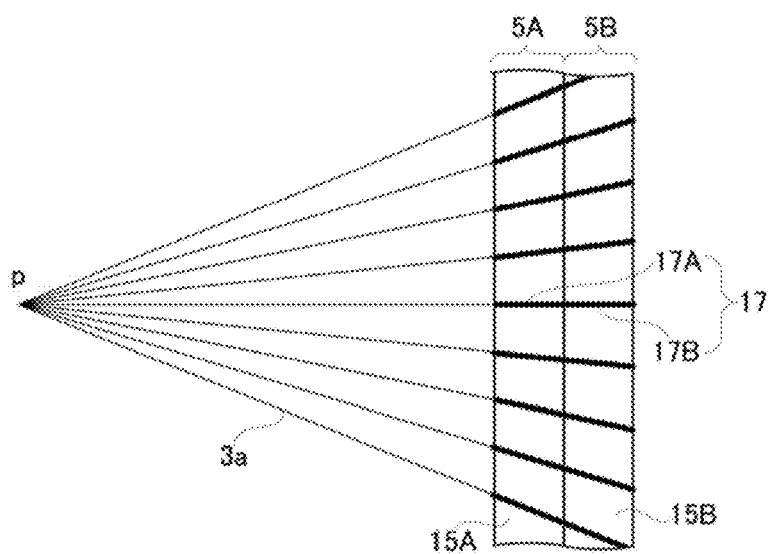
[FIG. 28]
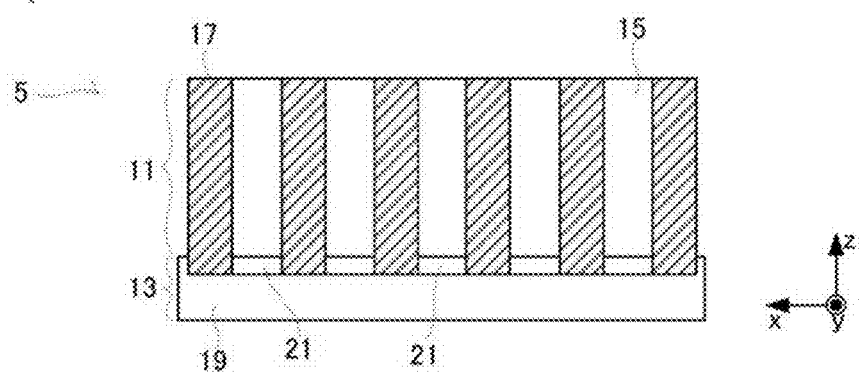

X-RAY IMAGING DEVICE

TECHNICAL FIELD

The present invention relates to an X-ray imaging device that captures an X-ray image of a subject in the field of medicine or the like and more particularly to an X-ray imaging device that captures an X-ray image in which a refraction contrast image of a subject is mirrored.

BACKGROUND ART

In the field of medicine or the like, an X-ray imaging device that emits X-rays and generates an X-ray image is widely used to diagnose inside of a subject. X-ray images which have been generally spread are generated using an absorption imaging method of making a difference in attenuation of X-ray intensity into an image as a contrast.

X-rays emitted to a subject are absorbed and attenuated depending on materials constituting parts of the subject at the time of being transmitted by the subject. X-rays transmitted by a subject are detected as an X-ray absorption image by an X-ray detector and are output as an X-ray detection signal. Since an intensity of an X-ray detection signal varies depending on an X-ray absorption factor, an X-ray image in which a difference in attenuation of an X-ray intensity is expressed as a contrast (a difference in gray level) is generated by performing various image processes on the X-ray detection signal. For example, since a bony tissue has a high X-ray absorption factor, an image of a bony tissue with a high contrast can be acquired using an absorption imaging method.

However, an X-ray absorption factor varies greatly depending on elements constituting a subject and an element having a small atomic number has a small X-ray absorption factor. A soft tissue such as a cartilage including many elements having small atomic numbers hardly absorbs X-rays. Accordingly, it is difficult to acquire an image of a soft tissue with a sufficient contrast from an X-ray image formed using an absorption imaging method.

Therefore, recently, techniques of imaging a subject using a phase difference of X-rays or refraction of X-rays have been proposed (for example, see Patent Documents 1 and 2). X-rays which are a kind of electromagnetic waves have different propagation speeds inside and outside of a subject. Therefore, as illustrated in FIG. 17, phases of X-rays are shifted and waveforms S of the X-rays are changed as indicated by an arrow Q when X-rays are transmitted by a subject M (see reference sign R). As a result, a phenomenon in which traveling directions of X-rays are refracted (scattered) occurs. That is, X-rays P1 which are not transmitted by the subject M propagate straight and X-rays P2 which are transmitted by the subject M are refracted depending on a shape or a constituent material of the subject M or the like.

Actually, a refraction angle of an X-ray is a small angle which is one over several thousands, but an X-ray refraction effect is much larger than an X-ray attenuation effect. Accordingly, an X-ray image with a high contrast can be acquired for a soft tissue having a low X-ray absorption factor or the like by measuring refraction of X-rays due to transmission by a subject. An X-ray image in which a refraction contrast image is mirrored and which is acquired based on refraction information of X-rays due to transmission by a subject is referred to as a small-angle X-ray scattered image. As a technique of capturing such a small-angle X-ray scattered image, an edge illumination X-ray phase contrast imaging (EI-XPCi) method has been recently proposed (for example, see Non-Patent Document 1).

A configuration of a conventional X-ray imaging device that captures a small-angle X-ray scattered image by EI-XPCi will be described below. As illustrated in FIG. 18(a), a conventional X-ray imaging device 101 which is used for EI-XPCi includes an X-ray tube 103 that emits X-rays 103a to a subject M, an X-ray detector 105 that detects the X-rays 103a, a sample mask 107, and a detection mask 109. The sample mask 107 is disposed between the subject M and the X-ray tube 103. The detection mask 109 is disposed at a position close to the X-ray detector 105 between the subject M and the X-ray detector 105.

As illustrated in FIG. 18(b), each of the sample mask 107 and the detection mask 109 has a configuration in which X-ray absorbing materials R1 that extend in a y direction and absorb X-rays and X-ray transmitting materials R2 that extend in the y direction and transmit X-rays are alternately arranged. A pitch T in the sample mask 107 and the detection mask 109 ranges, for example, from about 60 μm to 100 μm and the X-ray absorbing materials R1 and the X-ray transmitting materials R2 have substantially the same length in an x direction.

A flat panel type detector (FPD) or the like is used as the X-ray detector 105. Here, an indirect conversion type X-ray detector that converts X-rays into light using a scintillator element or the like and converts the light into electric charges which are an electrical signal will be described as an example. As illustrated in FIG. 19(a), the X-ray detector 105 has a configuration in which a scintillator layer 105a and an output layer 105b are stacked in a z direction. The scintillator layer 105a includes scintillator elements that absorb X-rays and convert the absorbed X-rays into light.

The output layer 105b includes a substrate 111 and pixels 113 that are arranged in a two-dimensional matrix shape. Each of the pixels 113 includes a photoelectric conversion element and an output element which are not illustrated. In the x direction, the pixels 113 are arranged to correspond to the X-ray transmitting materials R2 of the detection mask 109 in a one-to-one manner.

A part of X-rays emitted from the X-ray tube 103 in the z direction are absorbed by the X-ray absorbing materials R1 of the sample mask 107 and the X-rays are limited to a fan beam shape of which a length in the x direction corresponds to the length of the X-ray transmitting materials R2 and which extends in the y direction. X-rays with a fan beam shape transmitted by the X-ray transmitting materials R2 of the sample mask 107 are incident on the subject M. The X-rays transmitted by the subject M are incident on the detection mask 109 and a part thereof is absorbed by the X-ray absorbing materials R1 disposed in the detection mask 109. X-rays which are transmitted by the X-ray transmitting materials R2 of the detection mask 109 and which are shaped into a fan beam shape narrower in the x direction are incident on the X-ray detector 105.

X-rays incident on the X-ray detector 105 are converted into light in the scintillator layer 105a and are emitted as scintillator light. The scintillator light is transferred to the pixels 111, is subjected to photoelectric conversion by photoelectric conversion elements disposed in the pixels 111, is converted into electric charges which are an electrical signal, and is output as an X-ray detection signal from the output elements. An X-ray image is generated based on the output X-ray detection signal.

When a small-angle X-ray scattered image is captured by EI-XPCi, an X-ray image is captured while moving the sample mask 107 and the detection mask 109 to be relative to each other. That is, X-rays are emitted with a positional relationship illustrated in FIG. 19(b), an X-ray image A1 is captured, and then the detection mask 109 and the X-ray detector 105 are further moved in the x direction. For example, the moving distance corresponds to half the pitch T of the detection mask 109. As illustrated in FIG. 19(c), after the detection mask 109 and the X-ray detector 105 are moved in the x direction, X-rays are emitted again and an X-ray image A2 is captured.

X-ray refraction information based on the subject M can be acquired using the X-ray image A1 and the X-ray image A2 which have been captured while relatively moving two masks. That is, X-rays P1 which are not transmitted by the subject M among X-rays transmitted by the X-ray transmitting materials R2 of the sample mask 107 are not refracted. Accordingly, in the X-ray image A1 and the X-ray image A2, a dose of X-rays P1 incident on the X-ray detector 105 is constant regardless of whether the subject M is present.

On the other hand, X-rays P2 among X-rays transmitted by the X-ray transmitting materials R2 of the sample mask 107 are refracted due to transmission by the subject M. Accordingly, the dose of X-rays P2 incident on the X-ray detector 105 in the X-ray image A1 and the X-ray image A2 increases or decreases depending on a refraction angle of X-rays P2 in comparison with the dose of X-rays P1 incident on the X-ray detector 105. Accordingly, by performing various processes of calculating a difference between both images on the X-ray image A1 and the X-ray image A2, a small-angle X-ray scattered image based on the X-ray refraction information is generated. In this way, by capturing a plurality of X-ray images while relatively moving the sample mask 107 and the detection mask 109, it is possible to acquire a small-angle X-ray scattered image of a subject M.

CITATION LIST

Patent Document

Patent Document 1: JP-A-2011-45655
Patent Document 2: PCT International Publication No. 2013/014083

Non-Patent Document

Non-Patent Document 1: Low-dose phase contrast tomography with conventional x-ray sources C. K. Hagen et al., Medical Physics 41, 070701 (2014); doi: 10.1118/1.4884297

SUMMARY OF THE INVENTION

Technical Problem

However, in the conventional example having the above-mentioned configuration, there are following problems.

First, the conventional X-ray imaging device requires the detection mask 109 having an area corresponding to the X-ray detector 105. The detection mask 109 needs to have a configuration in which the X-ray absorbing materials R1 and the X-ray transmitting materials R2 are accurately arranged with a pitch of about several tens of μm, similarly to the sample mask 107. In order to enhance an X-ray absorption efficiency of the detection mask 109, the thickness of the X-ray absorbing materials R1 needs to be increased to absorb X-rays with high energy.

In general, an X-ray incident surface of the X-ray detector 105 has a large area of 40 cm square. That is, it is very difficult to prepare a configuration in which the X-ray absorbing materials R1 are thick and the X-ray absorbing materials R1 and the X-ray transmitting materials R2 are accurately repeatedly arranged with a pitch of several tens of μm in a large area of several tens of cm square. Accordingly, since the detection mask 109 with a large area is very expensive, the manufacturing cost of the X-ray imaging device increases.

When it is intended to accurately detect refraction of X-rays, the pixels 113 disposed in the X-ray detector 105 and the X-ray transmitting materials R2 disposed in the detection mask 109 need to have a positional relationship of one-to-one correspondence. Accordingly, it is necessary to align the detection mask 109 and the X-ray detector 105 with high accuracy. When the detection mask 109 and the sample mask 107 are relatively moved, it is necessary to move both masks in a state in which the positional relationship between the detection mask 109 and the X-ray detector 105 is maintained accurate. In this way, since a moving mechanism with high accuracy and the detection mask 109 and the X-ray detector 105 aligned with high accuracy are required, the manufacturing cost of the X-ray imaging device further increases.

When an X-ray imaging device is manufactured with high accuracy positioning, positional relationships of the X-ray tube 103, the sample mask 107, the detection mask 109, and the X-ray detector 105 may be changed due to vibration or the like at the time of utilizing the X-ray imaging device. When the positional relationships are changed, positions of X-ray images mirrored in the X-ray images A1 and A2 have errors and thus diagnosability of a small-angle X-ray scattered image is reduced as a result.

When a small-angle X-ray scattered image is generated in the conventional device, it is necessary to perform X-ray imaging a plurality of times while relatively moving the detection mask 109 and the sample mask 107. Accordingly, an exposure dose of a subject increases. When it is intended to improve X-ray sensitivity of the X-ray detector 105, it is necessary to form the scintillator layer 105a with a large thickness so as to detect X-rays of high energy. However, when the scintillator layer 105a is formed with a large thickness, scintillator light is easily scattered inside the scintillator layer 105a and there is a problem that a resolution of an X-ray image may decrease.

The present invention is made in consideration of the above-mentioned circumstances, and an object thereof is to provide an X-ray imaging device that can capture a small-angle X-ray scattered image with high diagnosability with a lower manufacturing cost.

Solution to Problem

The present invention has the following configuration to achieve the above-mentioned object.

That is, according to the present invention, there is provided an X-ray imaging device including: an X-ray tube that emits X-rays to a subject; a shielding mask which is disposed between the X-ray tube and the subject and in which X-ray transmitting portions extending in a first direction are arranged parallel in a second direction perpendicular to the first direction; an X-ray detector that detects X-rays transmitted by the X-ray transmitting portions and outputs an X-ray detection signal; a moving mechanism that moves a relative position of the X-ray detector and the shielding mask in the second direction; an X-ray emission control unit that performs control of causing the X-ray tube to repeatedly emit X-rays while the moving mechanism moves the relative position; an image generating unit that generates an X-ray image using the X-ray detection signal output from the X-ray detector every emission of X-rays from the X-ray tube; a refraction information calculating unit that calculates X-ray refraction information including a refraction direction and a refraction angle of X-rays based on the X-ray image generated by the image generating unit; and a scattered image reconstructing unit that reconstructs a small-angle X-ray scattered image mirroring an X-ray refraction contrast image of the subject based on the X-ray refraction information, in which the X-ray detector includes a scintillator layer including light-shielding walls in a lattice shape and scintillator elements that are disposed in cells which are defined in a two-dimensional matrix shape by the light-shielding walls and convert incident X-rays into light, and an output layer in which pixels that convert light converted by the scintillator elements into electric charges are arranged in a two-dimensional matrix shape.

[Operation/Effect] According to the X-ray imaging device according to the present invention, the scintillator layer of the X-ray detector has a configuration in which the scintillator elements are defined by the light-shielding walls in a lattice shape. In this case, among X-rays limited to a fan beam shape by the shielding mask, X-rays incident on parts in which the light-shielding walls are disposed are not detected and only X-rays incident on parts in which the scintillator elements are disposed are detected. Accordingly, a function of a detection mask that limits a part of X-rays transmitted by the shielding mask can be replaced by the light-shielding walls disposed in the scintillator layer.

As a result, when the detection mask which is a constituent essential to the conventional X-ray imaging device which is used for EI-XPCi is omitted, it is possible to acquire a small-angle X-ray scattered image by appropriately performing EI-XPCi. That is, since the detection mask which it is difficult to manufacture due to its large area is not necessary, it is possible to easily acquire a small-angle X-ray scattered image with a larger size by performing EI-XPCi on the X-ray detector with a large area.

Since it is not necessary to manufacture the detection mask with a large area with high accuracy, it is possible to reduce a manufacturing cost of the X-ray imaging device which is used for EI-XPCi. Since the detection mask and the X-ray detector do not need to be aligned with high accuracy, it is possible to more satisfactorily avoid a decrease in diagnosability of a small-angle X-ray scattered image due to positional deviation and to further reduce the manufacturing cost of the X-ray imaging device.

The present invention has the following configuration to achieve the above-mentioned object.

That is, according to the present invention, there is provided an X-ray imaging device including: an X-ray tube that emits X-rays to a subject; a shielding mask which is disposed between the X-ray tube and the subject and in which X-ray transmitting portions extending in a first direction are arranged parallel in a second direction perpendicular to the first direction; an X-ray detector that detects X-rays transmitted by the X-ray transmitting portions and outputs an X-ray detection signal; an image generating unit that generates an X-ray image using the X-ray detection signal output from the X-ray detector; a refraction information calculating unit that calculates X-ray refraction information including a refraction direction and a refraction angle of X-rays based on the X-ray image generated by the image generating unit; and a scattered image reconstructing unit that reconstructs a small-angle X-ray scattered image mirroring an X-ray refraction contrast image of the subject based on the X-ray refraction information, in which the X-ray detector includes a scintillator layer including light-shielding walls in a lattice shape and scintillator elements that are disposed in cells which are defined in a two-dimensional matrix shape by the light-shielding walls and convert incident X-rays into light, and an output layer in which pixels that convert light converted by the scintillator elements into electric charges are arranged in a two-dimensional matrix shape, and positions of the X-ray transmitting portions and the X-ray detector are set such that an area in which the X-rays are incident on the X-ray detector overlaps two or more scintillator elements in the second direction.

[Operation/Effect] According to the X-ray imaging device according to the present invention, in the shielding mask, the X-ray transmitting portions extending in the first direction are arranged in the second direction perpendicular to the first direction. The positions of the X-ray transmitting portions and the X-ray detector are set such that the area in which X-rays are incident on the X-ray detector overlap a part of each of the two or more scintillator elements in the second direction.

In this configuration, X-rays are limited to a fan beam shape extending in the first direction by the shielding mask and are incident on the two or more scintillator elements in the second direction. When X-rays are refracted in the second direction at the time of being transmitted by the subject, an incident area of X-rays is moved in the second direction. Accordingly, a difference between X-ray doses incident on two or more scintillator elements varies.

Accordingly, it is possible to calculate the refraction direction and the refraction angle of X-rays based on the variation in the difference between the X-ray doses incident on two or more scintillator elements. Since an X-ray dose incident on each scintillator element can be calculated based on a luminance value of a pixel in an X-ray image, the refraction information calculating unit can calculate refraction information including the refraction direction and the refraction angle of X-rays in the second direction by one time of X-ray emission.

The scattered image reconstructing unit reconstructs a small-angle X-ray scattered image in which an X-ray refraction contrast image of the subject is mirrored. Accordingly, the number of times of X-ray emission required for the small-angle X-ray scattered image is two or more in the conventional art, but is one in the X-ray imaging device according to the present invention. As a result, it is possible to reduce an X-ray dose to which a subject is exposed at the time of acquiring a small-angle X-ray scattered image and to shorten a time required for capturing the small-angle X-ray scattered image.

In the present invention, it is preferable that the X-ray detector include: a first scintillator array that includes the light-shielding walls in a lattice shape and first scintillator elements that are defined by the light-shielding walls and are arranged in the second direction; and a second scintillator array that includes the light-shielding walls in a lattice shape and second scintillator elements that are defined by the light-shielding walls and are arranged in the second direction and in which an arrangement pattern of the second scintillator elements is deviated by a predetermined distance in the second direction from an arrangement pattern of the first scintillator elements, and the first scintillator array and the second scintillator array be alternately arranged in the first direction.

[Operation/Effect] According to the X-ray imaging device according to the present invention, in the X-ray detector, the first scintillator array and the second scintillator array are alternately arranged in the first direction in the X-ray detector. The arrangement pattern of the first scintillator elements disposed in the first scintillator array and the arrangement pattern of the second scintillator elements disposed in the second scintillator array are deviated from each other by a predetermined distance in the second direction.

In this case, in an X-ray image generated by one time of X-ray emission, image information based on the first scintillator elements is X-ray image information which is acquired when an X-ray image is captured without moving the X-ray detector. On the other hand, image information based on the second scintillator elements is X-ray image information which is acquired when X-rays are emitted in a state in which the X-ray detector is moved by a predetermined distance in the second direction. Accordingly, it is possible to acquire two pieces of X-ray image information which are captured at two different imaging positions by one time of X-ray emission.

Since the refraction information calculating unit calculates the refraction information of X-rays based on two pieces of X-ray image information acquired by one time of X-ray emission, the number of times of X-ray emission which is required for a small-angle X-ray scattered image is only one. Accordingly, it is possible to reduce an X-ray dose to which a subject is exposed at the time of acquiring a small-angle X-ray scattered image and to shorten a time required for capturing the small-angle X-ray scattered image. The distance between imaging positions of the two pieces of X-ray image information can be calculated in advance based on the deviation of the arrangement patterns of the scintillator elements. Accordingly, it is possible to simplify a calculation process of calculating refraction information.

The present invention may have the following configuration to achieve the above-mentioned object.

That is, according to the present invention, there is provided an X-ray imaging device including: an X-ray tube that emits X-rays to a subject; a shielding mask which is disposed between the X-ray tube and the subject and in which X-ray transmitting portions are arranged in a two-dimensional matrix shape in two directions perpendicular to each other; an X-ray detector that detects X-rays transmitted by the X-ray transmitting portions and outputs an X-ray detection signal; an image generating unit that generates an X-ray image using the X-ray detection signal output from the X-ray detector; a refraction information calculating unit that calculates X-ray refraction information including a refraction direction and a refraction angle of X-rays based on the X-ray image generated by the image generating unit; and a scattered image reconstructing unit that reconstructs a small-angle X-ray scattered image mirroring an X-ray refraction contrast image of the subject based on the X-ray refraction information, in which the X-ray detector includes a scintillator layer including light-shielding walls in a lattice shape and scintillator elements that are disposed in cells which are defined in a two-dimensional matrix shape by the light-shielding walls and convert incident X-rays into light, and an output layer in which pixels that convert light converted by the scintillator elements into electric charges are arranged in a two-dimensional matrix shape, and positions of the X-ray transmitting portions and the X-ray detector are set such that an area in which the X-rays are incident on the X-ray detector overlaps two or more scintillator elements in the two directions perpendicular to each other.

[Operation/Effect] According to the X-ray imaging device according to the present invention, the X-ray transmitting portions are arranged in a two-dimensional matrix shape in two directions perpendicular to each other in the shielding mask. The positions of the X-ray transmitting portions and the X-ray detector are set such that the area in which X-rays are incident on the X-ray detector overlaps parts of the two or more scintillator elements in the two directions perpendicular to each other.

In this configuration, X-rays are limited to a pencil beam shape by the shielding mask and are incident on the two or more scintillator elements in the two directions perpendicular to each other. When X-rays are refracted in the second direction at the time of being transmitted by the subject, an incident area of X-rays is moved in the two directions perpendicular to each other. Accordingly, a difference between X-ray doses incident on two or more scintillator elements varies.

Accordingly, in the two directions perpendicular to each other, it is possible to calculate the refraction direction and the refraction angle of X-rays based on the variation in the difference between the X-ray doses incident on the scintillator elements. Since an X-ray dose incident on each scintillator element can be calculated based on a luminance value of a pixel in an X-ray image, the refraction information calculating unit can calculate refraction information including the refraction direction and the refraction angle of X-rays in the two directions perpendicular to each other by one time of X-ray emission.

The scattered image reconstructing unit reconstructs a small-angle X-ray scattered image in which an X-ray refraction contrast image of the subject is mirrored. Accordingly, the number of times of X-ray emission required for the small-angle X-ray scattered image is two or more in the conventional art, but is one in the X-ray imaging device according to the present invention. As a result, it is possible to reduce an X-ray dose to which a subject is exposed at the time of acquiring a small-angle X-ray scattered image and to shorten a time required for capturing the small-angle X-ray scattered image. The small-angle X-ray scattered image is an image based on the refraction information of X-rays in the two directions perpendicular to each other. Accordingly, in comparison with a small-angle X-ray scattered image based on the refraction information of X-rays in one direction, the refraction contrast image mirrored in the small-angle X-ray scattered image is more precise. Accordingly, it is possible to perform more accurate diagnosis using the small-angle X-ray scattered image.

In the above-mentioned invention, it is preferable that the positions of the X-ray transmitting portions and the X-ray detector be set such that an area in which the X-rays are incident on the X-ray detector circumscribes the two or more scintillator elements in the two directions perpendicular to each other.

[Operation/Effect] According to the X-ray imaging device according to the present invention, the area in which X-rays are incident on the X-ray detector circumscribes the two or more scintillator elements in the two directions perpendicular to each other. In this case, since X-rays are not incident on any of the scintillator elements when X-rays are not refracted, luminance values of all the pixels in an X-ray image are zero. On the other hand, since X-rays are incident on the scintillator element located on the side on which X-rays are refracted when X-rays are refracted, the luminance values of the pixels are predetermined values corresponding to incident X-ray doses.

The refraction information calculating unit can calculate the refraction information of X-rays in the two directions perpendicular to each other based on the luminance values of the pixels in the X-ray image. When X-rays are not refracted, the luminance values of all the pixels are zero and thus it is possible to simplify a calculation process which is performed to calculate the refraction information by the refraction information calculating unit. Accordingly, it is possible to further shorten the time required for acquiring a small-angle X-ray scattered image.

In the above-mentioned invention, it is preferable that the X-ray detector include: a first scintillator layer; a second scintillator layer; a first output layer in which pixels that convert light converted by the scintillator elements disposed in the first scintillator layer into electric charges are arranged in a two-dimensional matrix shape; and a second output layer in which pixels that convert light converted by the scintillator elements disposed in the second scintillator layer into electric charges are arranged in a two-dimensional matrix shape, and a lattice pattern of the light-shielding walls disposed in the first scintillator layer and a lattice pattern of the light-shielding walls disposed in the second scintillator layer be deviated along the X-ray incident surface.

[Operation/Effect] According to the X-ray imaging device according to the present invention, the lattice pattern of the light-shielding walls disposed in the first scintillator layer and the lattice pattern of the light-shielding walls disposed in the second scintillator layer are deviated along the X-ray incident surface. Accordingly, X-rays incident on the X-ray detector are satisfactorily incident on at least one of the first scintillator element and the second scintillator element and are converted into light. As a result, since an area in which X-rays cannot be detected in the X-ray detector can be greatly decreased, it is possible to greatly improve X-ray sensitivity of the X-ray detector.

In the above-mentioned invention, it is preferable that a ratio a pitch of the light-shielding walls disposed in the first scintillator layer and a pitch of the light-shielding walls disposed in the second scintillator layer be the same as a ratio of a spreading width when X-rays emitted from the X-ray tube reach the first scintillator layer and a spreading width when X-rays emitted from the X-ray tube reach the second scintillator layer.

[Operation/Effect] According to the X-ray imaging device according to the present invention, it is possible to provide an X-ray imaging device with high sensitivity in which X-rays spreading in a radial shape are not incident on the light-shielding walls as much as possible.

In the above-mentioned invention, it is preferable that the X-ray detector include: the scintillator layer; a scintillator panel that includes the scintillator elements; a first output layer in which pixels that convert light converted by the scintillator elements disposed in the scintillator layer into electric charges are arranged in a two-dimensional matrix shape; and a second output layer in which pixels that convert light converted by the scintillator elements disposed in the scintillator panel into electric charges are arranged in a two-dimensional matrix shape, and the scintillator layer and the scintillator panel be stacked in an incidence direction of the X-rays.

[Operation/Effect] According to the X-ray imaging device according to the present invention, the X-ray detector includes the scintillator layer in which the scintillator elements are defined by the light-shielding walls in a lattice shape. Accordingly, since a function of the detection mask that limits a part of X-rays transmitted by the shielding mask can be replaced by the light-shielding walls disposed in the scintillator layer. Accordingly, even when the detection mask which is essential to the conventional X-ray imaging device is omitted, it is possible to acquire a small-angle X-ray scattered image by performing EI-XPCi. Since the scintillator layer is stacked on the scintillator panel in the incidence direction of X-rays, it is possible to obtain the same effects as a dual energy type X-ray detector as a whole of the X-ray detector.

In the above-mentioned invention, it is preferable that a pitch of the pixels disposed in the scintillator panel be larger than a pitch of the pixels disposed in the scintillator layer.

[Operation/Effect] According to the X-ray imaging device according to the present invention, the pitch of the pixels disposed in the scintillator panel is larger than the pitch of the pixels disposed in the scintillator layer. Accordingly, it is possible to acquire more accurate image information including small-angle X-ray scattering information based on the first output layer. On the other hand, since the pitch of the pixels disposed in the scintillator panel is relatively large, it is possible to avoid elongation of a processing time due to a lot of amount of information in the scintillator panel. As a result, since the time required for acquiring an X-ray image can be shortened and the configuration of the X-ray detector can be further simplified, it is possible to further decrease the cost required for manufacturing the device.

In the above-mentioned invention, it is preferable that photoelectric conversion elements disposed in the pixels be located in compartments which are formed by the lattice of the light-shielding walls.

[Operation/Effect] According to the X-ray imaging device according to the present invention, neighboring photoelectric conversion elements can be optically isolated from each other more satisfactorily.

In the above-mentioned invention, it is preferable that the light-shielding walls be configured to be gradually inclined from a center of the X-ray detector to an end thereof.

[Operation/Effect] According to the X-ray imaging device according to the present invention, it is possible to provide an X-ray imaging device with high accuracy in which X-rays spreading in a radial shape are not incident on two or more pixels as much as possible.

In the above-mentioned invention, it is preferable that the X-ray transmitting portions and the X-ray detector be configured such that a magnitude of an area in which the area in which the X-rays are incident on the X-ray detector overlaps the scintillator elements extending in the first direction varies periodically for each of the scintillator elements arranged in the second direction.

[Operation/Effect] According to the X-ray imaging device according to the present invention, by calculating a periodic variation of the magnitude of the overlapping area, it is possible to accurately detect a relative position deviation of the shielding mask and the X-ray detector and to correct an influence which the relative position deviation has on an X-ray image. Accordingly, it is possible to more rapidly correct an influence which the relative position deviation has on an X-ray image and to acquire an X-ray image with high accuracy.

In the above-mentioned invention, it is preferable that the positions of the X-ray transmitting portions and the X-ray detector be set such that the area in which the X-rays are incident on the X-ray detector circumscribes two or more scintillator elements in the second direction.

[Operation/Effect] According to the X-ray imaging device according to the present invention, since X-rays are not incident on any of the scintillator elements when X-rays are not refracted, luminance values of all the pixels in an X-ray image are zero. On the other hand, since X-rays are incident on the scintillator element located on the side on which X-rays are refracted when X-rays are refracted, the luminance values of the pixels are predetermined values corresponding to incident X-ray doses. Accordingly, since a calculation process which is performed to calculate the refraction information by the refraction information calculating unit can be further simplified, it is possible to further shorten the time required for acquiring a small-angle X-ray scattered image.

In the above-mentioned invention, it is preferable that the positions of the X-ray transmitting portions and the X-ray detector be set such that the area in which the X-rays are incident on the X-ray detector circumscribes two or more light-shielding walls in the second direction.

[Operation/Effect] According to the X-ray imaging device according to the present invention, X-rays are not incident on any of the light-shielding walls when X-rays are not refracted. On the other hand, since X-rays are incident on the light-shielding wall located on the side on which X-rays are refracted when X-rays are refracted, the luminance values of the pixels are predetermined values corresponding to incident X-ray doses. Accordingly, since a calculation process which is performed to calculate the refraction information by the refraction information calculating unit can be further simplified, it is possible to further shorten the time required for acquiring a small-angle X-ray scattered image.

Advantageous Effects of the Invention

According to the X-ray imaging device according to the present invention, the scintillator layer of the X-ray detector has a configuration in which the scintillator elements are defined by the light-shielding walls in a lattice shape. In this case, among X-rays limited to a fan beam shape by the shielding mask, X-rays incident on parts in which the light-shielding walls are disposed are not detected and only X-rays incident on parts in which the scintillator elements are disposed are detected. Accordingly, a function of a detection mask that limits a part of X-rays transmitted by the shielding mask can be replaced by the light-shielding walls disposed in the scintillator layer.

As a result, when the detection mask which is a constituent essential to the conventional X-ray imaging device which is used for EI-XPCi is omitted, it is possible to acquire a small-angle X-ray scattered image by appropriately performing EI-XPCi. That is, since the detection mask which it is difficult to manufacture due to its large area is not necessary, it is possible to easily acquire a small-angle X-ray scattered image with a larger size by performing EI-XPCi on the X-ray detector with a large area.

Since it is not necessary to manufacture the detection mask with a large area with high accuracy, it is possible to reduce a manufacturing cost of the X-ray imaging device which is used for EI-XPCi. Since the detection mask and the X-ray detector do not need to be aligned with high accuracy, it is possible to more satisfactorily avoid a decrease in diagnosability of a small-angle X-ray scattered image due to positional deviation and to further reduce the manufacturing cost of the X-ray imaging device.

BRIEF DESCRIPTION OF THE DRAWINGS

FIG. 1 is a diagram illustrating a configuration of an X-ray imaging device according to a first embodiment which is used for EI-XPCi, where FIG. 1(a) is a diagram schematically illustrating an entire configuration of the X-ray imaging device and FIG. 1(b) is a diagram illustrating a configuration of a sample mask.

FIG. 2 is a diagram illustrating a configuration of an X-ray detector according to the first embodiment, where FIG. 2(a) is a cross-sectional view of the X-ray detector and FIG. 2(b) is a plan view of the X-ray detector.

FIG. 3 is a diagram illustrating a positional relationship between a sample mask and an X-ray detector according to the first embodiment, where FIG. 3(a) is a cross-sectional view illustrating an irradiation area of X-rays when X-rays are emitted in a state in which there is no subject and FIG. 3(b) is a plan view of the X-ray detector illustrating an irradiation area of X-rays when X-rays are emitted in a state in which there is no subject.

FIG. 4 is a diagram illustrating an operation of the X-ray detector according to the first embodiment, where FIG. 4(a) is a cross-sectional view illustrating an irradiation area of X-rays when X-rays are emitted in a state in which there is a subject, FIG. 4(b) is a diagram illustrating an irradiation area of X-rays on an X-ray incident surface of the X-ray detector when X-rays are emitted in a state in which there is a subject, FIG. 4(c) is a cross-sectional view illustrating an irradiation area of X-rays when X-rays are emitted after the X-ray detector is moved, and FIG. 4(d) is a diagram illustrating an irradiation area of X-rays on the X-ray incident surface of the X-ray detector when X-rays are emitted after the X-ray detector is moved.

FIG. 5 is a diagram illustrating advantages of the X-ray imaging device according to the first embodiment, where FIG. 5(a) is a cross-sectional view of the X-ray imaging device according to the first embodiment, FIG. 5(b) is a cross-sectional view illustrating configuration of an X-ray imaging device according to a conventional example which corresponds to the X-ray detector according to the first embodiment, and FIG. 5(c) is a diagram illustrating an incident area of X-rays which is limited by shielding walls of the X-ray detector according to the first embodiment or a detection mask according to the conventional example.

FIG. 6 is a diagram illustrating a configuration of an X-ray detector according to a second embodiment, where FIG. 6(a) is an overhead view of a scintillator array and FIG. 6(b) is a plan view of the X-ray detector.

FIG. 7 is a diagram illustrating an operation of the X-ray detector according to the second embodiment, where FIG. 7(a) is a cross-sectional view illustrating an irradiation area of X-rays in a scintillator array 23A, FIG. 7(b) is a cross-sectional view illustrating an irradiation area of X-rays in the scintillator array 23B, and FIG. 7(c) is a diagram illustrating an irradiation area of X-rays on an X-ray incident surface of the X-ray detector.

FIG. 8 is a diagram illustrating a configuration of an X-ray imaging device according to a third embodiment, where FIG. 8(a) is a diagram schematically illustrating an entire configuration of the X-ray imaging device, FIG. 8(b) is a diagram illustrating a configuration of a sample mask, and FIG. 8(c) is a diagram illustrating another example of the sample mask.

FIG. 9 is a diagram illustrating a configuration of an X-ray detector according to the third embodiment, where FIG. 9(a) is a plan view of a scintillator layer, FIG. 9(b) is a plan view of an output layer, FIG. 9(c) is a view of an A-A cross-section illustrating a positional relationship between the sample mask and the X-ray detector, and FIG. 9(d) is a diagram illustrating a positional relationship between an irradiation area of X-rays and scintillator elements on an X-ray incident surface of the X-ray detector.

FIG. 10 is a diagram illustrating a positional relationship between an irradiation area of X-rays and scintillator elements on an X-ray incident surface of the X-ray detector according to the third embodiment, where FIG. 10(a) is a diagram illustrating the positional relationship when X-rays are not refracted, FIG. 10(b) is a diagram illustrating the positional relationship when X-rays are refracted in an x direction, FIG. 10(c) is a diagram illustrating the positional relationship when X-rays are refracted in a y direction, and FIG. 10(d) is a diagram illustrating the positional relationship when X-rays are refracted in the x direction and the y direction.

FIG. 11 is a diagram illustrating an example in which a relative position of the sample mask and the X-ray detector is deviated, where FIG. 11(a) is a diagram illustrating a state in which the X-ray detector moves parallel to the X-ray incident surface and FIG. 11(b) is a diagram illustrating a state in which the X-ray detector moves rotationally along the X-ray incident surface.

FIG. 12 is a diagram illustrating a position of a unit which is used to correct relative position deviation in an X-ray detector according to a fourth embodiment.

FIG. 13 is a diagram illustrating a positional relationship between an irradiation area of X-rays and scintillator elements on an X-ray incident surface of the X-ray detector according to the fourth embodiment, where FIG. 13(a) is a diagram illustrating the positional relationship when the X-ray detector moves parallel to the X-ray incident surface and FIG. 13(b) is a diagram illustrating the positional relationship when the X-ray detector moves rotationally along the X-ray incident surface.

FIG. 14 is a diagram illustrating an X-ray imaging device according to a modified example of the second embodiment, where FIG. 14(a) is a diagram illustrating a positional relationship between an irradiation area of X-rays and scintillator elements on an X-ray incident surface of an X-ray detector and FIG. 14(b) is a diagram of an A-A cross-section illustrating the irradiation area of X-rays.

FIG. 15 is a diagram illustrating an X-ray imaging device according to a modified example, where FIG. 15(a) is a diagram illustrating a shape of a scintillator element according to a modified example of the third embodiment, FIG. 15(b) is a diagram illustrating a positional relationship between an irradiation area of X-rays and a scintillator element on an X-ray incident surface of an X-ray detector when X-rays are not refracted according to the modified example of the third embodiment, FIG. 15(c) is a diagram illustrating a positional relationship between an irradiation area of X-rays and a scintillator element on the X-ray incident surface of the X-ray detector when X-rays are refracted according to the modified example of the third embodiment, FIG. 15(d) is a diagram illustrating a positional relationship between an irradiation area of X-rays and a scintillator element on the X-ray incident surface of the X-ray detector when X-rays are not refracted according to a modified example of the second embodiment, and FIG. 15(e) is a diagram illustrating a positional relationship between an irradiation area of X-rays and a scintillator element on the X-ray incident surface of the X-ray detector when X-rays are refracted according to the modified example of the second embodiment.

FIG. 16 is a diagram illustrating an X-ray imaging device according to a modified example, where FIG. 16(a) is a diagram illustrating a state in which an X-ray detector has a two-layered structure and FIG. 16(b) is a diagram illustrating a state in which the X-ray detector has a single-layered structure.

FIG. 17 is a diagram illustrating a state in which X-rays transmitted by a subject M are refracted.

FIG. 18 is a diagram illustrating a diagram illustrating a configuration of an X-ray imaging device according to a conventional example which is used for EI-XPCi, where FIG. 18(a) is a diagram illustrating an entire configuration of the X-ray imaging device and FIG. 18(b) is a diagram illustrating a configuration of a sample mask.

FIG. 19 is a diagram illustrating the configuration of the X-ray imaging device according to the conventional example, where FIG. 19(a) is a cross-sectional view of an X-ray detector which is used for EI-XPCi, FIG. 19(b) is a cross-sectional view illustrating an irradiation area of X-rays when X-rays are emitted in a state in which the X-ray detector is located at an initial position, and FIG. 19(c) is a cross-sectional view illustrating an irradiation area of X-rays when X-rays are emitted after the X-ray detector is moved from the initial position.

FIG. 20 is a diagram illustrating a configuration of an X-ray detector according to a modified example, where FIG. 20(a) is a cross-sectional view illustrating a configuration of an X-ray detector according to Modified Example (9) and FIG. 20(b) is a cross-sectional view illustrating a configuration of an X-ray detector according to Modified Example (10).

FIG. 21 is a diagram illustrating a configuration of an X-ray detector according to Modified Example (11), where FIG. 21(a) is a diagram illustrating a positional relationship between an irradiation area of X-rays and scintillator elements on an X-ray incident surface of the X-ray detector and FIG. 21(b) is a cross-sectional view illustrating the configuration of the X-ray detector.

FIG. 22 is a diagram illustrating an effect of an X-ray detector according to Modified Example (12), where FIG. 22(a) is a diagram illustrating a positional relationship between an irradiation area of X-rays and scintillator elements on an X-ray incident surface of the X-ray detector, FIG. 22(b) is a cross-sectional view illustrating the configuration of the X-ray detector according to Modified Example (11), and FIG. 22(c) is a cross-sectional view illustrating an effect of the X-ray detector according to Modified Example (12).

FIG. 23 is a diagram illustrating a configuration of an X-ray detector according to Modified Example (13), where FIG. 23(a) is a diagram illustrating a positional relationship between an irradiation area of X-rays and scintillator elements on an X-ray incident surface of the X-ray detector and FIG. 23(b) is a cross-sectional view illustrating the configuration of the X-ray detector.

FIG. 24 is a diagram illustrating a configuration of an X-ray detector according to Modified Example (14), where FIG. 24(a) is a diagram illustrating a positional relationship between an irradiation area of X-rays and scintillator elements on an X-ray incident surface of the X-ray detector and FIG. 24(b) is a cross-sectional view taken along a B-B arrow in FIG. 24(a).

FIG. 25 is a diagram illustrating a configuration of an X-ray detector according to Modified Example (15), where FIG. 25(a) is a diagram illustrating a positional relationship between an irradiation area of X-rays and scintillator elements on an X-ray incident surface of the X-ray detector, FIG. 25(b) is an enlarged view of a part indicated by reference sign Q in FIG. 25(a), and FIG. 25(c) is a diagram illustrating an effect of detecting a deviation in a rotation direction.

FIG. 26 is a diagram illustrating a configuration of an X-ray detector according to Modified Example (16).

FIG. 27 is a diagram illustrating a configuration of an X-ray detector according to Modified Example (17).

FIG. 28 is a diagram illustrating a configuration of an X-ray detector according to Modified Example (18).

MODE FOR CARRYING OUT THE INVENTION

[First Embodiment]

Hereinafter, a first embodiment of the present invention will be described with reference to the accompanying drawings. FIG. 1(a) is a diagram schematically illustrating an entire configuration of an X-ray imaging device according to the first embodiment which can be used for EI-XPCi.

<Description of the Entire Configuration>

An X-ray imaging device 1 according to the first embodiment includes an X-ray tube 3 that emits X-rays 3a to a subject M, an X-ray detector 5 that detects the X-rays 3a and outputs an X-ray detection signal, a moving mechanism 6, a sample mask 7, an image generating unit 8, a refraction information calculating unit 9, and a scattered image reconstructing unit 10. The subject M is placed on a mount stage which is not illustrated and the mount stage is configured to be rotatable, for example, about an axis parallel to the y direction. That is, the mount stage is configured such that the subject M can be appropriately rotated to irradiate an arbitrary surface of the subject M with X-rays by rotating the mount stage. The X-ray imaging device 1 according to the first embodiment is characterized in that the detection mask is omitted, unlike the conventional X-ray imaging device in which the detection mask is essential.

The moving mechanism 6 is connected to the X-ray detector 5 and relatively displaces a positional relationship between the X-ray detector 5 and the sample mask 7 by moving the X-ray detector 5 in the x direction. An X-ray emission control unit which is not illustrated is connected to the X-ray tube 3, and the X-ray emission control unit controls a timing at which X-rays 3a are emitted from the X-ray tube 3, a dose of the X-rays 3a, and the like. By causing the X-ray emission control unit to emit X-rays 3a at an appropriate timing while the moving mechanism 6 displaces the relative position between the X-ray detector 5 and the sample mask 7, it is possible to capture a plurality of X-ray images.

The image generating unit 8 is disposed in a rear stage of the X-ray detector 5 and generates an X-ray image of the subject M based on the X-ray detection signal output from the X-ray detector 5. The refraction information calculating unit 9 is disposed in a rear stage of the image generating unit 8 and calculates refraction information on X-rays 3a based on luminance values of pixels in the X-ray image. Refraction information is, for example, information on a refraction direction of X-rays 3a or a magnitude of a refraction angle of X-rays 3a. The scattered image reconstructing unit 10 reconstructs a small-angle X-ray scattered image in which a refraction contrast image of the subject M is mirrored based on the refraction information of the X-rays 3a.

The sample mask 7 is disposed between the subject M and the X-ray tube 3 and is disposed such that a direction (a z direction) along a center axis 3b of X-rays 3a emitted from the X-ray tube 3 is perpendicular to an X-ray incident surface of the sample mask 7. The sample mask 7 has a configuration in which X-ray absorbing materials R1 extending in the y direction and absorbing X-rays and X-ray transmitting materials R2 extending in the y direction and transmitting X-rays are alternately arranged parallel to each other in the x direction as illustrated in FIG. 1(b). A pitch (a period) of the X-ray absorbing materials R1 is defined as G and the length in the x direction of the X-ray transmitting materials R2 is defined as N.

That is, a plurality of slits extending in the y direction and transmitting X-rays are formed in the sample mask 7 by the X-ray transmitting materials R2. By causing the sample mask 7 to transmit X-rays 3a, X-rays 3a are limited to a shape in which a plurality of fan beams extending in the y direction and having a length of N in the x direction are connected in the y direction. A metal having a high X-ray absorption factor such as gold or platinum is used as a constituent material of the X-ray absorbing materials R1. A resin having a low X-ray absorption factor or the like can be used as the X-ray transmitting materials R2. It is preferable that the X-ray absorbing materials R1 and the X-ray transmitting materials R2 have substantially the same length in the x direction. The X-ray transmitting materials R2 may be openings. The sample mask 7 corresponds to the shielding mask in the present invention and the X-ray transmitting materials R2 correspond to the X-ray transmitting portions in the present invention.

The X-ray detector 5 is disposed such that an X-ray detection surface thereof is perpendicular to the z direction. In the first embodiment, an indirect conversion type flat panel detector (FPD) is used as the X-ray detector 5. As illustrated in FIG. 2(a), the X-ray detector 5 has a configuration in which a scintillator layer 11 and an output layer 13 are stacked. The scintillator layer 11 has a shape in which a plurality of scintillator elements 15 arranged in a two-dimensional matrix shape are partitioned by light-shielding walls 17 in a lattice shape. That is, the X-ray detector 5 has a configuration in which the scintillator elements 15 are defined by the light-shielding walls 17 in a lattice shape (see Reference Document 1: PCT International Publication No. 2012/161304).

Each of the scintillator elements 15 absorbs X-rays applied thereto and emits light such as fluorescent light as scintillator light in response to X-rays applied thereto. An example of a constituent material of the scintillator elements 15 is an X-ray fluorescent substance such as cesium triiodide. Glass powder containing alkali metal oxide or the like is used as the material of the light-shielding walls 17. Details of the material of the scintillator elements 15, the material of the light-shielding walls 17, and a process of forming the light-shielding walls 17 in the output layer 13 are described in Reference Document 1 or the like and description thereof will not be repeated herein.

The output layer 13 includes a substrate 19 and pixels 21 which are arranged in a two-dimensional matrix shape. Each of the pixels 21 includes a photoelectric conversion element that converts light into electric charges and an output element that outputs an X-ray detection signal based on the converted electric charges, converts scintillator light emitted from the corresponding scintillator element 15 into an X-ray detection signal, and outputs the X-ray detection signal. The image generating unit 8 is connected to the pixels 21 and generates an X-ray image of the subject M by performing various image processes on the X-ray detection signals output from the pixels 21.

As illustrated in FIG. 2(a), the pixels 21 are arranged with a positional relationship of one-to-one correspondence with the scintillator elements 15 partitioned by the light-shielding walls 17 respectively. That is, the pitch (period) of the pixels 21 is substantially the same as the pitch of the scintillator elements 15.

In this way, the scintillator layer 11 has a configuration in which the scintillator elements 15 are disposed in cells partitioned by the light-shielding walls 17 in a lattice shape. By employing this configuration, scattered scintillator light is intercepted by the light-shielding walls 17 even when scintillator light emitted from the scintillator elements 15 is scattered in the scintillator layer 11.

Accordingly, it is possible to prevent scattered light generated from the scintillator elements 15 from reaching neighboring scintillator elements 15. Accordingly, by partitioning the scintillator elements 15 by the light-shielding walls 17, it is possible to avoid a decrease in resolution of an X-ray image even when the light-shielding walls 17 are formed with a large thickness in the z direction in order to improve X-ray sensitivity of the X-ray detector 5.

In the X-ray detector 5 according to the first embodiment, the pitch of the light-shielding walls 17 can be set to a short distance of about 60 μm to 100 μm. Accordingly, by employing the X-ray detector 5, it is possible to avoid a decrease in resolution of an X-ray image even when a finer X-ray image is required.

By partitioning the scintillator elements 15 by the light-shielding walls 17 in the X-ray detector 5, the detection mask may be omitted to perform suitable EI-XPCi in the X-ray imaging device according to the first embodiment, though the detection mask is essential to the conventional X-ray imaging device which is used for EI-XPCi. Details of the effect due to omission of the detection mask will be described later.

In the X-ray imaging device 1, the X-ray tube 3, the X-ray detector 5, and the sample mask 7 can be constructed as follows.

Distance D1 from a focal point of the X-ray tube 3 to the sample mask 7: 1.6 m

Distance D2 from the sample mask 7 to the X-ray incidence surface of the X-ray detector 5: 0.4 m Distance D3 from the sample mask 7 to the subject M: 5 cm Pitch G (slit period) of the X-ray absorbing materials R1 in the sample mask 7: 66.8 μm Length N in the x direction of the X-ray transmitting materials R2 in the sample mask 7: 33.4 μm (G/2)

Pitch T of the scintillator elements 15 in the X-ray detector 5: 83.5 μm

Length B in the x direction of the scintillator elements 15 in the X-ray detector 5: 41.75 μm (T/2)

By employing the above-mentioned configuration, the length in the x direction of X-rays transmitted by the X-ray transmitting materials R2 of the sample mask 7 is the same as the length B in the x direction of the scintillator elements 15 when X-rays are incident on the X-ray detector 5. The distances D1 to D3 can be appropriately changed. In this case, the pitch P and the pitch T are changed depending on the values of the distances D1 to D3.

Regarding initial positions of the X-ray detector 5 and the sample mask 7, the initial positions are aligned in advance such that X-rays 3a are evenly incident on the scintillator elements 15 and the light-shielding walls 17 when the X-rays 3a are emitted in a state in which the subject M is not present (FIG. 3(a)). A ratio of the length in the x direction of the X-ray transmitting materials R2 and the length in the x direction of the scintillator elements 15 is the same as the ratio of the distance D1 and the distance D2. The X-ray transmitting materials R2 extend in the x direction. Accordingly, when X-rays are emitted in a state in which the subject M is not present, an area H in which X-rays 3a are incident on the X-ray detector 5 is a rectangular area extending in the x direction (FIG. 3(b)).

Accordingly, when X-rays are not refracted, the X-rays 3a are incident on an area corresponding to a right half (or a left half) of each of the scintillator elements 15 as illustrated in FIG. 3(b). In the first embodiment, it is assumed that the X-ray detector 5 and the sample mask 7 are aligned such that the X-rays 3a which are not refracted and incident on the X-ray detector 5 are incident on the area corresponding to the right half of each of the scintillator elements 15.

X-rays which are not incident on the scintillator elements 15 are incident on the light-shielding walls 17, are not converted into light, and are transmitted by the X-ray detector 5. As a result, the dose of X-rays incident on the scintillator elements 15 is limited by the length in the x direction of the light-shielding walls 17. Accordingly, since the light-shielding walls 17 exhibits the same function as the X-ray absorbing materials disposed in the detection mask by partitioning the scintillator layer 11 by the light-shielding walls 17, it is possible to omit the detection mask in the X-ray imaging device 1 according to the first embodiment.

<X-Ray Imaging Process in the First Embodiment>

A process of performing X-ray imaging using EI-XPCi using the X-ray imaging device 1 according to the first embodiment will be described below. In a process outline of EI-XPCi, first, an X-ray image A1 is captured in a state in which the X-ray detector 5 and the sample mask 7 are located at predetermined initial positions (Step S1). Then, the X-ray detector 5 is moved by a distance C in the x direction and an X-ray image A2 is captured (Step S2). Then, refraction information of X-rays 3a is calculated based on the luminance values of the pixels 21 in the X-ray images A1 and A2 (Step S3). Finally, a small-angle X-ray scattered image in which an X-ray refraction contrast image of the subject M is mirrored is reconstructed based on the refraction information (Step S4). Details of the processes will be described below.

In performing the process of Step S1, first, a subject M is placed on a mount table. X-rays 3a are emitted to the subject M from the X-ray tube 3 such that the X-ray image A1 is captured at the initial position. The X-rays 3a are transmitted by an area of the X-ray transmitting materials R2 disposed in the sample mask 7 and are incident on the X-ray detector 5 in a state in which the X-rays are limited by a fan beam extending in the y direction.

As illustrated in FIG. 4(a), among the X-rays 3a transmitted by the X-ray transmitting materials R2, X-rays P1 which are not transmitted by the subject M are not refracted and incident on the X-ray detector 5. The area in which X-rays P1 are incident on the X-ray detector 5 is indicted by reference sign H1 in FIG. 4(b). Since X-rays P1 are not refracted, the area Ea in which the X-rays P1 are incident on the scintillator elements 15a (the scintillator elements 15 on which the X-rays P1 are incident) corresponds to the right half of each of the scintillator elements 15a.

Accordingly, the area H1 overlaps an area corresponding to the right half of each of the scintillator elements 15a. That is, the left end of the area H1 matches the center line in the x direction of each of the scintillator elements 15a. As a result, an X-ray dose corresponding to half the X-rays P1 is incident on each of the scintillator elements 15a and is converted into scintillator light W. The scintillator light W is photoelectrically converted in the pixels 21a (the pixels 21 bordering the scintillator elements 15a) and is output as an X-ray detection signal which is an electronic signal.

On the other hand, among X-rays 3a transmitted by the X-ray transmitting materials R2, most of X-rays P2 transmitted by the subject M are refracted depending on the shape of the subject M or the like. That is, as illustrated in FIG. 4(a), among the X-rays P2, x-rays P2a are refracted to the left in the x direction and X-rays P2b are refracted to the right. Accordingly, an area H2a on which the X-rays P2a are incident on the X-ray incidence surface is displaced to the left in the x direction by a distance corresponding to reference sign Ja in comparison with the area H1. An area H2b on which the X-rays P2b are incident are displaced to the right in the x direction by a distance corresponding to reference sign Jb in comparison with the area H1.

As a result, a dose of X-rays which are incident on each of the scintillator elements 15 increases or decreases depending on the refraction angle of X-rays. At the time of capturing an X-ray image A1, an area Eb on which the X-rays P2a are incident on each of the scintillator elements 15b (the scintillator elements 15 on which the X-rays P2a are incident) is widened depending on a refraction distance Ja of the X-rays P2a. That is, a dose of X-rays incident on each of the scintillator elements 15b increases depending on the refraction distance Ja of the X-rays P2a. Accordingly, the X-ray detection signal output from a pixel 21b (the pixel 21 bordering each of the scintillator elements 15b) increases in intensity depending on the refraction distance Ja.

At the time of capturing an X-ray image A1, an area Ec on which X-rays P2b are incident on the scintillator elements 15c (the scintillator elements 15 on which the X-rays P2b are incident) is narrowed depending on a refraction distance Jb of the X-rays P2b. That is, the X-ray dose incident on the scintillator elements 15c decreases depending on the refraction distance Jb of the X-rays P2b. Accordingly, the X-ray detection signals output from the pixels 21c (the pixels 21 bordering the scintillator elements 15c) decrease in intensity depending on the refraction distance Jb. The image generating unit performs various image processes on the X-ray detection signals output from the pixels 21a to 21c and generates an X-ray image A1.

After the X-ray image A1 is captured, the process of Step S2 is performed. That is, the X-ray detector 5 is moved by a distance indicated by reference sign C in FIG. 4(c) in the x direction from the initial position such that the positional relationship between the X-ray detector 5 and the sample mask 7 is displaced. Similarly to the length B in the x direction of the scintillator elements 15, it is preferable that the distance C be half the pitch T of the scintillator elements 15. The present invention is not limited to the configuration for moving the X-ray detector 5 and the sample mask 7 may be moved in the x direction. In the first embodiment, it is assumed that the X-ray detector 5 is moved by a distance of (T/2) in the x direction.

After the X-ray detector 5 is moved in the x direction, X-rays 3a are applied to the subject M from the X-ray tube 3 to capture an X-ray image A2. The X-rays 3a are transmitted by the area of the X-ray transmitting materials R2 disposed in the sample mask 7 and are incident on the X-ray detector 5.

As illustrated in FIG. 4(c), among the X-rays 3a transmitted by the X-ray transmitting materials R2, X-rays P1 not transmitted by the subject M are not refracted and are incident on the X-ray detector 5. Since the X-ray detector 5 is moved by a distance of (T/2) in the x direction, an area Ea on which the X-rays P1 are incident on each of the scintillator elements 15a corresponds to an area of the left half of each of the scintillator elements 15a as illustrated in FIG. 4(d). As a result, a dose of X-rays corresponding to half the X-rays P1 is incident on each of the scintillator elements 15a, and is converted into scintillator light W. Since the area of the area Ea is not changed due to movement of the X-ray detector 5, the intensity of the X-ray detection signal output each of the scintillator elements 15a is not changed between at the time of capturing the X-ray image A1 and at the time of capturing the X-ray image A2.

However, in each of the scintillator elements 15b and the scintillator elements 15c on which the refracted X-rays P2 are incident, an incidence dose of X-rays is changed due to movement of the X-ray detector 5. By moving the X-ray detector 5 by a distance of (T/2) in the x direction, an area Eb on which X-rays P2a are incident on each of the scintillator elements 15b at the time of capturing the X-ray image A2 is narrowed by a distance Ja in comparison with the area Ea (FIG. 4(d)). That is, the scintillator light W emitted from the scintillator elements 15b is weakened depending on the refraction distance Ja. Accordingly, the X-ray detection signals output from the pixels 21b decrease in intensity depending on the refraction distance Ja.

On the other hand, by moving the X-ray detector 5 by a distance of (T/2) in the x direction, an area Ec on which X-rays P2b are incident on each of the scintillator elements 15c at the time of capturing the X-ray image A2 is widened by a distance Jb in comparison with the area Ea (FIG. 4(d)). The scintillator light W emitted from the scintillator elements 15c is strengthened depending on the refraction distance Jb. Accordingly, the X-ray detection signals output from the pixels 21c increase in intensity depending on the refraction distance Jb. The image generating unit 8 performs various image processes on the X-ray detection signals output from the pixels 21a to 21c and generates the X-ray image A2.

In this way, after the X-ray image A1 is captured, the relative position of the X-ray detector 5 and the sample mask 7 is displaced and then the X-ray image A2 is further captured. After the X-ray images A1 and A2 are captured, the process of Step S3 is performed. In Step S3, first, information of the X-ray images A1 and A2 is transmitted to the refraction information calculating unit 9. The refraction information calculating unit 9 calculates refraction information of X-rays 3a based on two pieces of X-ray image information. As a technique of calculating the refraction information of X-rays 3a, a method of calculating a difference between the two captured X-ray images and generating an X-ray image A3 and the like can be used.

As described above, when X-rays incident on the scintillator elements 15 are not refracted, the intensities of the X-ray detection signals output from the pixels 21 are the same at the times of capturing the X-ray images A1 and A2. Accordingly, in the X-ray image A3, the luminance value of a pixel 21a on which non-refracted X-rays are incident is zero.

On the other hand, when X-rays incident on the scintillator elements 15 are refracted due to transmission by the subject M, the intensities of the X-ray detection signals output from the pixels 21 are different in the X-ray images A1 and A2. That is, the luminance value of the pixel 21b in the X-ray image A1 is larger than the luminance value of the pixel 21b in the X-ray image A2, and the luminance value of the pixel 21c in the X-ray image A1 is smaller than the luminance value of the pixel 21c in the X-ray image A2.

Accordingly, information on the refraction direction of X-rays can be acquired depending on the sign of the luminance value in the X-ray image A3. The refraction distances Ja and Jb of X-rays 3a can be calculated based on the absolute values of the luminance values of the pixel 21b and the pixel 21c in the X-ray image A3. The magnitude of the refraction angle of the X-rays 3a can be calculated based on the refraction distances Ja and Jb. In this way, the refraction information calculating unit 9 calculates information on the refraction direction and the refraction angle as refraction information for the X-rays 3a incident on the pixels 21 based on the luminance values of the pixels 21 in the X-ray image A3.

By calculating the refraction information, the process of Step S4 is performed. In Step S4, the refraction information is transmitted from the refraction information calculating unit 9 to the scattered image reconstructing unit 10. The scattered image reconstructing unit 10 reconstructs a small-angle X-ray scattered image of the subject M based on the refraction information. The small-angle X-ray scattered image mirrors the refraction information of X-rays 3a due to transmission by the subject M as a refraction contrast image. Since the X-ray refraction effect is much larger than the X-ray absorption effect, it is possible to acquire an image with a high contrast and high diagnosability even when the subject is a soft tissue including much moisture such as a cartilage.

An amount of X-rays absorbed by the subject M can be calculated based on an average of the luminance values in the X-ray image A1 and the luminance values in the X-ray image A2. A dose of X-rays not transmitted by the subject M is calculated by averaging the luminance values of the pixels 21a in the X-ray images A1 and A2. For example, the dose of X-rays P2a absorbed by the subject M is calculated from a difference between the average of the luminance values of the pixels 21a in the X-ray images A1 and A2 and the average of the luminance values of the pixels 21b in the X-ray images A1 and A2.

In this way, the refraction information calculating unit 9 can independently calculate information of an X-ray image based on an amount of X-rays absorbed by the subject M and information of the small-angle X-ray scattered image based on refraction of X-rays due to the subject M. Accordingly, the scattered image reconstructing unit 10 can reconstruct the small-angle X-ray scattered image based on EI-XPCi and can reconstruct a general X-ray image (an X-ray absorption image) based on an absorption imaging method.

<Effect of Configuration According to the First Embodiment>

In the X-ray imaging device 1 according to the first embodiment, the scintillator elements 15 disposed in the X-ray detector 5 are partitioned by the light-shielding walls 17 in a lattice shape. By employing the X-ray detector 5 having this configuration, it is possible to omit the detection mask which is a conventional essential element.

The detection mask in the conventional device has a function of further blocking a part of X-rays which is changed to a fan beam shape by the sample mask. Then, a plurality of times of X-ray imaging are performed while relatively moving the detection mask and the X-ray detector and the sample mask and appropriately changing the area in which X-rays are incident on the X-ray detector. A small-angle X-ray scattered image is generated based on a plurality of X-ray images acquired by the X-ray imaging. However, since it is difficult to manufacture the detection mask of a sufficient thickness with high accuracy and large area, the cost of the X-ray imaging device increases. Since it is difficult to accurately align the detection mask and the X-ray detector, there is concern about a decrease in diagnosability of the small-angle X-ray scattered image due to a position deviation.

On the other hand, in the X-ray imaging device 1 according to the first embodiment, the scintillator layer 11 is constituted by the light-shielding walls 17 in a lattice shape and the scintillator elements 15 disposed in cells defined by the light-shielding walls 17. That is, some of X-rays 3a which are transmitted by the sample mask 7 and are incident on the surface (the X-ray incidence surface) of the X-ray detector 5 are incident on the scintillator elements 15 and are converted into scintillator light W. The other X-rays 3a which are not incident on the scintillator elements 15 are incident on the light-shielding walls 17 and are transmitted by the X-ray detector 5 without being converted into light. That is, similarly to the X-ray absorbing materials of the detection mask in the conventional device, the light-shielding walls 17 hinders conversion of some of X-rays incident on the X-ray detector 5 into scintillator light. Accordingly, the function of the detection mask that limits some of X-rays transmitted by the sample mask 7 can be replaced with the light-shielding walls 17 disposed in the scintillator layer 11.

In the X-ray imaging device 1 according to the first embodiment, as illustrated in FIG. 5(a), the length B in the x direction of the scintillator elements 15 and the length in the x direction of the light-shielding walls 17 are set to (T/2) with respect to the pitch T of the scintillator elements 15. That is, the scintillator elements 15 of which the length in the x direction is (T/2) in the scintillator layer 11 and the light-shielding walls 17 of which the length in the x direction is (T/2) are alternately arranged.

A conventional configuration corresponding to the configuration of the first embodiment illustrated in FIG. 5(a) is illustrated in FIG. 5(b). That is, a detection mask V in which the configuration of the first embodiment corresponds to a configuration in which the X-ray transmitting materials R2 of which the length in the x direction is B (that is, T/2) and the X-ray absorbing materials R1 of which the length in the x direction is (T/2) are alternately arranged in the x direction is disposed at a position close to the surface of the scintillator layer 11 in which the light-shielding walls 17 are not disposed.

In the configuration illustrated in FIG. 5(b) including the detection mask V, X-rays incident on the X-ray absorbing materials R1 among X-rays 3a are absorbed and thus are not converted into scintillator light. X-rays incident on the X-ray transmitting materials R2 are transmitted by the detection mask V, incident on the scintillator elements constituting the scintillator layer 11, and are converted into scintillator light W. On the other hand, in the configuration illustrated in FIG. 5(a) in which the scintillator layer 11 is partitioned by the light-shielding walls 17, X-rays incident on the light-shielding walls 17 among the X-rays 3a are not absorbed by the scintillator elements 15 and are transmitted by the X-ray detector 5 and thus are not converted into scintillator light.

The X-rays incident on the scintillator elements 15 are converted into scintillator light. Accordingly, in FIGS. 5(a) and 5(b), all the areas of X-rays 3a which are converted into scintillator light become an area K in which rectangles extending in the y direction and having a length of B/2 in the x direction, that is, T/4, are arranged in parallel (FIG. 5(c)). In any of the configurations illustrated in FIGS. 5(a) and 5(b), the area K is displaced in the x direction due to refraction of X-rays 3a. By relatively moving the sample mask 7 and the X-ray detector 5, the position of the area K in the scintillator layer 11 is displaced in this way in any configuration.

Accordingly, in any of the configurations illustrated in FIGS. 5(a) and 5(b), it is possible to acquire the small-angle X-ray scattered image of the subject M by capturing X-ray images at the initial position and a position to which the relative position is moved by a distance C in the x direction from the initial position. In this way, in the configuration according to the first embodiment, the light-shielding walls and the scintillator elements are repeatedly arranged in the x direction on the X-ray incidence surface of the X-ray detector. The repeated-arrangement configuration of the X-ray incidence surface corresponds to a configuration in which the X-ray absorbing materials and the X-ray transmitting materials are repeatedly arranged in the detection mask V. Accordingly, in the X-ray imaging device according to the first embodiment, it is possible to suitably acquire a small-angle X-ray scattered image of a subject M even when the detection mask V is omitted.

That is, since the detection mask which it is difficult to manufacture with a large area is not required, it is possible to easily acquire a small-angle X-ray scattered image with a larger size by performing EI-XPCi on the X-ray detector with a large area. Since the detection mask with a large area and high accuracy does not need to be manufactured, it is possible to reduce the manufacturing cost of the X-ray imaging device that can capture a small-angle X-ray scattered image.

In the X-ray imaging device according to the first embodiment, since the light-shielding walls 17 corresponding to the X-ray absorbing materials of the detection mask are formed integrally with the X-ray detector 5, a position deviation of the light-shielding walls 17 and the scintillator elements 15 does not occur. That is, it is possible to solve the problem in that quality of a small-angle X-ray scattered image degrades due to a position deviation of the detection mask and the X-ray detector, which is concerned in the convention device.

In the conventional configuration illustrated in FIG. 5(b), since scintillator light W emitted from the scintillator layer 11 is scattered in the x direction, a resolution of an X-ray image decreases. On the other hand, in the device according to the first embodiment, since the scintillator layer 11 is partitioned by the light-shielding walls 17 in a lattice shape, it is possible to suitably avoid scattering of scintillator light W which occurs in the scintillator elements 15. Accordingly, in the X-ray imaging device according to the first embodiment, it is possible to improve a resolution of a small-angle X-ray scattered image and to further improve image quality.

[Second Embodiment]

A second embodiment of the invention will be described below. The entire configuration of an X-ray imaging device according to the second embodiment and setting of an initial position are the same as in the first embodiment. The second embodiment is different from the first embodiment, in the arrangement patterns of the scintillator elements 15 disposed in the X-ray detector 5. The second embodiment is also different from the first embodiment, in that the moving mechanism 6 can be omitted.

<Arrangement Pattern of Scintillator Elements in Second Embodiment>

The arrangement pattern of the scintillator elements 15 which characterizes the second embodiment will be described below. In the X-ray imaging device 1 according to the second embodiment, the scintillator layer 11 has a configuration in which a plurality of scintillator arrays 23 extending in the x direction illustrated in FIG. 6(a) are arranged in the y direction as illustrated in FIG. 6(b). Each of the scintillator arrays 23 has a shape in which a plurality of scintillator elements 15 arranged in the x direction are partitioned by the light-shielding walls 17 in a lattice shape.

Arrangement patterns in the x direction of the scintillator elements 17 disposed in the scintillator arrays are deviated in the x direction in the neighboring scintillator arrays 23. That is, the lattice pattern of the light-shielding walls 17 is deviated in the x direction in the neighboring scintillator arrays 23. As a result, the scintillator layer 11 has a configuration in which two types of scintillator arrays 23 in which the arrangement patterns of the scintillator elements 15 are deviated in the x direction are alternately arranged in the y direction.

For the purpose of distinction, one of two types of scintillator arrays 23 having different arrangement patterns of the scintillator elements 17 is referred to as a scintillator array 23A and the other is referred to as a scintillator array 23B (FIG. 6(b)). For the purpose of distinction, the scintillator elements 15 disposed in the scintillator array 23A are referred to as scintillator elements 15A, and the scintillator elements 15 disposed in the scintillator array 23B are referred to as scintillator elements 15B. The pixels 21 bordering the scintillator elements 15A are referred to as pixels 21A and the pixels 21 bordering the scintillator elements 15B are referred to as pixels 21B.

A unit Un is configured between neighboring pixels 21A and 21B adjacent in the y direction (FIG. 6(b)). As will be described later, by performing a calculation process on the X-ray detection signals output from the pixels 21 in the same unit Un, a small-angle X-ray scattered image is generated by one time of X-ray emission. In FIG. 6(b), it is assumed that the pixels 21 are arranged in the back of the scintillator elements 15 in a one-to-one correspondence manner. The initial positions of the X-ray detector 5 and the sample mask 7 are set such that X-rays 3a are incident on parts of two scintillator elements 15, that is, the scintillator elements 15A and 15B, in the x direction.

In the second embodiment, it is preferable that a distance D4 by which the scintillator elements 17 are deviated in the x direction in the neighboring scintillator arrays 15 be set to be equal to ½ of the pitch (period) T of the scintillator elements 15. In this case, as illustrated in FIG. 6(b), the scintillator elements 15 are arranged in a zigzag shape on the X-ray incidence surface of the scintillator layer 11. It is assumed that the length B in the x direction of the scintillator elements 15 in the second embodiment the same (T/2) as in the first embodiment.

In the scintillator array 23a and the scintillator array 23b, the arrangement patterns of the scintillator elements 15 are deviated by a distance D4 in the x direction. That is, when X-rays are emitted to the X-ray detector 5, information which is acquired from the scintillator elements 15 of the scintillator array 23b matches information which is acquired from the scintillator elements 15 of the scintillator array 23a when X-rays are emitted after the X-ray detector 5 is moved by the distance D4 in the x direction.

Accordingly, by alternately arranging the scintillator arrays 23a and 23b in which the arrangement patterns of the scintillator elements 15 are deviated by a distance D4 in the x direction, it is possible to acquire X-ray image information when an image is captured without moving the X-ray detector 5 and X-ray image information when an image is captured after the X-ray detector 5 is moved by the distance D4 in the x direction by one time of X-ray emission.

<X-Ray Imaging Process in the Second Embodiment>

A process of performing X-ray imaging using EI-XPCi using the X-ray imaging device 1 according to the second embodiment will be described below. In the first embodiment, an X-ray image A1 is captured at the initial position and X-rays are emitted again to capture an X-ray image A2 after the X-ray detector 5 is moved by a distance C in the x direction. That is, the X-ray imaging processes are different, in that two times of X-ray imaging are performed in the first embodiment but one time of X-ray imaging is performed at the initial position in the second embodiment.

In X-ray imaging, a subject M is mounted on amount table and X-rays 3a are applied to the subject M from the X-ray tube 3. The X-rays 3a are transmitted by the areas of the X-ray transmitting materials R2 disposed in the sample mask 7 and are incident on the X-ray detector 5. The initial positions of the sample mask 7 and the X-ray detector 5 are determined in advance such that X-rays P1 which are not refracted and incident on the X-ray detector 5 are evenly incident on the scintillator elements 15A and the scintillator elements 15B (FIGS. 7(a) to 7(c)). That is, at the initial position, X-rays P1 which are transmitted by the sample mask 7 are incident on two scintillator elements 15 in the x direction.

FIG. 7(b) is a plan view of the X-ray detector 5 illustrating an area in which X-rays are incident in the second embodiment. The scintillator array 23a and the scintillator array 23b are deviated in the x direction in the arrangement pattern of the scintillator elements 15. Accordingly, the scintillator elements 15A and the scintillator elements 15B are different from each other in the area in which X-rays 3a are incident.

Among the scintillator elements 15A, the scintillator elements 15 on which X-rays P1 and X-rays P2a and P2b are incident are distinguished as scintillator elements 15Aa to 15Ac. Among the scintillator elements 15B, the scintillator elements 15 on which X-rays P1 and X-rays P2a and P2b are incident are distinguished as scintillator elements 15Ba to 15Bc (FIG. 7(b)).

As illustrated in FIG. 7(a), areas EA in which X-rays 3a are incident on the scintillator elements 15Aa to 15Ac are distinguished as areas EAa to EAc. The areas in which X-rays 3a are incident on the scintillator elements 15Aa to 15Ac are distinguished as area EAa to EAc. Areas EB in which X-rays 3a are incident on the scintillator elements 15Ba to 15Bc are distinguished as areas EBa to EBc.

The area EA in which the X-rays 3a are incident on each of the scintillator elements 15A is the same as illustrated in FIG. 7(a). That is, since the area EAa corresponds to the right half area of each of the scintillator elements 15Aa, X-rays P1 are incident on the right half of the scintillator element 15Aa. Since X-rays P2a are refracted to the left in the x direction, the area of the area EAb is widened.

Accordingly, the X-ray dose incident on the scintillator element 15Ab increases depending on the refraction distance Ja of the X-rays P2a in comparison with the X-ray dose incident on the scintillator element 15Aa. Since the area EAc is narrower than the area EAa, the X-ray dose incident on the scintillator elements 15Ac decreases depending on the refraction distance Jb of the X-rays P2b in comparison with the X-ray dose incident on the scintillator element 15Aa.

In this way, the doses of X-rays incident on the scintillator elements 15Aa to 15Ac disposed in the scintillator array 23A are the same as the doses of X-rays incident on the scintillator elements 15a to 15c when X-rays are emitted at the initial position in the first embodiment (FIG. 4(a)). Accordingly, information of an X-ray image which is generated based on the X-ray detection signals output from pixels 21Aa to 21Ac which are the pixels 21A bordering the scintillator elements 15Aa to 15Ac is common to the information of the X-ray image A1 generated in the first embodiment.

On the other hand, the area in which X-rays 3a are incident on each of the scintillator elements 15B is the same as illustrated in the cross-sectional view of FIG. 7(c). The arrangement pattern of the scintillator elements 15B disposed in the scintillator array 23B is deviated by the distance B (distance T/2) in the x direction in comparison with the arrangement pattern of the scintillator elements 15A. Accordingly, the doses of X-rays incident on the scintillator elements 15Ba to 15Bc are the same as the doses of X-rays incident on the scintillator elements 15a to 15c when X-rays are emitted after movement by the distance T/2 from the initial position in the first embodiment (FIG. 4(c)).

That is, in the scintillator array 23B, since the area EBa corresponds to an area of the left half of the scintillator element 15Ba, X-rays P1 are incident on the left half of the scintillator element 15Ba. Since X-rays P2a are refracted to the left in the x direction, the area EBb is narrowed. Accordingly, the X-ray dose incident on the scintillator element 15Bb decreases depending on the refraction distance Ja of the X-rays P2a in comparison with the X-ray dose incident on the scintillator element 15Ba.

Since the X-rays P2b are refracted to the right in the x direction, the area EBc is narrower than the area EBa. As a result, the X-ray dose incident on the scintillator element 15Bc increases depending on the refraction distance Jb of the X-rays P2b in comparison with the X-ray dose incident on the scintillator element 15Ba. That is, information of an X-ray image generated based on the X-ray detection signals output from pixels 21Ba to 21Bc which are the pixels 21B bordering the scintillator elements 15Ba to 15Bc is common to information of an X-ray image A2 generated in the first embodiment.

An X-ray image captured in the second embodiment in this way has image information of the X-ray image A1 and image information of the X-ray image A2 which are captured in the first embodiment. The refraction information calculating unit 9 performs a calculation process of calculating a difference in the luminance value based on the X-ray detection signals between the pixel 21A and the pixel 21B belonging to the same unit Un. The refraction information of the X-rays 3a in each unit Un is calculated through the calculation process.

That is, in an area on which non-refracted X-rays P1 are incident, the difference in the luminance value between the pixel 21Aa and the pixel 21Ba belonging to the same unit Un is zero. On the other hand, in an area on which X-rays P2 refracted by the subject Mare incident, the difference in the X-ray detection signal is not zero. In an area in which X-rays P2a refracted to the left are incident, the difference in the luminance value between the pixel 21Ab and the pixel 21Bb belonging to the same unit Un has a plus value. In an area in which X-rays P2b refracted to the right are incident, the difference in the luminance value between the pixel 21Ac and the pixel 21Bc belonging to the same unit Un has a minus value. In this way, the refraction information calculating unit 9 calculates the refraction direction of the X-rays 3a based on the difference in the luminance value.

When the difference in the luminance value in each of the pixel 21A and the pixel 21 has a plus or minus value, the absolute value of the difference in the luminance value increases as the refraction distance Ja or Jb of X-rays P2 increases. Accordingly, the refraction angle of the X-rays P2 is calculated based on the difference in the luminance value between the pixel 21A and the pixel 21B belonging to the same unit Un.

The scattered image reconstructing unit 10 reconstructs a small-angle X-ray scattered image of the subject M using the unit Un including the pixel 21A and the pixel 21B adjacent in the y direction as one pixel based on the refraction information of X-rays 3a for each unit Un. In the second embodiment, by performing one time of X-ray emission in this way, it is possible to acquire a small-angle X-ray scattered image of a subject M.

<Effect of Configuration According to the Second Embodiment>

The X-ray detector 5 of the X-ray imaging device according to the second embodiment is configured such that X-rays 3a are incident on two scintillator elements 15 in the x direction. The X-ray detector 5 has a configuration in which the scintillator array 23A which includes the scintillator elements 15A partitioned by the light-shielding walls 17 and arranged in the x direction and which extends in the x direction and the scintillator array 23B which includes the scintillator elements 15B partitioned by the light-shielding walls 17 and arranged in the x direction and which extends in the x direction are alternately arranged in the y direction. The arrangement pattern of the scintillator elements 15A and the arrangement pattern of the scintillator elements 15B are deviated by the distance D4 in the x direction.

In the X-ray detector 5 according to the second embodiment, similarly to the first embodiment, the scintillator layer 11 is partitioned by the light-shielding walls 17 in a lattice shape. Accordingly, when EI-XPCi is performed using the X-ray imaging device according to the second embodiment, the detection mask can be omitted similarly to the first embodiment. Accordingly, since the detection mask which is it difficult to manufacture is not required, it is possible to reduce the cost of the X-ray imaging device. Since the position deviation of the light-shielding walls in the X-ray detector can be suitably avoided, it is possible to acquire a small-angle X-ray scattered image with high quality. Since scattering of scintillator light can be prevented by the light-shielding walls 17, it is possible to improve a resolution of an X-ray image.

The X-ray detector according to the second embodiment has a configuration in which two types of scintillator arrays 23A and 23B of which the arrangement patterns of the scintillator elements 15 are deviated by a predetermined distance D4 in the x direction are alternately arranged in the y direction. Accordingly, in the second embodiment, it is possible to acquire information of an X-ray image captured at the initial position and information of an X-ray image captured after the X-ray detector 5 is moved by distance D4 in the x direction from the initial position by one time of X-ray imaging.

The X-rays 3a are incident on two scintillator elements 15A and 15B in the x direction. Accordingly, the refraction direction and the refraction distance of the X-rays 3a in the x direction by detecting the difference in X-ray dose between the areas EAa to EAc and the areas EBa to EBc at the time of capturing one X-ray image.

The refraction information calculating unit calculates information of the refraction direction and the refraction distance of the X-rays 3a in the x direction by performing a calculation process such as calculating a difference between two types of X-ray image information acquired by one time of X-ray emission. A small-angle X-ray scattered image of the subject M is reconstructed based on the calculated information. Accordingly, the number of times of X-ray imaging which is required to acquire the small-angle X-ray scattered image is only one. As a result, it is possible to reduce an exposure dose of a subject in capturing a small-angle X-ray scattered image and to shorten a time required to capture the small-angle X-ray scattered image.

In general, the distance D4 is short. Accordingly, when the X-ray detector is actually moved, a distance by which the X-ray detector 5 is actually moved may be different from the assumed distance D4. By actually moving the X-ray detector 5, there is concern about a problem in that the relative position of the X-ray tube 3, the X-ray detector 5, and the sample mask 7 is deviated from the assumed position due to vibration or the like of the X-ray detector 5.

In the second embodiment, the moving mechanism 6 is omitted and a small-angle X-ray scattered image is generated by one time of X-ray emission without moving the X-ray detector 5. Accordingly, it is possible to prevent occurrence of deviation of the distance by which the X-ray detector 5 is actually moved, vibration of the X-ray detector 5, or the like. As a result, since the deviation of the relative position of the constituents such as the X-ray tube 3 and the X-ray detector 5 can be more satisfactorily prevented, it is possible to suitably prevent a decrease in diagnosability of a small-angle X-ray scattered image due to the deviation of the relative position between the constituents in the second embodiment.

The X-ray detector 5 according to the second embodiment is configured such that the scintillator elements 15 are arranged in zigzag on the X-ray incidence surface. That is, the distance D4 by which the arrangement patterns of the scintillator elements 15 are deviated corresponds to half the pitch T of the scintillator elements 15. In this case, information of the X-ray image A1 which is captured at the initial position and information of the X-ray image A2 which is captured in a state in which the X-ray detector is moved by a distance of (T/2) from the initial position can be acquired by one time of X-ray imaging.

In the conventional EI-XPCi, generally, a calculation process is performed using the X-ray image which is captured at the initial position and the X-ray image which is captured in a state in which the X-ray detector is moved by a distance of (T/2) from the initial position and a small-angle X-ray scattered image is reconstructed. Accordingly, by arranging the scintillator elements 15 in zigzag in the X-ray detector 5, it is possible to reconstruct a small-angle X-ray scattered image with high accuracy using the conventional calculation method.

[Third Embodiment]

A third embodiment of the invention will be described below. The entire configuration of an X-ray imaging device 1A according to the third embodiment is the same as illustrated in FIG. 8(a). The entire configuration of an X-ray imaging device 1A according to the third embodiment is common to the second embodiment and is different from the entire configuration of the first embodiment illustrated in FIG. 1(a), in that the moving mechanism 6 can be omitted. The X-ray imaging device 1A according to the third embodiment is different from the X-ray imaging devices according to the first and second embodiments, in a configuration of a sample mask 7A and a positional relationship between scintillator elements 15 and pixels 21.

The configuration of the sample mask 7A in the third embodiment is illustrated in FIG. 8(b). The sample mask 7A includes an X-ray absorbing material R1 which is formed in a lattice shape and square X-ray transmitting materials R2 which are arranged in a two-dimensional matrix shape. That is, cells partitioned in a two-dimensional matrix shape by the X-ray absorbing material R1 in the lattice shape are formed in the sample mask 7A and the X-ray transmitting materials R2 are arranged in the cells partitioned by the X-ray absorbing material R1.

A pitch of the X-ray transmitting materials R2 in the x direction and the y direction is defined as G. A length of each of the X-ray absorbing materials R2 in the x direction and the y direction is defined as N. In this case, X-rays 3a emitted from the X-ray tube 3 are limited to a shape in which pencil beams with a side length of N are arranged in a two-dimensional matrix shape by the sample mask 7A. The positional relationship between the X-ray tube 3, the X-ray detector 5, and the sample mask 7 is the same as in the first embodiment.

The sample mask 7A is not limited to the configuration in which the X-ray transmitting materials R2 are arranged in a two-dimensional matrix shape, and a configuration in which the X-ray absorbing material R1 and the X-ray transmitting materials R2 are replaced with each other and the X-ray absorbing materials R1 are arranged in a two-dimensional matrix shape as illustrated in FIG. 8(c) may be employed. In this case, the sample mask 7A is formed such that X-ray transmitting materials R2 form a lattice shape. It is assumed that the sample mask 7A according to the third embodiment has the configuration illustrated in FIG. 8(b).

Similarly to the first embodiment, the scintillator layer 11 according to the third embodiment has a configuration in which scintillator elements 15 partitioned by light-shielding walls 17 in a lattice shape are arranged in a two-dimensional matrix shape (FIG. 9(a)). A pitch of the scintillator elements 15 in the x direction and the y direction is defined as T. A length of each of the scintillator elements 15 in the x direction and the y direction is defined as B. The output layer 13 includes a substrate 19 on which pixels 21 are arranged in a two-dimensional matrix shape (FIG. 9(b)).

As illustrated in the cross-sectional view of FIG. 9(c), the pixels 21 are arranged to correspond to the scintillator elements 15 in a one-to-one correspondence manner. It is preferable that a pitch of the pixels 21 and a length of each pixel 21 in the x direction and the y direction be substantially the same as those of the scintillator elements 15. In the drawings, a pixel 21 is illustrated to be larger than a scintillator element 15 for the purpose of convenience of explanation.

Details of the positional relationship between the sample mask 7 and the X-ray detector 5 are the same as illustrated in FIGS. 9(c) and 9(d). When X-rays 3a emitted from the X-ray tube 3 are not refracted and propagate straight, the relative positional relationship between the sample mask 7 and the X-ray detector 5 is set such that the X-rays 3a are transmitted by the X-ray transmitting materials R2 of the sample mask 7 and then are incident on the center of four scintillator elements 15 arranged in two rows and two columns.

That is, the initial positions of the sample mask 7 and the X-ray detector 5 are determined such that X-rays 3a transmitted by the X-ray transmitting materials R2 are incident on a part k of each of two scintillator elements 15 in the x direction and the y direction. In this case, an area H of X-rays 3a which are transmitted by the X-ray transmitting materials R2 and are incident on the X-ray detector 5 is located at the center of an area including four scintillator elements 15a to 15d to partially cover the four scintillator elements as illustrated in FIG. 9(d).

In FIG. 9(d), four scintillator elements 15a to 15d denoted by solid lines and pixels 21a to 21d denoted by dotted lines which are the pixels 21 bordering the scintillator elements 15a to 15d are considered as one unit Un surrounded by thick dotted lines. In this case, the X-ray detector 5 can be considered to have a configuration in which units Un are repeatedly arranged in the x direction and the y direction. When X-rays 3a are emitted from the X-ray tube 3 to the X-ray detector 5 in a state in which a subject M is not present, X-rays 3a are not refracted and thus the area H is located at the center of each unit Un. Ends of the area H overlap the scintillator elements 15a to 15d.

In a structure of a unit Un illustrated in FIG. 10(a), it is preferable that the thickness of the light-shielding walls 17 in the area in which X-rays 3a are incident (a cross area overlapping the area H) be smaller among the light-shielding walls 17. It is preferable that the thickness of the light-shielding walls 17 in an area in which X-rays 3a are not incident be larger among the light-shielding walls 17.

A technique of determining refraction of X-rays 3a based on variations in luminance value of the pixels 21a to 21d in the third embodiment will be described below with a focus on one unit Un. Areas in which the scintillator elements 15a to 15d overlap the area H are defined as Ha to Hd. When X-rays 3a are not refracted, the area H is located at the center of the unit Un as illustrated in FIG. 10(a). Accordingly, the magnitudes of the areas of the scintillator elements 15a to 15d overlapping the area H are the same. That is, the magnitudes of the areas Ha to Hd are the same. Accordingly, since X-ray doses of X-rays 3a incident on the scintillator elements 15a to 15d are the same, the luminance values of the pixels 21a to 21d are the same.

On the other hand, when X-rays 3a are refracted, the luminance values of the pixels 21a to 21d in the same unit Un are changed depending on the refraction direction of the X-rays 3a. When X-rays 3a are refracted to the left in the x direction due to transmission by a subject M, the position of the area H is displaced in the x direction from the center of the unit Un denoted by a two-dot chain line to a left area denoted by a solid line as illustrated in FIG. 10(b). Accordingly, the magnitudes of the area Ha and the area Hc are larger than the magnitudes of the area Hb and the area Hd depending on the magnitude of the refraction distance Jx of X-rays 3a which are refracted in the x direction.

As a result, the luminance values of the pixel 21a and the pixel 21c are larger than the luminance values of the pixel 21b and the pixel 21d. On the other hand, when X-rays 3a are refracted to the right, the area H is displaced to the right in the x direction and thus the luminance values of the pixel 21b and the pixel 21d increase. Accordingly, by calculating a difference between a sum of the luminance value of the pixel 21a and the luminance value of the pixel 21c and a sum of the luminance value of the pixel 21b and the luminance value of the pixel 21d, it is possible to calculate a refraction direction and a refraction angel (a refraction distance) of X-rays 3a in the x direction.

In the sample mask 7 according to the third embodiment, the X-ray transmitting materials R2 are arranged in a two-dimensional matrix shape and the area H is positioned to cover a plurality of scintillator elements 15 in the x direction and the y direction. Accordingly, in the first and second embodiments, refraction of X-rays 3a in one direction, that is, in the x direction, can be detected. On the other hand, in the third embodiment, refraction of X-rays 3a in two perpendicular directions, that is, in the x direction and the y direction, can be detected.

When X-rays 3a are refracted to the upside in the y direction due to transmission by a subject M, the position of the area H is displaced in the y direction from the center of the unit Un denoted by a two-dot chain line to an upper area denoted by a solid line as illustrated in FIG. 10(c). Accordingly, the magnitudes of the area Ha and the area Hb are larger than the magnitudes of the area Hc and the area Hd depending on the magnitude of a refraction distance Jy of X-rays 3a which are refracted in the y direction.

As a result, the luminance values of the pixel 21a and the pixel 21b are larger than the luminance values of the pixel 21c and the pixel 21d. When X-rays 3a are refracted to the downside in the y direction, the area H is displaced to the downside in the y direction and thus the luminance values of the pixel 21c and the pixel 21d increase. Accordingly, by calculating a difference between a sum of the luminance value of the pixel 21a and the luminance value of the pixel 21b and a sum of the luminance value of the pixel 21c and the luminance value of the pixel 21d, it is possible to calculate a refraction direction and a refraction distance of X-rays 3a in the y direction.

When X-rays 3a are refracted to the left-upper side in an xy plane due to transmission by a subject M, the position of the area H is displaced from the center of the unit Un denoted by a two-dot chain line to a left-upper area denoted by a solid line as illustrated in FIG. 10(d). In this case, the magnitude of the area Ha increases particularly and the magnitude of the area Hd decreases particularly, depending on the magnitudes of the refraction distances Jx and Jy. As a result, the luminance value of the pixel 21a among the pixels 21a to 21d increases particularly and the luminance value of the pixel 21d decreases particularly. The luminance values of the pixel 21b and the pixel 21c are changed depending on the magnitudes of the refraction distances Jx and Jy. In this way, it is possible to calculate the refraction direction and the refraction distance of X-rays 3a based on changes of the luminance values of the pixels 21a to 21d belonging to the same unit Un by one time of X-ray imaging.

When EI-XPCi is performed using the X-ray imaging device 1A according to the third embodiment, the initial positions of the sample mask 7A and the X-ray detector 5 are set such that X-rays 3a which are transmitted by the sample mask 7A are incident on two scintillator elements 15 in the x direction and the y direction (Step S1). The X-rays 3a are emitted from the X-ray tube 3 to a subject M at the initial positions and an X-ray image A is captured (Step S2). The image generating unit 8 generates an X-ray image A based on X-ray detection signals output from the pixels 21.

The refraction information calculating unit 9 calculates the luminance values of the pixels 21a to 21d in each unit Un in the X-ray image A. By performing a calculation process such as calculating differences in the luminance values, the refraction direction and the refraction distance of X-rays 3a in each unit Un are calculated in the x direction and the y direction (Step S3).

The scattered image reconstructing unit 10 generates a small-angle X-ray scattered image of the subject M in which four pixels 21a to 21d (unit Un) arranged in two rows and two columns is used as one pixel based on the refraction information of X-rays 3a calculated for each unit Un (Step S5). Similarly to the first and second embodiments, information on an X-ray absorption image based on an amount of X-rays absorbed by the subject M can be acquired from the X-ray image A. That is, the image generating unit 8 can generate an X-ray absorption image based on an absorption imaging method independently of information of the small-angle X-ray scattered image based on a decrease in the sum of the luminance values of the pixels 21a to 21d in each unit Un.

<Effect of Configuration According to the Third Embodiment>

In the X-ray imaging device according to the third embodiment, the sample mask 7A includes the X-ray transmitting materials R2 which are arranged in a two-dimensional matrix shape and which transmit X-rays. X-rays 3a transmitted by the sample mask 7A are incident on two scintillator elements 15 in the x direction and the y direction. That is, X-rays 3a limited to a pencil beam shape by the sample mask 7A are incident on the scintillator elements 15a and 15b (and the scintillator elements 15c and 15d) in the x direction. The X-rays 3a are incident on parts of the scintillator elements 15a and 15c (and the scintillator elements 15b and 15d) in the y direction.

According to this configuration, when X-rays 3a are refracted with respect to the x direction, a difference in dose of X-rays 3a incident on the scintillator elements 15a and 15b varies. Accordingly, information of the refraction direction and the refraction angle of X-rays 3a with respect to the x direction can be detected based on a difference between X-rays 3a incident on the scintillator elements 15a and 15b. When X-rays 3a are refracted with respect to the y direction, the difference in dose of X-rays 3a incident on the scintillator elements 15a and 15c varies. Accordingly, the information of the refraction direction and the refraction angle of X-rays 3a with respect to the y direction can be detected based on the difference in dose between X-rays 3a incident on the scintillator elements 15a and 15c.

Accordingly, the refraction direction and the refraction distance of X-rays 3a transmitted by the subject M can be two-dimensionally calculated based on the changes in the luminance values of the pixels 21a to 21d which are the pixels 21 bordering the scintillator elements 15a to 15d on which X-rays 3a are incident. That is, information on refraction of X-rays 3a can be calculated in the x direction and the y direction by calculating the luminance values of the pixels 21a to 21d in an X-ray image captured by one time of X-ray emission.

In this way, in the X-ray imaging device 1A according to the third embodiment, the refraction direction and the refraction distance of X-rays 3a can be calculated in two perpendicular directions. Accordingly, in comparison with conventional EI-XPCi in which information on the refraction of X-rays 3a can be calculated in only one direction, it is possible to acquire a small-angle X-ray scattered image with higher accuracy and higher diagnosability in the third embodiment. Since a small-angle X-ray scattered image can be acquired by one time of X-ray imaging, it is possible to further reduce an exposure dose of a subject and to further shorten a time required for capturing a small-angle X-ray scattered image.

[Fourth Embodiment]

A fourth embodiment of the invention will be described below. The entire configuration of an X-ray imaging device according to the fourth embodiment is the same as in the third embodiment. The configuration according to the fourth embodiment is different from the configuration of the third embodiment, in that a mechanism that corrects a relative position deviation which a deviation of a relative position of the sample mask 7 and the X-ray detector 5 due to vibration occurring in the X-ray imaging device is further provided.

As described above in the third embodiment, since X-rays 3a incident on the X-ray detector 5 are refracted at the time of being transmitted by a subject M, the difference in X-ray dose incident on the scintillator elements 15a to 15d belonging to the same unit Un varies. However, the variation of the difference in X-ray dose incident on the scintillator elements 15 is caused for a reason other than the refraction of X-rays 3a.

That is, when a deviation of a relative position of the sample mask 7 and the X-ray detector 5 occurs, the difference in dose of X-rays 3a incident on the scintillator elements 15a to 15d varies. The deviation of the relative position is caused by causing the X-ray detector 5 to move parallel to the xy plane from a position denoted by a dotted line to a position denoted by a solid line, for example, as illustrated in FIG. 11(a). For example, as illustrated in FIG. 11(b), the deviation of the relative position is also caused by causing the X-ray detector 5 to rotationally move around an axis in the z direction from a position denoted by a dotted line to a position denoted by a solid line.

As illustrated in FIG. 12, an X-ray detector 5B according to the fourth embodiment uses units Un which are disposed at four corners of an X-ray incidence surface as units Un for relative position deviation correction. In the units Un which are used for position deviation correction, the unit Un which is located at the left-top corner of the X-ray incidence surface is distinguished as a unit Un1. The units Un for relative position deviation correction located at the right-top corner, the left-bottom corner, and the right-bottom corner are distinguished as units Un2 to Un4.

The positions and the number of units Un which are used for relative position deviation correction are not limited to the configuration illustrated in FIG. 11, and may be appropriately changed. It is preferable that three or more units Un which are not arranged in a straight line be used for relative position deviation correction, in that the relative position deviation due to parallel movement of the X-ray detector 5 in the x direction and the y direction or the like and the relative position deviation due to rotational movement of the X-ray detector 5 around an axis in the z direction or the like can be corrected. It is preferable that the positions of the units Un which are used for relative position deviation correction be close to an end of the X-ray detector 5, in that X-rays 3a incident on the units Un are not transmitted by a subject M in X-ray imaging.

When EI-XPCi is performed using the X-ray imaging device according to the fourth embodiment, the initial positions of the sample mask 7A and the X-ray detector 5 are set such that X-rays 3a transmitted by the sample mask 7A are incident on two scintillator elements 15 in the x direction and the y direction (Step S1), similarly to the third embodiment. At the initial position, X-rays 3a are emitted from the X-ray tube 3 to the subject M and an X-ray image A is captured (Step S2). The image generating unit 8 generates an X-ray image A by X-ray imaging.

The refraction information calculating unit 9 calculates luminance values of the pixels 21a to 21d in each unit Un in the X-ray image A. By performing a calculation process such as calculating a difference in the luminance value, a refraction direction and a refraction distance of X-rays 3a in each unit Un are calculated in the x direction and the y direction (Step S3).

As a process characterizing the fourth embodiment, the refraction information calculating unit 9 corrects the refraction information of X-rays 3a calculated in Step S4 based on the luminance values of the pixels 21 in the units Un1 to Un4 for relative position deviation correction (Step S4). The scattered image reconstructing unit 10 generates a small-angle X-ray scattered image of the subject M using four pixels 21a to 21d (unit Un) arranged in two rows and two columns as one pixel based on the refraction information corrected in Step S5 (Step S5).

The process of Step S5 of correcting information of the refraction direction and the refraction distance of X-rays 3a using the units Un1 to Un4 will be described below. When the X-ray detector 5 moves parallel to the X-ray incidence surface (the xy plane) as illustrated in FIG. 11(a), the relative position of the sample mask 7A and the X-ray detector 5 also moves along the xy plane.

In this case, as illustrated in FIG. 13(a), positions of areas H in which X-rays 3a are incident on the X-ray detector 5 in the units Un1 to Un4 move the same distance in the same direction. Distances by which the area H move in the x direction and the y direction in the units Un1 to Un4 are referred to as Lx1 to Lx4 and Ly1 to Ly4 respectively. The image generating unit 8 can determine that the relative position of the X-ray detector 5 and the sample mask 7 moves parallel based on the fact that the distances Lx1 to Lx4 are the same and the distances Ly1 to Ly4 are the same. The distances Lx1 to Lx4 and Ly1 to Ly4 are calculated based on the luminance values of the pixels 21a to 21d in the units Un1 to Un4 respectively.

In the unit Un on which X-rays 3a transmitted by a subject M are incident, when the refraction distance of X-rays 3a calculated by the refraction information calculating unit 9 in Step S3 is Jx in the x direction and Jy in the y direction, the relative position of the X-ray detector 5 and the sample mask 7 moves Lx in the x direction and Ly in the y direction. Accordingly, the distance by which X-rays 3a incident on the unit Un are actually refracted is (Jx−Lx) in the x direction and (Jy−Ly) in the y direction. Through this calculation process, it is possible to correct relative position deviation due to parallel movement of the relative position of the X-ray detector 5 and the sample mask 7.

When the X-ray detector 5 moves rotationally around an axis parallel to the z direction as illustrated in FIG. 11(b), the relative position of the sample mask 7A and the X-ray detector 5 also moves rotationally. In this case, as illustrated in FIG. 13(b), the positions of the areas H in the units Un1 to Un4 move in different directions depending on the position of a rotation axis, a rotation direction, and a rotation angle of the X-ray detector 5.

The refraction information calculating unit 9 calculates the position of the rotation axis, the rotation direction, and the rotation angle of the X-ray detector 5 based on the distances Lx1 to Lx4 and Ly1 to Ly4. The refraction information calculating unit 9 corrects the apparent refraction distances Jx and Jy of X-rays 3a in the x direction and the y direction calculated in Step S4 based on the calculated information on the rotation of the X-ray detector 5.

In the fourth embodiment, the relative position deviation correction is performed using the units Un1 to Un4 including a plurality of pixels. Since the units Un1 to Un4 are three or more units which are located on a straight line, a deviation of the relative position of the X-ray detector 5 and the sample mask 7 can be detected based on the luminance values of the pixels 21 in the units Un1 to Un4. The apparent refraction direction and the apparent refraction distance of X-rays 3a which are transmitted by the subject M and are incident on the X-ray detector 5 are corrected based on the detected value of the relative position deviation.

By correcting the relative position deviation, it is possible to accurately calculate the refraction direction and the refraction distance of X-rays due to transmission by the subject M even when the relative position of the X-ray detector 5 and the sample mask 7 is deviated due to vibration or the like in the X-ray imaging device. Accordingly, by generating a small-angle X-ray scattered image based on the refraction direction and the refraction distance of X-rays after the relative position deviation has been corrected, it is possible to acquire a small-angle X-ray scattered image with high diagnosability and high accuracy for the subject M.

The present invention is not limited to the above-mentioned embodiments and can be modified as follows.

(1) In the first embodiment, the moving mechanism 6 is configured to move the X-ray detector 5, but the moving mechanism 6 is not limited to the configuration as long as it can relatively move the X-ray detector 5 and the sample mask 7 in the x direction. That is, the moving mechanism 6 may be configured to move the sample mask 7 in the x direction. By moving the sample mask 7, the positional relationship in the x direction between the X-ray detector 5 and the sample mask 7 is relatively displaced. Accordingly, it is possible to capture an X-ray image A2 by emitting X-rays after moving the sample mask 7 in the x direction.

(2) In the first or second embodiment, the sample mask 7 has a configuration in which the X-ray absorbing materials R1 extending in the x direction are arranged in parallel in the y direction as illustrated in FIG. 1(*b*), but the sample mask is not limited to the configuration. That is, the configuration described in the third embodiment can be applied as the configuration of the sample mask 7. That is, a configuration in which the X-ray absorbing material R1 is disposed in a lattice shape as illustrated in FIG. 8(*a*) or a configuration in which the X-ray absorbing materials R1 are disposed in a two-dimensional matrix shape as illustrated in FIG. 8(*b*) may be employed.

(3) The configuration in which the units Un for relative position deviation correction are used as in the fourth embodiment is not limited to the third embodiment, but can be applied to the first or second embodiment. When such a configuration is applied to the first embodiment, scintillator elements which are disposed at positions at which incident X-rays 3*a* are not transmitted by a subject M are selected among the scintillator elements 15 and are used for relative position deviation correction. When such a configuration is applied to the second embodiment, an element which is disposed at a position at which incident X-rays 3*a* are not transmitted by a subject M is selected in the unit Un including the scintillator elements 15A and 15B and is used for relative position deviation correction.

After an X-ray image is captured, the direction and the distance in which boundaries of the area H in the scintillator element 15 selected for relative position deviation correction are deviated are detected based on the luminance values of the pixels 21. When the relative position is not deviated, the boundaries of the area H are located at positions at which the scintillator element 15 is evenly divided. On the other hand, when the relative position is deviated, the position of the area H is deviated in the x direction and the luminance values of the pixels 21 increase or decrease with respect to the assumed values. Accordingly, the refraction information calculating unit 9 can detect a deviation of the relative position of the sample mask 7 and the X-ray detector 5 based on the luminance values of the pixels 21 bordering the selected scintillator element 15 and can correct an influence of the relative position deviation on a small-angle X-ray scattered image.

(4) In the second embodiment, a configuration in which the scintillator elements 15 are arranged in zigzag is used, but the present invention is not limited to the configuration. That is, as illustrated in FIG. 13, the initial positions of the X-ray detector 5 and the sample mask 7 have only to be set such that X-rays 3*a* as a cone shaped beam extending in the y direction incident on the X-ray detector 5 are incident on two or more scintillator elements 15 in the x direction. When the initial positions are set in this way, the same advantages as in the second embodiment can be achieved even with the arrangement patterns of the scintillator elements 15 in the scintillator arrays 23A and 23B match in the x direction.

A modified example of the second embodiment will be described below with reference to FIG. 14. FIG. 14(*a*) is a diagram illustrating an X-ray detection surface of the X-ray detector 5 and FIG. 14(*b*) is a diagram illustrating an X-ray imaging device 1 in an A-A cross-section in FIG. 14(*a*). In the X-ray detector 5 according to the modified example, each of the scintillator elements 15 are arranged in a lattice shape. The initial position of the X-ray detector 5 is determined such that X-rays 3*a* are incident on two scintillator elements 15 in the x direction.

That is, as illustrated in FIG. 14(*a*), areas H1, H2*a*, and H2*b* which are areas in which X-rays P1, P2*a*, and P2*b* are incident overlap two scintillator elements 15L and 15R adjacent in the x direction. When X-rays 3*a* are not refracted in the x direction, it is preferable that the initial position of the X-ray detector 5 be determined such that X-rays 3*a* (X-rays P1) are evenly incident on the scintillator elements 15L and 15R.

The scintillator elements 15L on which X-rays P1, P2*a*, and P2*b* are incident are distinguished as scintillator elements 15*a*L to 15*c*L. The scintillator elements 15R on which X-rays P1, P2*a*, and P2*b* are incident are distinguished as scintillator elements 15*a*R to 15*c*R. Areas in which X-rays are incident on the scintillator elements 15*a*L to 15*c*L are defined as areas EaL to EcL, and areas in which X-rays are incident on the scintillator elements 15*a*R to 15*c*R are defined as areas EaR to EcR. The pixels 21 bordering the scintillator elements 15L are referred to as pixels 21L, and the pixels 21 bordering the scintillator elements 15R are referred to as pixels 21R.

When EI-PCi is performed using the X-ray imaging device according to the modified example of the second embodiment, similarly to the second embodiment, one time of X-ray imaging is performed at the initial position and an X-ray image A is captured. Since X-rays P1 which are not refracted in the x direction are evenly incident on the scintillator elements 15L and 15R, the magnitudes of the areas EaL and EaR are the same. As a result, the luminance value of the pixel 21*a*L bordering the scintillator element 15*a*L and the luminance value of the pixel 21*a*R bordering the scintillator element 15*a*R are the same. The image generating unit 8 can determine that X-rays incident on the scintillator elements 15L and 15R are not refracted because a difference between the luminance value of the pixel 21L and the luminance value of the pixel 21R in the X-ray image A is zero.

On the other hand, since X-rays P2 are refracted in the x direction at the time of being transmitted by a subject M, the magnitudes of the areas in which X-rays are incident on the scintillator elements 15L and 15R are different from each other. That is, since the area EbL is wider than the area EbR, the luminance value of the pixel 21*b*L is larger than the luminance value of the pixel 21*b*R. The refraction information calculating unit 9 can determine that X-rays incident on the scintillator elements 15L and 15R are refracted to the left side because the difference between the luminance value of the pixel 21L and the luminance value of the pixel 21R has a plus value. Since the difference in the luminance value increases as the refraction distance Ja increases, the refraction information calculating unit 9 can calculate the refraction distance Ja of X-rays P2*a* based on the difference between the luminance value of the pixel 21L and the luminance value of the pixel 21R.

Since the area EcL is narrower than the area EcR, the luminance value of the pixel 21*c*L is smaller than the luminance value of the pixel 21*c*R. The refraction information calculating unit 9 determines that X-rays incident on the scintillator elements 15L and 15R are refracted to the right because the difference between the luminance value of the pixel 21L and the luminance value of the pixel 21R has a minus value, and calculates the refraction distance Jb of X-rays P2*b* based on the difference in the luminance value. In this way, the refraction information calculating unit 9 acquires refraction information in the x direction of X-rays 3*a* which are limited to a fan beam shape extending in the y direction based on the luminance values of the pixels 21 belonging to the same unit Un in one X-ray image A. The scattered image reconstructing unit 10 reconstructs a small-angle X-ray scattered image of the subject M based on the acquired refraction information.

In the X-ray detector 5 according to the second embodiment, since the scintillator elements 15 are arranged in zigzag, the pixels 21 need to be arranged in zigzag to correspond to the scintillator elements 15. On the other hand, in the X-ray detector 5 according to the modified example of the second embodiment, it is possible to generate a small-angle X-ray scattered image of a subject M by one time of X-ray imaging even when the scintillator elements 15 are arranged in a lattice shape. That is, the same advantages as in the second embodiment can be achieved even with a general configuration in which the pixels 21 are arranged in a lattice pattern.

In the second embodiment, since the scintillator elements 15 are arranged in zigzag, the coordinates of the right end of the scintillator element 15A and the coordinates of the left end of the scintillator element 15B in the x direction can be matched with each other. Accordingly, it is possible to easily set the initial position of the X-ray detector 5 such that X-rays P1 are evenly incident on the scintillator elements 15A and 15B. When an X-ray image A is captured, an area in which X-rays P1 is incident corresponds to a half of each of the scintillator elements 15A and 15B and thus it is possible to easily perform the calculation process of the image generating unit 8 which is performed to generate a small-angle X-ray scattered image of a subject M.

(5) In the third embodiment, the initial position is determined such that X-rays 3a incident on the X-ray detector 5 are incident on two or more scintillator elements 15 in the x direction and the y direction, but the present invention is not limited to this configuration. That is, the area H in which X-rays 3a are incident on the X-ray detector 5 may be configured to circumscribe the two or more scintillator elements 15 in the x direction and the y direction.

An example of a configuration of an X-ray detector 5 according to a modified example of the third embodiment will be described below. As illustrated in FIG. 15(a), each of scintillator elements 15 disposed in the X-ray detector 5 has an L shape. Units Un including scintillator elements 15a to 15d arranged in two rows and two columns of which concave portions face a central portion CH are arranged in the x direction and the y direction. The pixels 21a to 21d bordering the scintillator elements 15a to 15d may have the same L shape as the scintillator elements 15 or may have a square shape similarly to the third embodiment (see FIG. 9(b)). Here, it is assumed that the scintillator elements 15a to 15d have an L shape and the pixels 21a to 21d have a square shape.

The initial position of the X-ray detector 5 is set such that an area H in which X-rays 3a not refracted and propagating straight are incident and the scintillator elements 15a to 15d belonging to the same unit Un border each other. The area H is located at the central portion CH of the unit Un and boarders two scintillator elements 15 in each of the x direction and the y direction. The area H borders two scintillator elements 15a and 15b in the x direction, and borders two scintillator elements 15a and 15c in the y direction (FIG. 15(b)).

When EI-XPCi is performed in the modified example of the third embodiment, similarly to the third embodiment, X-rays 3a are emitted one time at the initial position and an X-ray image A is captured. When X-rays 3a are not refracted, the area H is located at a position at which the area H circumscribes the scintillator elements 15a to 15d as illustrated in FIG. 15(b). Accordingly, since X-rays 3a are not incident on the scintillator elements 15a to 15d, all the luminance values of the pixels 21a to 21d are zero.

When X-rays 3a are refracted due to transmission by a subject M, the X-rays 3a are incident on the scintillator elements 15 in the refraction direction. For example, when X-rays 3a are refracted to the left-top side in the xy plane, the position of the area H is displaced to the left-top side as illustrated in FIG. 15(c). In this case, the area H does not overlap the scintillator element 15d on the right-bottom side and partially overlaps the scintillator elements 15a to 15c.

In the state illustrated in FIG. 15(c), the magnitude of an area Hb in which the area H overlaps the scintillator element 15b is proportional to the refraction distance Jb of X-rays 3a in the y direction. The magnitude of an area Hc in which the area H overlaps the scintillator element 15c is proportional to the refraction distance Ja of X-rays 3a in the x direction. The magnitude of an area Ha in which the area H overlaps the scintillator element 15a varies depending on the refraction distances Ja and Jb. When X-rays 3a are incident on the scintillator elements 15a to 15c, the luminance value of the pixel 21d is zero and the luminance values of the pixels 21a to 21c correspond to incident X-ray doses.

The refraction information calculating unit 9 determines the refraction direction of X-rays 3a based on a combination of the pixels 21 among the pixels 21a to 21d of which the luminance value is not zero. The refraction distance Ja of X-rays 3a in the x direction and the refraction distance Jb of X-rays 3a in the y direction are calculated based on the luminance values. The scattered image reconstructing unit 10 generates a small-angle X-ray scattered image of the subject M based on the refraction information of X-rays 3a calculated from the X-ray image A.

In the modified example of the third embodiment, an incidence range of X-rays 3a not refracted but propagating straight circumscribes two or more scintillator elements 15 in the x direction and the y direction. In this case, since the initial values of the luminance values of the pixels 21 are zero, the refraction distance Ja and the refraction distance Jb can be calculated without performing a calculation process of calculating a difference between the luminance values of the pixels 21 as in the third embodiment. Accordingly, it is possible to further simplify a calculation process for generating a small-angle X-ray scattered image.

This modified example is not limited to the third embodiment, but can be applied to other embodiments and other modified examples. For example, a configuration which is applied to the modified example of the second embodiment in which X-rays 3a transmitted by the sample mask 7 have a fan beam shape is illustrated in FIG. 15(d). X-rays 3a limited to a fan beam shape extending in the y direction by the sample mask 7 are incident on the X-ray detector 5. When X-rays 3a are not refracted in the x direction, the initial position of the X-ray detector 5 is set such that the area H in which X-rays 3a are incident circumscribes two scintillator elements 15L and 15R in the x direction.

When X-rays 3a are not refracted, the area H does not overlap the scintillator elements 15L and 15R and thus both the luminance value of the pixel 21L bordering the scintillator element 15L and the luminance value of the pixel 21R bordering the scintillator element 15R are zero. On the other hand, when X-rays 3a are refracted to the left in the x direction, the area H is displaced to the left and thus a part of X-rays 3a are incident on the scintillator element 15L (FIG. 15(e)). Since the magnitude of an area EL in which X-rays 3a are incident on the scintillator elements 15L increases as refraction distance Ja of X-rays 3*a* increases, the refraction information calculating unit 9 can calculate the refraction distance Ja based on the magnitude of the luminance value of the pixel 21L.

When X-rays 3*a* are refracted to the right in the x direction, apart of X-rays 3*a* are incident on the scintillator element 15R and thus the refraction information calculating unit 9 can calculate the refraction distance Jb based on the luminance value of the pixel 21R. In this case, since both the luminance values of the pixels 21L and the 21R are zero, it is possible to calculate the refraction direction and the refraction distance of X-rays 3 in the x direction without performing a calculation process of calculating a difference between the luminance values of the pixels 21. Accordingly, it is possible to further simplify a calculation process for reconstructing a small-angle X-ray scattered image in which a refraction contrast image of a subject M in the x direction is mirrored.

(6) In the above-mentioned embodiments, the X-ray detector 5 has a single-layer structure, but the invention is not limited to this configuration and the X-ray detector may have a two or more-layer structure. When the X-ray detector has a two-layer structure, two X-ray detectors 5 are stacked such as the positions at which the light-shielding walls 17 are disposed are deviated along the xy plane as illustrated in FIG. 16(*a*). By stacking a plurality of X-ray detectors 5 in this way, the scintillator elements 15 disposed in the plurality of X-ray detectors 5 are located to compensate for ranges of the light-shielding walls 17 in which X-rays cannot be detected.

Accordingly, when the X-ray detector 5 has a single-layer structure, X-rays P3 incident on the light-shielding walls 17 are not converted into scintillator light by the scintillator elements 15 and thus X-rays P3 are not detected but are transmitted by the X-ray detector 5. Accordingly, areas in which the light-shielding walls 17 are disposed are areas which may be called blind spots in which X-rays cannot be detected (FIG. 16(*b*)). On the other hand, when the X-ray detector 5 has a two or more-layer structure, X-rays P3 transmitted by the light-shielding walls 17 in the first-layer X-ray detector 5 are incident on the scintillator elements 15 in the second or later-layer X-ray detector 5. Accordingly, in the detector illustrated in FIG. 16, an X-ray refraction contrast image can be acquired in the first layer and an X-ray absorption image can be acquired by the second or later-layer X-ray detectors. Alternatively, by calculating images without moving the X-ray detectors based on the fact that the first-layer X-ray detector and the second-layer X-ray detector have different positional relationships, it is possible to acquire an X-ray refraction contrast image.

In the X-ray detector according to Modified Example (6), two X-ray detectors 5 may be stacked such that the arrangement pattern of the scintillator elements 15 in the first-layer X-ray detector 5 and the arrangement pattern of the scintillator elements 15 in the second-layer X-ray detector 5 are deviated by a distance D4 in the x direction. In this case, when X-rays are emitted to the X-ray detector 5 having a two-layer structure, image information acquired from the second-layer X-ray detector 5 matches image information which is acquired when X-rays are emitted after the first-layer X-ray detector 5 is moved by a distance D4 in the x direction.

Accordingly, in the X-ray detector according to Modified Example (6), X-ray image information when imaging is performed without moving the X-ray detector 5 and X-ray image information when imaging is performed with the X-ray detector 5 moved by a distance D4 in the x direction can be acquired by one time of X-ray emission. That is, by using two X-ray detectors 5 according to the first embodiment, it is possible to achieve the advantage of the X-ray detector 5 according to the second embodiment that a small-angle X-ray scattered image can be suitably captured by one time of X-ray emission without relatively moving the X-ray detector 5 and the sample mask 7.

In modified examples having a configuration (a multi-layer structure) in which a plurality of X-ray detectors 5 are stacked in the z direction, the first-layer X-ray detector 5 means an X-ray detector 5 closest from the X-ray tube 3 among the plurality of X-ray detectors 5 stacked. Hereinafter, for distinction, A is added to the reference signs of constituent elements which are disposed in the first-layer X-ray detector 5 and B is added to the reference signs of constituent elements which are disposed in the second-layer X-ray detector 5.

(7) In the above-mentioned embodiments, a configuration employing an indirect conversion type X-ray detector that converts X-rays into light using scintillator elements or the like and converts the light into an electrical signal has been described, but the configuration of the X-ray detector according to the present invention can be applied to a direct conversion type X-ray detector that directly converts X-rays into an electrical signal. That is, in the configurations according to the embodiments, an X-ray conversion element that is formed of amorphous selenium (a-Se) or the like and converts X-rays into electric charges is used instead of the scintillator element.

By forming groove portions blocking scattering of electric charges in a lattice shape instead of the light-shielding walls, the advantages of the present invention can be obtained from a direct conversion type X-ray detector. The groove F in the direct conversion type X-ray detector according to Modified Example (7) corresponds to the shielding portion in the present invention. In the indirect conversion type X-ray detector, a configuration in which scintillator elements 15 are partitioned by the groove portions instead of the light-shielding walls 17 may be employed.

(8) In the above-mentioned embodiments, the pitch G of the X-ray absorbing materials R1, the length N of the X-ray transmitting materials, the length B of the scintillator elements 15, and the pitch T of the scintillator elements 15 are not limited to the values determined in the embodiments, but may be appropriately changed depending on conditions associated with X-ray imaging. The distance C by which the X-ray detector 5 is moved in the first embodiment may be appropriately changed.

(9) In the configuration according to Modified Example (6), two X-ray detectors in which the light-shielding walls 17 are disposed in the scintillator layer 11 are stacked, but the present invention is not limited to the configuration. That is, as illustrated in FIG. 20(*a*), the light-shielding walls 17 of the scintillator layer 11 may be omitted in the second or later-layer X-ray detector 5B. Each of the X-ray detector 5 according to Modified Example (9) can be applied to the configurations of the embodiments. By employing this configuration, it is possible to simplify the device configuration and thus to provide an X-ray detector with a lower cost.

In the above-mentioned embodiments and modified examples having a multi-layer structure, it is preferable that the pixels 21B disposed in the second-layer X-ray detector 5B be disposed to correspond to the positions of the light-shielding walls A17 disposed in the first-layer X-ray detector 5A. Specifically, it is preferable that the center axis 21*m* of the photoelectric conversion element in each pixel 21B match the center axis 17m of the corresponding light-shielding wall 17A.

X-rays that are converted into scintillator light W by the scintillator elements 15B are X-rays which are incident on the X-ray detector 5B without being detected by the X-ray detector A, that is, X-rays P3 which are incident on the light-shielding walls 17A in the X-ray detector A. Accordingly, by arranging the photoelectric conversion elements of the pixels 21B to correspond to the positions of the light-shielding walls A17, scintillator light W converted by the X-ray detector 5B is detected at a position closer to the center of each pixel 21B. As a result, it is possible to acquire more accurate image information using the X-ray detector 5B.

(10) In the above-mentioned modified examples having a multi-layer structure, the pitches of the pixels 21 in the X-ray detectors 5 are the same, but the present invention is not limited to this configuration. That is, as illustrated in FIG. 20(b), the pitch of the pixels 21B in the second-layer X-ray detector 5B may be set to be larger than the pitch of the pixels 21A in the first-layer X-ray detector 5A.

In the configuration according to Modified Example (10), the pitch of the pixels 21A in the first-layer X-ray detector 5A including the light-shielding walls 17A is smaller. Accordingly, it is possible to acquire more accurate image information including information of small-angle X-ray scattering using the X-ray detector 5A. On the other hand, the pitch of the pixels 21B is relatively large. Accordingly, since elongation of a processing time due to an excessive large amount of information in the X-ray detector 5B can be avoided, it is possible to shorten a time required for acquiring an X-ray image. Since the device configuration of the X-ray detector 5B is more simplified, it is possible to reduce a cost required for manufacturing the device.

(11) In the above-mentioned embodiments, X-rays 3a transmitted by the X-ray transmitting materials R2 of the sample mask 7 are incident on both the light-shielding walls 17 and the scintillator elements 15 when the X-rays are incident on the X-ray detector 5. For example, in the first embodiment, the initial positions of the sample mask 7 and the X-ray detector 5 are determined in advance such that X-rays P1 which are not transmitted by a subject M among X-rays 3a transmitted by the X-ray transmitting materials R2 are evenly incident on the light-shielding walls 17 and the scintillator elements 15 as illustrated in FIG. 4(a).

However, an area in which X-rays 3a are incident on the X-ray detector 5 is not limited to such a configuration. That is, as illustrated in FIG. 21(a), the initial positions of the sample mask 7 and the X-ray detector 5 may be determined such that X-rays 3a limited to a fan beam shape extending in the y direction by the sample mask 7 are incident on the light-shielding walls 17 extending in the y direction. In this case, a pattern of areas (an autoscopic striped pattern) in which X-rays 3a are incident on the X-ray detector 5 substantially matches a formation pattern of the light-shielding walls 17 disposed in the X-ray detector 5. That is, the initial positions of the sample mask 7 and the X-ray detector 5 are set such that each of incidence areas H1 of X-rays 3a incident without being refracted circumscribe the scintillator elements 15 adjacent in the x direction. Accordingly, a part of each incidence area H2 of X-rays 3a which are refracted in the x direction overlaps the scintillator element 15.

In the embodiments and the modified examples having a multi-layer structure, by applying the configuration of Modified Example (11) to the first-layer X-ray detector 5A, a normal X-ray image based on an amount of X-rays absorbed and a small-angle X-ray scattered image based on an amount of X-rays scattered can be acquired. Specifically, it is possible to acquire information on the small-angle X-ray scattered image from the X-ray detector 5A and to acquire normal X-ray image information from the X-ray detector 5B.

That is, as illustrated in FIG. 21(b), among X-rays 3a which are transmitted by the X-ray transmitting materials R2 of the sample mask 7, X-rays P1 which are not refracted in the x direction are incident on the light-shielding walls 17A without being incident on the scintillator elements 15A. Accordingly, X-rays P1 are transmitted by the X-ray detector 5A, are converted into scintillator light W in the scintillator elements 15B, and are detected by the pixels 21B.

On the other hand, X-rays P2 which are refracted in the x direction due to transmission by a subject M or the like are incident on the scintillator elements 15A depending on the refraction distance Ja in the x direction and converted scintillator light is detected by the pixels 21A. Most of the X-rays P2 are transmitted by the X-ray detector 5A and are detected by the pixels 21B. Accordingly, information on the refraction distance Ja of X-rays 3a is acquired from the pixels 21A and information on an amount of X-rays absorbed is acquired from the pixels 21B. Accordingly, with the configuration according to Modified Example (11), it is possible to realize an X-ray detector that can simultaneously acquire a normal X-ray image and a small-angle X-ray scattered image.

(12) In the configuration according to Modified Example (11), in FIG. 21(a), a pitch Hp in the x direction of the areas H1 in which X-rays which have not been refracted are incident matches the pitch T in the x direction of the scintillator elements 15. However, the pitch Hp of the incidence areas H1, that is, the pitch of an autoscopic striped pattern which is generated due to X-rays transmitted by the sample mask 7, may be different from the pitch T of the scintillator elements 15. Particularly, as illustrated in FIG. 22(a), it is preferable that the sample mask 7 and the X-ray detector 5 be configured such that the pitch Hp of the incidence areas H1 is longer than the pitch T of the scintillator elements 15.

In the configuration in which the pitch Hp matches the pitch T as illustrated in FIG. 21(a), it may be difficult to acquire an accurate small-angle X-ray scattered image depending on the refraction direction of X-rays 3a. That is, as illustrated in FIG. 22(b), X-rays P2a and X-rays P2b transmitted by the different X-ray transmitting materials R2 may be refracted in different directions due to transmission by a subject M and may be incident on the same scintillator element 15A. In this case, information of the refraction distance Ja of X-rays P2a and information of the refraction distance Jb of X-rays P2b cannot be distinguished based on the information detected by the pixel 21A bordering the corresponding scintillator element 15A. As a result, it is difficult to acquire an accurate small-angle X-ray scattered image.

Therefore, as in Modified Example (12), it is possible to more satisfactorily prevent different beams of X-rays 3a from being incident on the same scintillator element 15 by configuring the sample mask 7 and the X-ray detector 5 such that the pitch Hp of the autoscopic striped patterns is longer than the pitch T of the scintillator elements 15 (FIG. 22(c)). As a result, since information of the refraction distance Ja of X-rays P2a and the refraction distance Jb of X-rays P2b can be accurately detected, it is possible to realize an X-ray detector 5 that can acquire a more accurate small-angle X-ray scattered image.

(13) In Modified Example (11), X-rays 3a which are limited to a fan beam shape extending in the y direction by the sample mask 7 are incident on the light-shielding walls 17 extending in the y direction, but the present invention is not limited this configuration. That is, as illustrated in FIG. 23(a), X-rays 3a of a fan beam shape extending in the y direction may be incident on the scintillator elements 15 extending in the y direction.

In the configuration according to Modified Example (13), the autoscopic striped patterns substantially matches the arrangement patterns of the scintillator elements 15. That is, the initial positions of the sample mask 7 and the X-ray detector 5 are set such that the incidence areas H1 of X-rays 3a which are not refracted but are incident circumscribe the light-shielding walls 17 adjacent in the x direction. Accordingly, a part of the incidence areas H2 of X-rays 3a which are refracted in the x direction overlap the light-shielding walls 17.

In the embodiments and the modified examples having a multi-layer structure, by applying the configuration of Modified Example (13) to the first-layer X-ray detector 5A, it is possible to simultaneously capture an X-ray image of dual energy and a small-angle X-ray scattered image. That is, as illustrated in FIG. 23(b), among X-rays 3a transmitted by the X-ray transmitting materials R2 of the sample mask 7, X-rays P1 which are not refracted in the x direction are not incident on the light-shielding walls 17A but are incident on the scintillator elements 15A.

Accordingly, X-rays Pr of low energy among the X-rays P1 are not transmitted by the scintillator elements 15A, but are converted into scintillator light W and are detected by the pixels 21A. X-rays Ps of high energy among the X-rays P1 are transmitted by the X-ray detector 5A, are converted into scintillator light W by the scintillator elements 15B, and are detected by the pixels 21B. That is, as for the X-rays P1 which are not refracted in the x direction, the X-ray detector 5 according to Modified Example (13) serves as an X-ray detector of a dual energy type as a whole.

On the other hand, X-rays P2 which are refracted in the x direction due to transmission by a subject M or the like are incident on the scintillator elements 15A depending on the refraction distance Ja in the x direction and converted scintillator light is detected by the pixels 21A. Accordingly, information on the refraction distance Ja of X-rays 3a can be acquired by calculation between neighboring pixels 21A and a small-angle X-ray scattered image can be generated based on the information. That is, with the configuration according to Modified Example (11), it is possible to realize an X-ray detector that can simultaneously acquire an X-ray image based on dual energy X-ray imaging and a small-angle X-ray scattered image.

(14) In the above-mentioned modified examples having a multi-layer structure, a configuration in which the scintillator elements 15A and the light-shielding walls 17A extend in the y direction has been employed, but the present invention is not limited to this configuration. That is, as illustrated in FIG. 24(a), the light-shielding walls 17A may be arranged in a two-dimensional matrix shape in the x direction and the y direction. The initial positions of the sample mask 7 and the X-ray detector 5 are set such that the areas H in which X-rays 3a of a fan beam shape extending in the y direction are incident on the X-ray detector 5A overlap the scintillator elements 15A and the light-shielding walls 17A in the x direction.

In the configuration according to Modified Example (14), the X-ray incidence surface of the X-ray detector 5A has a structure in which an area F1 and an area F2 are alternately arranged in the y direction as illustrated in FIG. 24(a). The area F1 is an area in which the light-shielding walls 17A and the scintillator elements 15A are alternately arranged in the x direction. The area F2 is an area in which the light-shielding walls 17A are not disposed and only the scintillator elements 15A are disposed.

A cross-sectional view in the area F1, that is, a cross-sectional view taken along an A-A arrow in FIG. 24(a), has the same structure as in the first embodiment illustrated in FIG. 4(a). Accordingly, as for X-rays 3a incident on the area F1, a dose incident on the scintillator element 15A varies depending on the refraction direction and the refraction distance in the x direction. As a result, it is possible to acquire information of small-angle X-ray scattering in the area F1.

On the other hand, a cross-sectional view in the area F2, that is, a cross-sectional view taken along a B-B arrow in FIG. 24(a), has the same structure as illustrated in FIG. 24(b). Accordingly, among X-rays 3a incident on the area F2, X-rays Pr of relatively low energy are detected by the pixels 21A and X-rays Ps of relatively high energy are detected by the pixels 21B. As a result, it is possible to acquire information of an X-ray image based on X-ray imaging of dual energy in the area F2. In this way, in the configuration according to Modified Example (12), by setting a pixel 21 in the area F1 and a pixel 21 in the area F2, which are adjacent in the y direction, as one unit, it is possible to simultaneously acquire an X-ray image based on dual energy X-ray imaging and a small-angle X-ray scattered image based on the pixel values of the units.

(15) In the fourth embodiment and the like, a configuration for detecting the relative position deviation of the sample mask 7 and the X-ray detector 5 due to thermal expansion or vibration, or the like has been described, but a configuration for detecting a relative position deviation is not limited to this configuration. That is, as illustrated in FIG. 25(a), a configuration in which areas in which autoscopic striped patterns H (X-ray incidence areas) extending in the y direction overlap the scintillator elements 15 extending in the y direction are periodically changed for each of the scintillator elements 15 arranged in the x direction may be employed. In FIG. 25(a), a configuration in which the magnitude of the areas in which the scintillator elements 15a to 15j arranged in the x direction overlap the autoscopic striped patterns H is periodically changed is illustrated.

Details of the configuration according to Modified Example (15) will be described below with reference to FIG. 25(b). Here, a ratio of the area overlapping the autoscopic striped pattern H in each of the scintillator elements 15 is referred to as an "overlap ratio," and the description will be given. FIG. 25(b) is an enlarged view of an area Q indicated by a thick dotted line in FIG. 25(a).

In Modified Example (15), a width Hb of the autoscopic striped patterns H and a width B of the scintillator elements 15 are the same and the pitch Hp of the autoscopic striped patterns H and the pitch T of the scintillator elements 15 are different from each other. That is, an interval Hc between the striped patterns H adjacent in the x direction is different from an interval C between the scintillator elements 15 adjacent in the x direction. As a result, the overlap ratio in the scintillator element 15a is different from the overlap ratio in the scintillator element 15b.

For example, it is assumed that the interval C between the scintillator elements 15 is the same as the width B in the x direction of the scintillator elements 15 and the interval Hc between the striped patterns H is equal to 0.9 times the width Hb in the x direction of the striped patterns H. In this case, the pitch T of the scintillator elements 15 is equal to two times the width B of the scintillator elements 15 and the pitch Hp of the striped patterns H is equal to 1.9 times the width B of the scintillator elements 15.

Accordingly, the overlap ratio varies 10% between the scintillator elements 15 adjacent in the x direction. That is, when the overlap ratio of the scintillator element 15a is 0%, the overlap ratio of the scintillator element 15b is 10%. Accordingly, the overlap ratio of the scintillator elements 15 is changed from 0% to 50% in the scintillator elements 15 (the scintillator elements 15a to 15f) of six lines arranged in the x direction.

Subsequent to the scintillator element 15f, it is assumed that the interval Hc of the striped patterns H is equal to 1.1 times the width Hb of the striped patterns H. Accordingly, the overlap ratio of the scintillator elements 15 is changed from 40% to 0% in the scintillator elements 15g to 15k. The interval Hc is changed subsequent to the scintillator element 15k such that the change in the overlap ratio in the scintillator elements 15a to 15k is repeated.

As long as the overlap ratio can be periodically changed, the ratio of the interval Hc and the interval C and patterns for changing the interval Hc may be appropriately changed. For example, in the configuration in which the interval Hc is always 0.9 times the interval C, the overlap ratio in the scintillator elements 15 in eleven lines arranged in the x direction is changed from 0% to 100%. In the scintillator elements 15 in next ten lines, the overlap ratio is changed from 90% to 0%. In this way, even with a configuration in which the autoscopic striped patterns H and the scintillator elements 15 are arranged at equal intervals, it is possible to realize a periodic change of the overlap ratio from 0% to 0% via 100%.

The position of the periodic change of the overlap ratio according to Modified Example (15) is changed by deviating the relative position of the sample mask 7 and the X-ray detector 5. For example, when the relative position of the X-ray detector 5 to the sample mask 7 is rotationally deviated along the xy plane, the positional relationship of the autoscopic striped patterns H and the scintillator elements 15 is the same as illustrated in FIG. 25(c). At the initial position illustrated in FIG. 25(a), the periodic change of the overlap ratio is the same in the area F1 and the area F2 in which the coordinates in the y direction are different.

However, in the state in which the relative position is rotationally deviated as illustrated in FIG. 25(c), the periodic change of the overlap ratio in the area F1 is different from the periodic change of the overlap ratio in the area F2. Accordingly, it is possible to detect a deviation in the rotation direction by comparing the overlap ratios in the areas F1 and F2.

When the relative position is deviated in the direction parallel to the xy plane, the overlap ratios in the areas F1 and F2 are changed by the same value from the initial position illustrated in FIG. 25(a). When the relative position is deviated in the z direction, the change period of the overlap ratio varies from the initial state. Accordingly, by calculating the periodic change of the overlap ratio in the area F1 and the area F2 in which the coordinates in the y direction are different, it is possible to accurately detect a deviation of the relative position of the sample mask 7 and the X-ray detector 5 and to correct an influence of the deviation of the relative position on an X-ray image.

Accordingly, with the configuration according to Modified Example (15), it is possible to rapidly and easily correct an influence of the deviation of the relative position on an X-ray image and to acquire an X-ray image with higher accuracy. In this example, the overlap ratio is periodically changed by keeping the interval C of the scintillator elements 15 constant and changing the interval Hc of the striped patterns H, but the same advantages can be obtained in a configuration in which the interval Hc of the striped patterns H is kept constant and the interval C of the scintillator elements 15 is changed. An example in which the overlap ratio is changed in the entire area of the pixels 21 has been described, but the overlap ratio may be changed in only a partial area of the pixels 21. Particularly, it is possible to detect a deviation of the relative position in a region other than a region of interest of a subject by disposing an area in which the overlap ratio is changed at both ends of a pixel area.

(16) In the configurations of the above-mentioned embodiments, the arrangement pitch of the light-shielding walls 17 disposed in the first-layer X-ray detector 5 and the arrangement pitch of the light-shielding walls 17 disposed in the second or later-layer X-ray detector 5 are the same, but the present invention is not limited to this configuration. As illustrated in FIG. 26, the arrangement pitch of the light-shielding walls 17, that is, the light-shielding walls 17A, in the first-layer X-ray detector 5A may be different from the arrangement pitch of the light-shielding walls 17, that is, the light-shielding walls 17B, in the second-layer X-ray detector 5B.

In this case, the arrangement pitch of the scintillator elements 15A and the arrangement pitch of the pixels 21A in the X-ray detector 5A are the same as the arrangement pitch of the light-shielding walls 17A. Similarly, the arrangement pitch of the scintillator elements 15B and the arrangement pitch of the pixels 21B in the X-ray detector 5B are the same as the arrangement pitch of the light-shielding walls 17B. Accordingly, the arrangement pitch of the pixels 21A and the arrangement pitch of the pixels 21B are different from each other.

Particularly, when the arrangement pitch of the light-shielding walls 17B is set to be larger than arrangement pitch of the light-shielding walls 17A, the light-shielding walls 17B can be disposed on a straight line connecting an X-ray focal point p of an X-ray source to the light-shielding walls 17A as illustrated in FIG. 26. When X-rays are spread in a radial shape, the spreading width of X-rays transmitted by the scintillator layer 11B is larger than the spreading width of X-rays transmitted by the scintillator layer 11A.

Accordingly, in FIG. 26, in view of these circumstances, the width of the scintillator layer 11A in the first-layer X-ray detector 5A is set to be small and the scintillator layer 11B in the second-layer X-ray detector 5B is set to be large to correspond to a beam width of X-rays. Regarding the arrangement pitch of the light-shielding walls 17, in view of the beam width of X-rays, the arrangement pitch of the light-shielding walls 17A in the first-layer X-ray detector 5A is set to be small and the arrangement pitch of the light-shielding walls 17B in the second-layer X-ray detector 5B is set to be large.

Specifically, in the configuration according to Modified Example (16), it is preferable that the ratio of the pitch of the light-shielding walls 17A and the pitch of the light-shielding walls 17B be equal to the ratio of the spreading width when X-rays 3a emitted from the X-ray tube 3 reach the scintillator layer 11A and the spreading width when X-rays 3a emitted from the X-ray tube 3 reach the scintillator layer 11B.

Accordingly, in view of an X-ray beam which spreads in a radial shape, the light-shielding walls 17B are arranged as if they extend from the light-shielding walls 17A. The X-ray detectors 5 according to this modified example can be applied to the configurations of the above-mentioned embodiments. In each of the X-ray detectors 5, the arrangement pitch of the light-shielding walls 17 may be changed while keeping the arrangement pitch of the pixels 21 constant.

(17) In the above-mentioned embodiments, the light-shielding walls are arranged to be parallel to each other, but the present invention is not limited to this configuration. As illustrated in FIG. 27, the light-shielding walls may be configured to be gradually inclined from the center of the scintillator layer 11 to the end. In FIG. 27, the configuration of the output layer 13 including the pixels 21 are not illustrated. In FIG. 27, the light-shielding walls 17 are configured to extend along a straight line passing through the focal point p of the X-ray source. Accordingly, since X-rays 3a can be prevented from being detected from both neighboring pixels 21, it is possible to provide an X-ray detector with high accuracy. The configuration of the light-shielding walls 17 illustrated in FIG. 27 can be applied to the configurations of the X-ray detectors 5 according to the embodiments. The light-shielding walls 17 according to the present invention are configured to be gradually inclined from the center of a lattice to the end.

(18) In the above-mentioned embodiments, ends of neighboring pixels border each other, but the present invention is not limited to this configuration. As illustrated in FIG. 28, the light-shielding walls 17 may be configured to extend to side faces of the pixels 21. In FIG. 28, the pixels 21 are located inside cells which are formed by the lattice of the light-shielding walls 17. With the configuration according to Modified Example (18), it is possible to satisfactorily optically isolate neighboring pixels 21 from each other. Since photoelectric conversion elements of the pixels 21 are not disposed in areas in which the light-shielding walls 17 are disposed, the photoelectric conversion elements of the pixels 21 can detect scintillator light W without waste.

The configuration according to Modified Example (18) is not limited to the configuration in which the pixels 21 are disposed inside the lattice of the light-shielding walls 17. That is, as long as the photoelectric conversion elements of neighboring pixels 21 can be optically isolated from each other, the entire pixels 21 may not be isolated by the light-shielding walls 17. For example, the photoelectric conversion elements of the pixels 21 can be located inside compartments which are formed by the lattice of the light-shielding walls 17. The X-ray detectors 5 according to this modified example can be applied to the configurations of the embodiments.

(19) In the above-mentioned embodiments, the light-shielding walls 17 according to the present invention may be manufactured by lithography (LIGA) using X-rays or ultraviolet rays. It is possible to easily manufacture the light-shielding walls 17 with a more precise and complicated shape by using such a method. In particular, when the light-shielding walls 17 having the configuration according to Modified Example (17) are manufactured, LIGA can be preferably used. That is, by emitting X-rays or the like such that the light-shielding walls are gradually inclined from the center of the scintillator layer 11 to the end thereof, it is possible to easily manufacture the light-shielding walls 17 which are configured to be gradually inclined from the center of the scintillator layer 11 to the end thereof.

(20) In the above-mentioned embodiments, a configuration in which a subject M is disposed between the sample mask 7 and the X-ray detector 5 has been described above, but the subject M may be disposed between the X-ray tube 3 and the sample mask 7. With this configuration, it is possible to enhance an enlargement ratio. Accordingly, it is possible to provide an X-ray imaging device which is more useful for nondestructive inspection.

REFERENCE SIGNS LIST

1 . . . X-ray imaging device
3 . . . X-ray tube
5 . . . X-ray detector
7 . . . sample mask
11 . . . scintillator layer
13 . . . output layer
15 . . . scintillator element
17 . . . light-shielding wall
19 . . . substrate
21 . . . pixel
23 . . . scintillator array

The invention claimed is:

1. An X-ray imaging device comprising:
an X-ray tube that emits X-rays to a subject;
a shielding mask which is disposed between the X-ray tube and the subject and in which X-ray transmitting portions extending in a first direction are arranged parallel in a second direction perpendicular to the first direction;
an X-ray detector that detects X-rays transmitted by the X-ray transmitting portions and outputs an X-ray detection signal;
a moving mechanism that moves a relative position of the X-ray detector and the shielding mask in the second direction;
an X-ray emission control unit that performs control of causing the X-ray tube to repeatedly emit X-rays while the moving mechanism moves the relative position;
an image generating unit that generates an X-ray image using the X-ray detection signal output from the X-ray detector every emission of X-rays from the X-ray tube;
a refraction information calculating unit that calculates X-ray refraction information including a refraction direction and a refraction angle of X-rays based on the X-ray image generated by the image generating unit; and
a scattered image reconstructing unit that reconstructs a small-angle X-ray scattered image mirroring an X-ray refraction contrast image of the subject based on the X-ray refraction information,
wherein the X-ray detector comprises a scintillator layer including light-shielding walls in a lattice shape and scintillator elements that are disposed in cells which are defined in a two-dimensional matrix shape by the light-shielding walls and convert incident X-rays into light, and
an output layer in which pixels that convert light converted by the scintillator elements into electric charges are arranged in a two-dimensional matrix shape.

2. The X-ray imaging device according to claim 1, wherein the X-ray detector comprises:
a first scintillator layer;
a second scintillator layer;
a first output layer in which pixels that convert light converted by the scintillator elements disposed in the first scintillator layer into electric charges are arranged in a two-dimensional matrix shape; and
a second output layer in which pixels that convert light converted by the scintillator elements disposed in the second scintillator layer into electric charges are arranged in a two-dimensional matrix shape, and a lattice pattern of the light-shielding walls disposed in the first scintillator layer and a lattice pattern of the light-shielding walls disposed in the second scintillator layer are deviated along the X-ray incident surface.

3. The X-ray imaging device according to claim 2, wherein a ratio a pitch of the light-shielding walls disposed in the first scintillator layer and a pitch of the light-shielding walls disposed in the second scintillator layer is the same as a ratio of a spreading width when X-rays emitted from the X-ray tube reach the first scintillator layer and a spreading width when X-rays emitted from the X-ray tube reach the second scintillator layer.

4. The X-ray imaging device according to claim 1, wherein the X-ray detector comprises:
   the scintillator layer;
   a scintillator panel that includes the scintillator elements;
   a first output layer in which pixels that convert light converted by the scintillator elements disposed in the scintillator layer into electric charges are arranged in a two-dimensional matrix shape; and
   a second output layer in which pixels that convert light converted by the scintillator elements disposed in the scintillator panel into electric charges are arranged in a two-dimensional matrix shape, and
   the scintillator layer and the scintillator panel are stacked in an incidence direction of the X-rays.

5. The X-ray imaging device according to claim 4, wherein a pitch of the pixels disposed in the scintillator panel is larger than a pitch of the pixels disposed in the scintillator layer.

6. The X-ray imaging device according to claim 1, wherein photoelectric conversion elements disposed in the pixels are located in compartments which are formed by the lattice of the light-shielding walls.

7. The X-ray imaging device according to claim 1, wherein the light-shielding walls are configured to be gradually inclined from a center of the X-ray detector to an end thereof.

8. The X-ray imaging device according to claim 1, wherein the X-ray transmitting portions and the X-ray detector are configured such that a magnitude of an area in which the area in which the X-rays are incident on the X-ray detector overlaps the scintillator elements extending in the first direction varies periodically for each of the scintillator elements arranged in the second direction.

9. The X-ray imaging device according to claim 1, wherein the positions of the X-ray transmitting portions and the X-ray detector are set such that the area in which the X-rays are incident on the X-ray detector circumscribes two or more scintillator elements or two or more light-shielding walls in the second direction.

10. An X-ray imaging device comprising:
    an X-ray tube that emits X-rays to a subject;
    a shielding mask which is disposed between the X-ray tube and the subject and in which X-ray transmitting portions extending in a first direction are arranged parallel in a second direction perpendicular to the first direction;
    an X-ray detector that detects X-rays transmitted by the X-ray transmitting portions and outputs an X-ray detection signal;
    an image generating unit that generates an X-ray image using the X-ray detection signal output from the X-ray detector;
    a refraction information calculating unit that calculates X-ray refraction information including a refraction direction and a refraction angle of X-rays based on the X-ray image generated by the image generating unit; and
    a scattered image reconstructing unit that reconstructs a small-angle X-ray scattered image mirroring an X-ray refraction contrast image of the subject based on the X-ray refraction information,
    wherein the X-ray detector comprises a scintillator layer including light-shielding walls in a lattice shape and scintillator elements that are disposed in cells which are defined in a two-dimensional matrix shape by the light-shielding walls and convert incident X-rays into light, and
    an output layer in which pixels that convert light converted by the scintillator elements into electric charges are arranged in a two-dimensional matrix shape, and
    positions of the X-ray transmitting portions and the X-ray detector are set such that an area in which the X-rays are incident on the X-ray detector overlaps two or more scintillator elements in the second direction.

11. The X-ray imaging device according to claim 10, wherein the X-ray detector comprises:
    a first scintillator array that includes the light-shielding walls in a lattice shape and first scintillator elements that are defined by the light-shielding walls and are arranged in the second direction; and
    a second scintillator array that includes the light-shielding walls in a lattice shape and second scintillator elements that are defined by the light-shielding walls and are arranged in the second direction and in which an arrangement pattern of the second scintillator elements is deviated by a predetermined distance in the second direction from an arrangement pattern of the first scintillator elements, and
    the first scintillator array and the second scintillator array are alternately arranged in the first direction.

12. An X-ray imaging device comprising:
    an X-ray tube that emits X-rays to a subject;
    a shielding mask which is disposed between the X-ray tube and the subject and in which X-ray transmitting portions are arranged in a two-dimensional matrix shape in two directions perpendicular to each other;
    an X-ray detector that detects X-rays transmitted by the X-ray transmitting portions and outputs an X-ray detection signal;
    an image generating unit that generates an X-ray image using the X-ray detection signal output from the X-ray detector;
    a refraction information calculating unit that calculates X-ray refraction information including a refraction direction and a refraction angle of X-rays based on the X-ray image generated by the image generating unit; and
    a scattered image reconstructing unit that reconstructs a small-angle X-ray scattered image mirroring an X-ray refraction contrast image of the subject based on the X-ray refraction information,
    wherein the X-ray detector comprises a scintillator layer including light-shielding walls in a lattice shape and scintillator elements that are disposed in cells which are defined in a two-dimensional matrix shape by the light-shielding walls and convert incident X-rays into light, and an output layer in which pixels that convert light converted by the scintillator elements into electric charges are arranged in a two-dimensional matrix shape, and positions of the X-ray transmitting portions and the X-ray detector are set such that an area in which the X-rays are incident on the X-ray detector overlaps two or more scintillator elements in the two directions perpendicular to each other.

13. The X-ray imaging device according to claim 12 wherein the positions of the X-ray transmitting portions and the X-ray detector are set such that an area in which the X-rays are incident on the X-ray detector circumscribes the two or more scintillator elements in the two directions perpendicular to each other.

* * * * *